(12) United States Patent
Datta et al.

(10) Patent No.: US 7,139,665 B2
(45) Date of Patent: Nov. 21, 2006

(54) COMPUTATIONAL METHOD FOR DESIGNING ENZYMES FOR INCORPORATION OF NON NATURAL AMINO ACIDS INTO PROTEINS

(75) Inventors: Deepshikha Datta, South Pasadena, CA (US); Pin Wang, Pasadena, CA (US); Isaac Carrico, Pasadena, CA (US); Stephen L. Mayo, Pasadena, CA (US); David Tirrell, Pasadena, CA (US)

(73) Assignee: California Institute of Technology, Pasadena, CA (US)

( * ) Notice: Subject to any disclaimer, the term of this patent is extended or adjusted under 35 U.S.C. 154(b) by 431 days.

(21) Appl. No.: 10/375,298

(22) Filed: Feb. 27, 2003

(65) Prior Publication Data

US 2004/0053390 A1    Mar. 18, 2004

Related U.S. Application Data

(60) Provisional application No. 60/360,146, filed on Feb. 27, 2002.

(51) Int. Cl.
G06F 17/00 (2006.01)
G06F 17/11 (2006.01)
G06F 17/30 (2006.01)

(52) U.S. Cl. .................. 702/19; 702/27; 530/300; 530/350

(58) Field of Classification Search .............. 702/19, 702/27
See application file for complete search history.

(56) References Cited

U.S. PATENT DOCUMENTS 6,269,312 B1    7/2001  Mayo et al.
2001/0051855 A1  12/2001  Wang et al.
2002/0004706 A1   1/2002  Mayo et al.
2002/0072864 A1*  6/2002  Lacroix et al. .............. 702/27

OTHER PUBLICATIONS

Ohno et al (J Biochem (Tokyo), Sep. 2001; 130(3):417-23; see abstract.*
Datta et al., A Designed Phenylalanyl-tRNA Synthetase Variant Allows Efficient in vivo Incorporation of Aryl Ketone Functionality into Proteins. Journal of the American Chemical Society, 124(20):5652-5653, 2002.
Dahiyat et al., De novo Protein Design: Fully Automated Sequence Selection. Science 278(5335): 82-87, 1997.
Dahiyat and Mayo, Protein Design Automation. *Protein Science* 5: 895-903, 1993.
IBBA et al., Relaxing the Substrate Specificity of an Aminoacyl-tRNA Synthetase Allows in vitro and in vivo Synthesis of Proteins Containing Unnatural Amino Acids. FEBS Letters 364: 272-275, 1994.
OHNO et al., Changing the amino acid specificity of yeast tyrosyl-tRNA synthetase by genetic engineering. *J. Biochem* (Tokyo). 130(3): 417-23, 2001. (Abstract).
Reshetnikova et al. Crystal Structures of Phenylalanyl-tRNA Synthetase Complexed with Phenylalanine and a Phenylalanyl-adenylate Analogue. Journal of Molecular Biology 287(3): 555-568, 1999.
Zhang et al., Structure-based design of mutant *Methanococcus jannaschii* tyrosyl-tRNA synthetase for incorporation of O-methyl-L-tyrosine. *Proc Natl Acad Sci U S A*. 99(10): 6579-6584, 2002.

* cited by examiner

*Primary Examiner*—Michael Borin
(74) *Attorney, Agent, or Firm*—Seed Intellectual Property Law Group PLLC

(57) ABSTRACT

The instant invention provides methods, reagents, and computational tools for designing non-natural substrate analogs for enzymes, especially for designing unnatural amino acid analogs for aminoacyl tRNA Synthetases (AARSs), such as the Phe tRNA Synthetase. The instant invention also provides methods to incorporate unnatural amino acid analogs, especially those with interesting functional groups, into protein products to generate proteins of modified or novel functions.

30 Claims, 7 Drawing Sheets

SEQUENCE LISTING

<160> NUMBER OF SEQ ID NOS: 3

<210> SEQ ID NO 1
<211> LENGTH: 14
<212> TYPE: PRT
<213> ORGANISM: Mus musculus

-continued

```
<220> FEATURE:
<223> OTHER INFORMATION: mouse DHFR protein residues 93-106

<400> SEQUENCE: 1

Glu Leu Lys Glu Pro Pro Arg Gly Ala His Phe Leu Ala Lys
1               5                   10

<210> SEQ ID NO 2
<211> LENGTH: 14
<212> TYPE: PRT
<213> ORGANISM: Mus musculus
<220> FEATURE:
<223> OTHER INFORMATION: mouse DHFR protein residues 34-47

<400> SEQUENCE: 2

Asn Gly Asp Leu Pro Trp Pro Pro Leu Arg Asn Glu Phe Lys
1               5                   10

<210> SEQ ID NO 3
<211> LENGTH: 126
<212> TYPE: DNA
<213> ORGANISM: Artificial Sequence
<220> FEATURE:
<223> OTHER INFORMATION: linker encoding a tac promoter

<400> SEQUENCE: 3
ctagcagttg acaattaatc atcggctcgt ataatggatc gaattgtgag cggaatcgat      60
tttcacacag gaaacagacc atggatcttc gtcgccatcc tcgggtcgac gtctgttgca    120
agcttg                                                               126
```

COMPUTATIONAL METHOD FOR DESIGNING ENZYMES FOR INCORPORATION OF NON NATURAL AMINO ACIDS INTO PROTEINS

REFERENCE TO RELATED APPLICATION

This application claims the benefit under 35 U.S.C. 119(e) of U.S. Provisional Application No. 60/360,146, filed on Feb. 27, 2002, the entire content of which is incorporated herein by reference.

GOVERNMENT SUPPORT

Part of this work was supported by NIH Grants R01-GM62523 and T32-GM08501 awarded to the NSF Center for the Science and Engineering of Materials at Caltech. The Government has certain rights in this invention.

BACKGROUND OF THE INVENTION

Protein engineering is a powerful tool for modification of the structural catalytic and binding properties of natural proteins and for the de novo design of artificial proteins. Protein engineering relies on an efficient recognition mechanism for incorporating mutant amino acids in the desired protein sequences. Though this process has been very useful for designing new macromolecules with precise control of composition and architecture, a major limitation is that the mutagenesis is restricted to the 20 naturally occurring amino acids. However, it is becoming increasingly clear that incorporation of non-natural amino acids can extend the scope and impact of protein engineering methods.[1] Thus, for many applications of designed macromolecules, it would be desirable to develop methods for incorporating amino acids that have novel chemical functionality not possessed by the 20 amino acids commonly found in naturally occuring proteins. That is, ideally, one would like to tailor changes in a protein (the size, acidity, nucleophilicity, hydrogen-bonding or hydrophobic properties, etc. of amino acids) to fulfill a specific structural or functional property of interest. The ability to incorporate such amino acid analogs into proteins would greatly expand our ability to rationally and systematically manipulate the structures of proteins, both to probe protein function and create proteins with new properties. For example, the ability to synthesize large quantities of proteins containing heavy atoms would facilitate protein structure determination, and the ability to site specifically substitute fluorophores or photo-cleavable groups into proteins in living cells would provide powerful tools for studying protein functions in vivo. One might also be able to enhance the properties of proteins by providing building blocks with new functional groups, such as an amino acid containing a keto-group.

Incorporation of novel amino acids in macromolecules has been successful to an extent. Biosynthetic assimilation of non-canonical amino acids into proteins has been achieved largely by exploiting the capacity of the wild type synthesis apparatus to utilize analogs of naturally occurring amino acids (Budisa 1995, *Eur. J. Biochem* 230: 788–796; Deming 1997, *J. Macromol. Sci. Pure Appl. Chem* A34; 2143–2150; Duewel 1997, *Biochemistry* 36: 3404–3416; van Hest and Tirrell 1998, *FEBS Lett* 428(1–2): 68–70; Sharma et al., 2000, *FEBS Lett* 467(1): 37–40). Nevertheless, the number of amino acids shown conclusively to exhibit translational activity in vivo is small, and the chemical functionality that has been accessed by this method remains modest. In designing macromolecules with desired properties, this poses a limitation since such designs may require incorporation of complex analogs that differ significantly from the natural substrates in terms of both size and chemical properties and hence, are unable to circumvent the specificity of the synthetases. Thus, to further expand the range of non-natural amino acids that can be incorporated, there is a need to manipulate the activity of the aminoacyl tRNA synthetases (AARS).

Protein translation from an mRNA template is carried out by ribosomes. During the translation process, each tRNA is matched with its amino acid long before it reaches the ribosome. The match is made by a collection of enzymes known as the aminoacyl-tRNA synthetases (AARS). These enzymes charge each tRNA with the proper amino acid, thus allowing each tRNA to make the proper translation from the genetic code of DNA (and the mRNA transcribed from the DNA) into the amino acid code of proteins.

Most cells make twenty different aminoacyl-tRNA synthetases, one for each type of amino acid. These twenty enzymes are each optimized for function with its own particular amino acid and the set of tRNA molecules appropriate to that amino acid. Aminoacyl-tRNA synthetases must perform their tasks with high accuracy. Many of these enzymes recognize their tRNA molecules using the anticodon. These enzymes make about one mistake in 10,000. For most amino acids, this level of accuracy is not too difficult to achieve, since most of the amino acids are quite different from one another.

SUMMARY OF THE INVENTION

The instant invention provides methods and computational tools for systematically modifying the substrate specificity of AminoAcyl tRNA Synthetases (AARSs) to enable them to utilize amino acid analogs in cell-free and whole cell translation systems. Specifically, the instant invention provides methods and tools for redesigning the substrate binding site in the synthetases to facilitate the accommodation of amino acid analogs.

Thus one aspect of the invention provides a method for generating a mutant aminoacyl tRNA synthetase (AARS), comprising: (i) providing the coordinates for a plurality of different rotamers of an amino acid analog resulting from varying torsional angles; (ii) providing a set of structure coordinates for amino acid residues that define a binding pocket for an aminoacyl tRNA synthetase; (iii) modeling interactions of said rotamers with said binding pocket and identifying non-bond interactions between said residues of said binding pocket and said rotamers; (iv) altering one or more amino acid residues in said binding pocket to produce one or more sets of structure coordinates that define altered binding pockets for mutants of said aminoacyl tRNA synthetases; (v) modeling interactions of said rotamers with said one or more altered binding pockets; and, (vi) generating a set of optimized aminoacyl tRNA synthetases sequences having favorable interactions with said amino acid analog.

In one embodiment, the step generating a set of optimized aminoacyl tRNA synthetases sequences includes a Dead-End Elimination (DEE) computation to remove rotamers from said rotamer library and use in said modeling steps.

In one embodiment, the amino acid analog has a non-naturally occurring sidechain.

In one embodiment, the amino acid analog is a D-enantiomer.

Another aspect of the invention provides a method for synthesizing a peptide or protein incorporating one or more amino acid analogs, comprising providing a translational system including: (i) a transcript, or means for generating a transcript, that encodes a peptide or polypeptide, and (ii) one or more mutant AARS having a mutated binding pocket, each of which AARS catalyze incorporation of an amino acid analog into said peptide or protein under the conditions of the translation system.

In one embodiment, said translation system is a whole cell that expresses said one or more AARS.

In one embodiment, said translation system is a cell lysate or reconstituted protein preparation that is translation competent.

In one embodiment, at least one of said mutant AARS catalyzes incorporation of said amino acid analog with a $K_{cat}$ at least 10 fold greater than the wild-type AARS.

In one embodiment, at least one of said mutant AARS has a sequence identified by the method of claim 1.

Any of these embodiments may be combined as appropriate.

Another aspect of the invention provides a peptide or polypeptide incorporating one or more amino acid analogs, which peptide or polypeptide was produced by any of the above-describes methods or combinations thereof.

Another aspect of the invention provides a method for conducting a biotechnology business comprising: (i) identifying a mutant AARS sequences, by the method of claim 1, which binds to a amino acid analog; (ii) providing a translation system including: (a) a transcript, or means for generating a transcript, that encodes a peptide or polypeptide, (b) an AARS having said identified mutant AARS sequence, and (c) said amino acid analog, under circumstances wherein said AARS catalyzes incorporation of said amino acid analog in said peptide or polypeptide.

In one embodiment, the method further comprises the step of providing a packaged pharmaceutical including the peptide or polypeptide, and instructions and/or a label describing how to administer said peptide or polypeptide.

Another aspect of the invention provides a method for generating a mutant aminoacyl tRNA synthetase (AARS), comprising: (i) providing a set of structure coordinates for amino acid residues that define a binding pocket for a mutant aminoacyl tRNA synthetase, which binding pocket varies by at least one residue from the sequence of the wild-type form of said aminoacyl tRNA synthetase; (ii) providing a rotamer library of a plurality of amino acid analogs which represents the coordinates for a plurality of different conformations of each of said analogs resulting from varying torsional angles; (iii) modeling interactions of said rotamers with said binding pocket and identifying non-bond interactions between residues of the binding pocket and the amino acid analogs; (iv) identifying amino acid analogs that have favorable interactions with said mutant aminoacyl tRNA synthetase.

Another aspect of the invention provides a method for designing amino acid sequence change(s) in an aminoacyl tRNA synthetase (AARS), wherein said change would enable said AARS to incorporate an amino acid analog of a natural amino acid substrate of said AARS into a protein in vivo, comprising: (a) establishing a three-dimentional structure model of said AARS with said natural amino acid substrate; (b) establishing a rotamer library for said amino acid analog; (c) identifying, based on said three-dimentional structure model, anchor residues of said AARS interacting with the backbone of said natural amino acid substrate; (d) identifying, in the binding pocket of said AARS, amino acid position(s) involved in interaction with the side chain of said natural amino acid substrate as candidate variable residue position(s); (e) establishing an AARS-analog backbone structure by substituting said natural amino acid substrate with said amino acid analog in said three-dimentional structure model, wherein the geometric orientation of the backbone of said amino acid analog is specified by the orientation of the backbone of said natural amino acid substrate, and wherein the backbone of said amino acid analog and all anchor residues identified in (c) are fixed in identity and rotameric conformation in relation to said AARS-analog backbone structure; (f) establishing a group of potential rotamers for each of the candidate variable residue position(s) identified in (d), wherein the group of potential rotamers for at least one of said variable residue residue position(s) has a rotamer selected from each of at least two diferent amino acid side chains; and (g) analyzing the interaction of each of the rotamers for said amino acid analog and rotamers for said variable residue position(s) with all or part of the remainder of said AARS-analog backbone structure to generate a set of optimized protein sequences, wherein said analyzing step includes a Dead-End Elimination (DEE) canmputation; wherein steps (b)–(d) are carried out in any order.

In one embodiment, the method further comprises (h) identifying additional protein sequence changes that favor interaction between said AARS and said amino acid analog, by repeating step (g) while scaling up interactions between said amino acid analog and said variable residue position(s).

In one embodiment, the method further comprises testing said AARS in vivo for its ability, specificity, and/or efficiency for incorporating said amino acid analog into a protein.

In one embodiment, said three-dimentional structure model is a known crystallographic or NMR structure.

In one embodiment, said three-dimentional structure model is established by homology modeling based on a known crystallographic or NMR structure of a homolog of said AARS.

In one embodiment, said homolog is at least about 70% identical to said AARS in the active site region.

In one embodiment, the rotamer library for said amino acid analog is a backbone-independent rotamer library.

In one embodiment, the rotamer library for said amino acid analog is a rotamer library established by varying both the χ1 and χ2 torsional angles by ±20 degrees, in increment of 5 degrees, from the values of said natural amino acid susbtrate in said AARS structure.

In one embodiment, said AARS is Phe tRNA Synthetase (PheRS). Preferably, said PheRS is from *E. coli*.

In one embodiment, said AARS is from a eukaryote, such as human.

In one embodiment, said amino acid analog is a derivative of at least one of the 20 natural amino acids, with one or more functional groups not present in natural amino acids. For example, said functional group can be selected from the group consisting of: bromo-, iodo-, ethynyl-, cyano-, azido-, aceytyl, aryl ketone, a photolabile group, a fluoresent group, and a heavy metal. In a preferred embodiment, said amino acid analog is a derivative of Phe.

In one embodiment, said set of optimized protein sequences comprises the globally optimal protein sequence.

In one embodiment, said DEE computation is selected from the group consisting of original DEE and Goldstein DEE.

In one embodiment, said analyzing step includes the use of at least one scoring function. For example, said scoring function can be selected from the group consisting of a van der Waals potential scoring function, a hydrogen bond potential scoring function, an atomic solvation scoring function, an electrostatic scoring function and a secondary structure propensity scoring function. Also, said analyzing step includes the use of at least two scoring functions. In a preferred embodiment, said analyzing step includes the use of at least three scoring functions. In a preferred embodiment, said analyzing step includes the use of at least four scoring functions. In a preferred embodiment, said atomic salvation scoring function includes a scaling factor that compensates for over-counting.

In one embodiment, the method further comprises generating a rank ordered list of additional optimal sequences from said globally optimal protein sequence. In a preferred embodiment, said generating includes the use of a Monte Carlo search. In a preferred embodiment, the method further comprises testing some or all of said protein sequences from said ordered list to produce potential energy test results. In a preferred embodiment, the method further comprises analyzing the correspondence between said potential energy test results and theoretical potential energy data.

In one embodiment, said amino acid analog can be buried in the binding pocket of at least one of said set of optimized protein sequences, or wherein said amino acid analog is completely or almost completely superimposable with the natural amino acid substrate in said three-dimentional structure.

Any of the above embodiments can be combined as appropriate.

Another aspect of the invention provides a recombinant AARS protein generated by any of the above suitable methods or combinations thereof, said AARS protein comprising an optimized protein sequence that incorporates an amino acid analog of a natural amino acid substrate of said AARS into a protein in vivo.

Another aspect of the invention provides a nucleic acid sequence encoding a recombinant AARS protein that can be generated by any of the above suitable methods or combinations thereof.

Another aspect of the invention provides an expression vector comprising the nucleic acid sequence described above.

Another aspect of the invention provides a host cell comprising the nucleic acid sequence described above.

Another aspect of the invention provides an apparatus for generating a mutant aminoacyl tRNA synthetase (AARS), said apparatus comprising: (i) means for providing the coordinates for a plurality of different rotamers of an amino acid analog resulting from varying torsional angles; (ii) means for providing a set of structure coordinates for amino acid residues that define a binding pocket for an aminoacyl tRNA synthetase; (iii) means for modeling interactions of said rotamers with said binding pocket and identifying non-bond interactions between said residues of said binding pocket and said rotamers; (iv) means for altering one or more amino acid residues in said binding pocket to produce one or more sets of structure coordinates that define altered binding pockets for mutants of said aminoacyl tRNA synthetases; (v) means for modeling interactions of said rotamers with said one or more altered binding pockets; and, (vi) means for generating a set of optimized aminoacyl tRNA synthetases sequences having favorable interactions with said amino acid analog.

Another aspect of the invention provides a computer system for use in generating a mutant aminoacyl tRNA synthetase (AARS), said computer system comprising computer instructions for: (i) providing the coordinates for a plurality of different rotamers of an amino acid analog resulting from varying torsional angles; (ii) providing a set of structure coordinates for amino acid residues that define a binding pocket for an aminoacyl tRNA synthetase; (iii) modeling interactions of said rotamers with said binding pocket and identifying non-bond interactions between said residues of said binding pocket and said rotamers; (iv) altering one or more amino acid residues in said binding pocket to produce one or more sets of structure coordinates that define altered binding pockets for mutants of said aminoacyl tRNA synthetases; (v) modeling interactions of said rotamers with said one or more altered binding pockets; and, (vi) generating a set of optimized aminoacyl tRNA synthetases sequences having favorable interactions with said amino acid analog.

Another aspect of the invention provides a computer-readable medium storing a computer program executable by a plurality of server computers, the computer program comprising computer instructions for: (i) providing the coordinates for a plurality of different rotamers of an amino acid analog resulting from varying torsional angles; (ii) providing a set of structure coordinates for amino acid residues that define a binding pocket for an aminoacyl tRNA synthetase; (iii) modeling interactions of said rotamers with said binding pocket and identifying non-bond interactions between said residues of said binding pocket and said rotamers; (iv) altering one or more amino acid residues in said binding pocket to produce one or more sets of structure coordinates that define altered binding pockets for mutants of said aminoacyl tRNA synthetases; (v) modeling interactions of said rotamers with said one or more altered binding pockets; and, (vi) generating a set of optimized aminoacyl tRNA synthetases sequences having favorable interactions with said amino acid analog.

Another aspect of the invention provides a computer data signal embodied in a carrier wave, comprising computer instructions for: (i) providing the coordinates for a plurality of different rotamers of an amino acid analog resulting from varying torsional angles; (ii) providing a set of structure coordinates for amino acid residues that define a binding pocket for an aminoacyl tRNA synthetase; (iii) modeling interactions of said rotamers with said binding pocket and identifying non-bond interactions between said residues of said binding pocket and said rotamers; (iv) altering one or more amino acid residues in said binding pocket to produce one or more sets of structure coordinates that define altered binding pockets for mutants of said aminoacyl tRNA synthetases; (v) modeling interactions of said rotamers with said one or more altered binding pockets; and, (vi) generating a set of optimized aminoacyl tRNA synthetases sequences having favorable interactions with said amino acid analog.

Another aspect of the invention provides an apparatus comprising a computer readable storage medium having instructions stored thereon for: (i) accessing a datafile representative of the coordinates for a plurality of different rotamers of an amino acid analog resulting from varying torsional angles; (ii) accessing a datafile representative of a set of structure coordinates for amino acid residues that define a binding pocket for an aminoacyl tRNA synthetase; (iii) a set of modeling routines for (a) calculating interactions of said rotamers with said binding pocket and identifying non-bond interactions between residues of the binding pocket and the amino acid analog; (b) altering one or more amino acid residues in the binding pocket for the aminoacyl tRNA synthetase to produce one or more sets of structure coordinates that define altered binding pockets for mutants of said aminoacyl tRNA synthetases; (c) calculating interactions of said rotamers with said one or more altered binding pockets; and (d) generating a list representative of optimized aminoacyl tRNA synthetases sequences having favorable interactions with said amino acid analog.

DETAILED DESCRIPTION OF THE INVENTION

I. Overview

Figure 1:
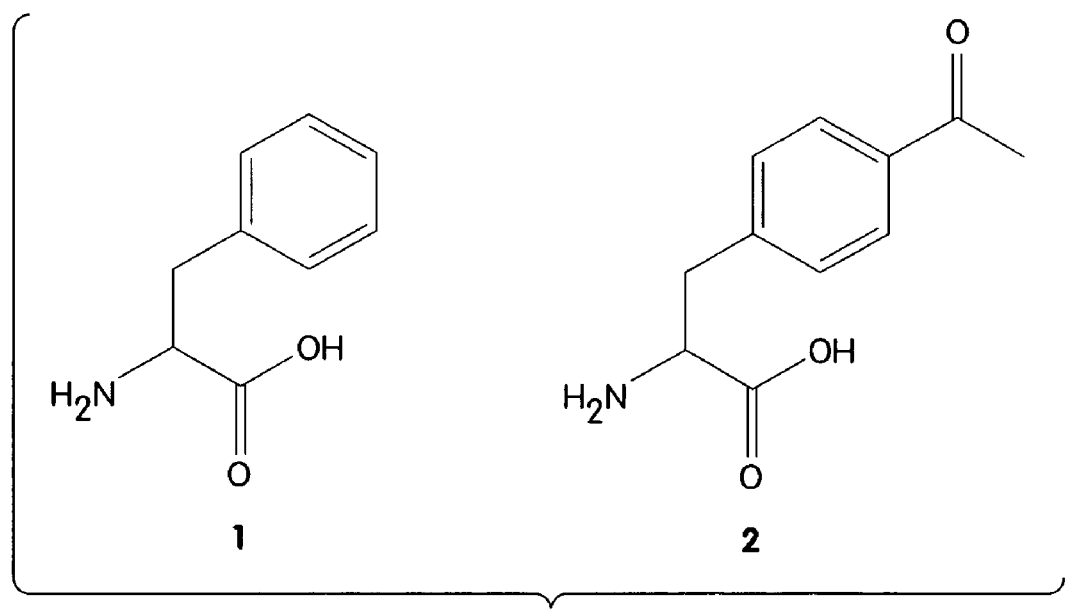
FIG. 1 Structure of phenylalanine (1) and p-acetylphenylalanine (2).

The instant invention provides methods and computational tools for modifying the substrate specificity of an AminoAcyl tRNA Synthetases (AARSs) through mutation to enable the enzyme to more efficiently utilize amino acid analog(s) in protein translation systems, either in vitro or in whole cells. A salient feature to the instant invention are methods and tools for systematically redesigning the substrate binding site of an AARS enzyme to facilitate the use of of unnatural substrates in the peptide or protein translation reaction the enzyme catalyzes.

In one embodiment, the subject method uses a rotamer library for the intended amino acid analog (or "analog"), e.g., which represents the coordinates for a plurality of different conformations of the analog resulting from varying torsional angles in the molecule. Members of the rotamer library are modeled in a docking simulation with a model of an AARS, e.g., which includes the coordinates for the substrate binding site of the enzyme. Amino acid residues (or "residues") in the binding pocket of the enzyme that interact with the amino acid analog unfavorably are varied in models of mutant AARS enzymes, the docking simulations are repeated, and mutant forms of the AARS enzyme which interact favorably with the amino acid analog are identified.

In certain embodiments, the computational method is developed to enhance the interactions between the analog and the protein positions. This is done by scaling up the pair-wise energies between the analog and the amino acids allowed at the design positions on the protein in the energy calculations. In an optimization calculation where the AARS-analog interactions are scaled up compared to the intra-protein interactions, sequence selection is biased toward selecting amino acid residues of AARS to be those that have favorable interaction with the analog.

In other embodiments, rather than holding the identity of the amino acid analog constant and varying the AARS structure (by modeling several different mutant structures), the subject method is carried out using the molecular model(s) for a single AARS mutant and sampling a variety of different amino acid analogs or potential fragments thereof, to identify analogs which are likely to interact with, and be substrates for the mutant AARS enzyme. This approach can make use of coordinate libraries for amino acid analogs (including rotamer variants) or libraries of functional groups and spacers that can be joined to form the sidechain of an amino acid analog.

Yet another aspect of the invention provides for use of a mutant AARS identified by one of the subject computational methods in the synthesis of a peptide or protein. Such mutant AARS enzymes can be used in cell-free translation systems, such as extracts or purified protein translation systems, or recombinantly expressed in whole cells, including in cells from a different organism. For example, AARS from one bacteria species (or a eukaryotic species such as yeast) can be recombinantly expressed in a different bacteria (or a different eukaryotic species such as insect, mammal or plant).

Another aspect of the invention provides peptides and polypeptide produced by a translation system using one or more of the subject AARS mutants, which peptides and polypeptides have one or more non-naturally occurring amino acid residues.

II. Definitions

The terms used in this specification generally have their ordinary meanings in the art, within the context of this invention and in the specific context where each term is used. Certain terms are discussed below or elsewhere in the specification, to provide additional guidance to the practitioner in describing the compositions and methods of the invention and how to make and use them. The scope an meaning of any use of a term will be apparent from the specific context in which the term is used.

"About" and "approximately" shall generally mean an acceptable degree of error for the quantity measured given the nature or precision of the measurements. Typical, exemplary degrees of error are within 20 percent (%), preferably within 10%, and more preferably within 5% of a given value or range of values. Alternatively, and particularly in biological systems, the terms "about" and "approximately" may mean values that are within an order of magnitude, preferably within 5-fold and more preferably within 2-fold of a given value. Numerical quantities given herein are approximate unless stated otherwise, meaning that the term "about" or "approximately" can be inferred when not expressly stated.

"Amino acid analog" is meant to include all amino acid-like compounds that are similar in structure and/or overall shape to one or more of the twenty L-amino acids commonly found in naturally occuring proteins (Ala or A, Cys or C, Asp or D, Glu or E, Phe or F, Gly or G, His or H, Ile or I, Lys or K, Leu or L, Met or M, Asn or N, Pro or P, Gln or Q, Arg or R, Ser or S, Thr or T, Val or V, Trp or W, Tyr or Y, as defined and listed in WIPO Standard ST.25 (1998), Appendix 2, Table 3). Amino acid analog can also be natural amino acids with side chains or backbones. Preferably, these analogs usually are not "substrates" for the AARSs because of the high specificity of the AARSs, although occasionally, certain analogs with structures/shapes sufficiently close to natural amino acids may be erroneously incorporated into the protein by AARSs, especially mutant AARSs with relaxed substrate specificity. In a preferred embodiment, the analogs share backbone structures, and/or even the most side chain structures of one or more natural amino acids, with the only difference(s) being conatining one or more modified groups in the molecule. Such modification may include, without limitation, substitution of an atom (such as N) for a related atom (such as S), addition of a group (such as methyl, or hydroxyl group, etc.) or an atom (such as Cl or Br, etc.), deletion of a group (supra), substitution of a covalent bond (single bond for double bond, etc.), or combinations thereof. Amino acid analogs may include α-hydroxy acids, and β-amino acids, and can also be referred to as "modified amino acids," "unnatural AARS substrates" or "non-canonical amino acids."

The amino acid analogs may either be naturally occuring or non-naturally occuring; as will be appreciated by those in the art, any structure for which a set of rotamers is known or can be generated can be used as an amino acid analog. The side chains may be in either the (R) or the (S) configuration (or D- or L-configuration). In a preferred embodiment, the amino acids are in the (S) or L-configuration.

Preferably, the overall shape and size of the amino acid analogs are such that, upon being charged to tRNAs by the re-designed AARS, the analog-tRNA is a ribosomally accepted complex, that is, the tRNA-analog complex can be accepted by the prokaryotic or eukaryotic ribosomes in an in vivo or in vitro translation system.

"Achor residues" are residue positions in AARS that maintain critical interactions between the AARS and the natural amino acid backbone.

"Backbone," or "template" includes the backbone atoms and any fixed side chains (such as the anchor residue side chains) of the protein (e.g., AARS). For calculation purposes, the backbone of an analog is treated as part of the AARS backbone.

"Protein backbone structure" or grammatical equivalents herein is meant the three dimensional coordinates that define the three dimensional structure of a particular protein. The structures which comprise a protein backbone structure (of a naturally occuring protein) are the nitrogen, the carbonyl carbon, the α-carbon, and the carbonyl oxygen, along with the direction of the vector from the α-carbon to the β-carbon.

The protein backbone structure which is input into the computer can either include the coordinates for both the backbone and the amino acid side chains, or just the backbone, i.e. with the coordinates for the amino acid side chains removed. If the former is done, the side chain atoms of each amino acid of the protein structure may be "stripped" or removed from the structure of a protein, as is known in the art, leaving only the coordinates for the "backbone" atoms (the nitrogen, carbonyl carbon and oxygen, and the α-carbon, and the hydrogens attached to the nitrogen and α-carbon).

Optionally, the protein backbone structure may be altered prior to the analysis outlined below. In this embodiment, the representation of the starting protein backbone structure is reduced to a description of the spatial arrangement of its secondary structural elements. The relative positions of the secondary structural elements are defined by a set of parameters called supersecondary structure parameters. These parameters are assigned values that can be systematically or randomly varied to alter the arrangement of the secondary structure elements to introduce explicit backbone flexibility. The atomic coordinates of the backbone are then changed to reflect the altered supersecondary structural parameters, and these new coordinates are input into the system for use in the subsequent protein design automation. For details, see U.S. Pat. No. 6,269,312, the entire content incorporated herein by reference.

"Conformational energy" refers generally to the energy associated with a particular "conformation", or three-dimensional structure, of a macromolecule, such as the energy associated with the conformation of a particular protein. Interactions that tend to stabilize a protein have energies that are represented as negative energy values, whereas interactions that destabilize a protein have positive energy values. Thus, the conformational energy for any stable protein is quantitatively represented by a negative conformational energy value. Generally, the conformational energy for a particular protein will be related to that protein's stability. In particular, molecules that have a lower (i.e., more negative) conformational energy are typically more stable, e.g., at higher temperatures (i.e., they have greater "thermal stability"). Accordingly, the conformational energy of a protein may also be referred to as the "stabilization energy."

Typically, the conformational energy is calculated using an energy "force-field" that calculates or estimates the energy contribution from various interactions which depend upon the conformation of a molecule. The force-field is comprised of terms that include the conformational energy of the alpha-carbon backbone, side chain—backbone interactions, and side chain—side chain interactions. Typically, interactions with the backbone or side chain include terms for bond rotation, bond torsion, and bond length. The backbone-side chain and side chain-side chain interactions include van der Waals interactions, hydrogen-bonding, electrostatics and solvation terms. Electrostatic interactions may include coulombic interactions, dipole interactions and quadrapole interactions). Other similar terms may also be included. Force-fields that may be used to determine the conformational energy for a polymer are well known in the art and include the CHARMM (see, Brooks et al, J. Comp. Chem. 1983, 4:187–217; MacKerell et al., in The Encyclopedia of Computational Chemistry, Vol. 1:271–277, John Wiley & Sons, Chichester, 1998), AMBER (see, Cornell et al., J. Amer. Chem. Soc. 1995, 117:5179; Woods et al., J. Phys. Chem. 1995, 99:3832–3846; Weiner et al., J. Comp. Chem. 1986, 7:230; and Weiner et al., J. Amer. Chem. Soc. 1984, 106:765) and DREIDING (Mayo et al., J. Phys. Chem. 1990, 94-:8897) force-fields, to name but a few.

In a preferred implementation, the hydrogen bonding and electrostatics terms are as described in Dahiyat & Mayo, Science 1997 278:82). The force field can also be described to include atomic conformational terms (bond angles, bond lengths, torsions), as in other references. See e.g., Nielsen J E, Andersen K V, Honig B, Hooft R W W, Klebe G, Vriend G, & Wade R C, "Improving macromolecular electrostatics calculations," Protein Engineering, 12: 657662(1999); Stikoff D, Lockhart D J, Sharp K A & Honig B, "Calculation of electrostatic effects at the amino-terminus of an alpha-helix," Biophys. J., 67: 2251–2260 (1994); Hendscb Z S, Tidor B, "Do salt bridges stabilize proteins—a continuum electrostatic analysis," Protein Science, 3: 211–226 (1994); Schneider J P, Lear J D, DeGrado W F, "A designed buried salt bridge in a heterodimeric coil," J. Am. Chem. Soc., 119: 5742–5743 (1997); Sidelar C V, Hendsch Z S, Tidor B, "Effects of salt bridges on protein structure and design," Protein Science, 7: 1898–1914 (1998). Solvation terms could also be included. See e.g., Jackson S E, Moracci M, elMastry N, Johnson C M, Fersht A R, "Effect of Cavity-Creating Mutations in the Hydrophobic Core of Chymotrypsin Inhibitor 2," Biochemistry, 32: 11259–11269 (1993); Eisenberg, D & McLachlan A D, "Solvation Energy in Protein Folding and Binding," Nature, 319: 199–203 (1986); Street A G & Mayo S L, "Pairwise Calculation of Protein Solvent-Accessible Surface Areas," Folding & Design, 3: 253–258 (1998); Eisenberg D & Wesson L, "Atomic salvation parameters applied to molecular dynamics of proteins in solution," Protein Science, 1: 227–235 (1992); Gordon & Mayo, supra.

"Coupled residues" are residues in a molecule that interact, through any mechanism. The interaction between the two residues is therefore referred to as a "coupling interaction." Coupled residues generally contribute to polymer fitness through the coupling interaction. Typically, the coupling interaction is a physical or chemical interaction, such as an electrostatic interaction, a van der Waals interaction, a hydrogen bonding interaction, or a combination thereof. As a result of the coupling interaction, changing the identity of either residue will affect the "fitness" of the molecule, particularly if the change disrupts the coupling interaction between the two residues. Coupling interaction may also be described by a distance parameter between residues in a molecule. If the residues are within a certain cutoff distance, they are considered interacting.

"Fitness" is used to denote the level or degree to which a particular property or a particular combination of properties for a molecule, e.g., a protein, are optimized. In certain embodiments of the invention, the fitness of a protein is preferably determined by properties which a user wishes to improve. Thus, for example, the fitness of a protein may refer to the protein's thermal stability, catalytic activity, binding affinity, solubility (e.g., in aqueous or organic solvent), and the like. Other examples of fitness properties include enantioselectivity, activity towards non-natural substrates, and alternative catalytic mechanisms. Coupling interactions can be modeled as a way of evaluating or predicting fitness (stability). Fitness can be determined or evaluated experimentally or theoretically, e.g. computationally.

Preferably, the fitness is quantitated so that each molecule, e.g., each amino acid will have a particular "fitness value". For example, the fitness of a protein may be the rate at which the protein catalyzes a particular chemical reaction, or the protein's binding affinity for a ligand. In a particularly preferred embodiment, the fitness of a protein refers to the conformational energy of the polymer and is calculated, e.g., using any method known in the art. See, e.g. Brooks B. R., Bruccoleri R E, Olafson, B D, States D J, Swaminathan S & Karplus M, "CHARMM: A Program for Macromolecular Energy, Minimization, and Dynamics Calculations," J. Comp. Chem., 4: 187–217 (1983); Mayo S L, Olafson B D & Goddard W A G, "DREIDING: A Generic Force Field for Molecular Simulations," J. Phys. Chem., 94: 8897–8909 (1990); Pabo C O & Suchanek E G, "Computer-Aided Model-Building Strategies for Protein Design," Biochemistry, 25: 5987–5991 (1986), Lazar G A, Desjarlais J R & Handel T M, "De Novo Design of the Hydrophobic Core of Ubiquitin," Protein Science, 6: 1167–1178 (1997); Lee C & Levitt M, "Accurate Prediction of the Stability and Activity Effects of Site Directed Mutagenesis on a Protein Core," Nature, 352: 448–451 (1991); Colombo G & Merz K M, "Stability and Activity of Mesophilic Subtilisin E and Its Thermophilic Homolog: Insights from Molecular Dynamics Simulations," J. Am. Chem. Soc., 121: 6895–6903 (1999); Weiner S J, Kollman P A, Case D A, Singh U C, Ghio C, Alagona G, Profeta S J, Weiner P, "A new force field for molecular mechanical simulation of nucleic acids and proteins," J. Am. Chem. Soc., 106: 765–784 (1984). Generally, the fitness of a protein is quantitated so that the fitness value increases as the property or combination of properties is optimized. For example, in embodiments where the thermal stability of a protein is to be optimized (conformational energy is preferably decreased), the fitness value may be the negative conformationl energy; i.e., F=−E.

The "fitness contribution" of a protein residue refers to the level or extent $f(i_a)$ to which the residue $i_a$, having an identity a, contributes to the total fitness of the protein. Thus, for example, if changing or mutating a particular amino acid residue will greatly decrease the protein's fitness, that residue is said to have a high fitness contribution to the polymer. By contrast, typically some residues $i_a$ in a protein may have a variety of possible identities a without affecting the protein's fitness. Such residues, therefore have a low contribution to the protein fitness.

"Dead-end elimination" (DEE) is a deterministic search algorithm that seeks to systematically eliminate bad rotamers and combinations of rotamers until a single solution remains. For example, amino acid residues can be modeled as rotamers that interact with a fixed backbone. The theoretical basis for DEE provides that, if the DEE search converges, the solution is the global minimum energy conformation (GMEC) with no uncertainty (Desmet et al., 1992).

Dead end elimination is based on the following concept. Consider two rotamers, $i_r$ and $i_t$, at residue i, and the set of all other rotamer configurations $\{S\}$ at all residues excluding i (of which rotamer $j_s$ is a member). If the pairwise energy contributed between $i_r$ and $j_s$ is higher than the pairwise energy between $i_t$ and $j_s$ for all $\{S\}$, then rotamer $i_r$ cannot exist in the global minimum energy conformation, and can be eliminated. This notion is expressed mathematically by the inequality.

$$E(i_r) + \sum_{j \neq i}^{N} E(i_r, j_s) > E(i_t) + \sum_{j \neq i}^{N} E(i_t, j_s)\{S\} \quad \text{(Equation A)}$$

If this expression is true, the single rotamer $i_r$ can be eliminated (Desmet et al., 1992).

In this form, Equation A is not computationally tractable because, to make an elimination, it is required that the entire sequence (rotamer) space be enumerated. To simplify the problem, bounds implied by Equation A can be utilized:

$$E(i_r) + \sum_{j \neq i}^{N} \min(s)E(i_r, j_s) > E(i_t) + \sum_{j \neq i}^{N} \max(s)E(i_t, j_s)\{S\} \quad \text{(Equation B)}$$

Using an analogous argument, Equation B can be extended to the elimination of pairs of rotamers inconsistent with the GMEC. This is done by determining that a pair of rotamers $i_r$ at residue i and $j_s$ at residue j, always contribute higher energies than rotamers $i_u$ and $j_v$ with all possible rotamer combinations $\{L\}$. Similar to Equation B, the strict bound of this statement is given by:

$$\varepsilon(i_r, j_s) + \sum_{k \neq i,j}^{N} \min(t)\varepsilon(i_r, j_s, k_t) > \varepsilon(i_u, j_v) + \sum_{k \neq i,j}^{N} \max(t)\varepsilon(i_u, j_v, k_t) \quad \text{(Equation C)}$$

where $\epsilon$ is the combined energies for rotamer pairs $$\epsilon(i_r, j_s) = E(i_r) + E(j_s) + E(i_r, j_s) \quad \text{(Equation D),}$$

and $$\epsilon(i_r, j_s, k_t) = E(i_r, k_t) + E(j_s, k_t) \quad \text{(Equation E).}$$

This leads to the doubles elimination of the pair of rotamers $i_r$ and $j_s$, but does not eliminate the individual rotamers completely as either could exist independently in the GMEC. The doubles elimination step reduces the number of possible pairs (reduces S) that need to be evaluated in the right-hand side of Equation 6, allowing more rotamers to be individually eliminated.

The singles and doubles criteria presented by Desmet et al. fail to discover special conditions that lead to the determination of more dead-ending rotamers For instance, it is possible that the energy contribution of rotamer $i_t$ is always lower than $i_r$ without the maximum of $i_t$ being below the minimum of $i_r$. To address this problem, Goldstein 1994 presented a modification of the criteria that determines if the energy profiles of two rotamers cross. If they do not, the higher energy rotamer can be determined to be dead-ending. The doubles calculation significantly more computational time than the singles calculation. To accelerate the process, other computational methods have been developed to predict the doubles calculations that will be the most productive (Gordon & Mayo, 1998). These kinds of modifications, collectively referred to as fast doubles, significantly improved the speed and effectiveness of DEE.

Several other modifications also enhance DEE. Rotamers from multiple residues can be combined into so-called super-rotamers to prompt further eliminations (Desmet et al., 1994; Goldstein, 1994). This has the advantage of eliminating multiple rotamers in a single step. In addition, it has been shown that "splitting" the conformational space between rotamers improves the efficiency of DEE (Pierce et al., 2000). Splitting handles the following special case. Consider rotamer $i_r$. If a rotamer $i_{t1}$ contributes a lower energy than $i_r$ for a portion of the conformational space, and a rotamer $i_{t2}$ has a lower energy than $i_r$ for the remaining fraction, then $i_r$ can be eliminated. This case would not be detected by the less sensitive Desmet or Goldstein criteria. In the preferred implementations of the invention as described herein, all of the described enhancements to DEE were used.

For further discussion of these methods see, Goldstein, R. F. (1994), Efficient rotamer elimination applied to protein side-chains and related spin glasses, *Biophysical Journal* 66, 1335–1340, Desmet, J., De Maeyer, M., Hazes, B. & Lasters, I. (1992), The dead-end elimination theorem and its use in protein side-chain positioning. *Nature* 356, 539–542; Desmet, J., De Maeyer, M. & Lasters, I. (1994), In *The Protein Folding Problem and Tertiary Structure Prediction* (Jr., K. M. & Grand, S. L., eds.), pp. 307–337 (Birkhauser, Boston); De Maeyer, M., Desmet, J. & Lasters, 1. (1997), All in one: a highly detailed rotamer library improves both accuracy and speed in the modeling of side chains by dead-end elimination, *Folding & Design* 2, 53–66, Gordon, D. B. & Mayo, S. L. (1998), Radical performance enhancements for combinatorial optimization algorithms based on the dead-end elimination theorem, *Journal of Computational Chemistry* 19, 1505–1514; Pierce, N. A., Spriet, J. A., Desmet, J., Mayo, S. L., (2000), Conformational splitting: A more powerful criterion for dead-end elimination; *Journal of Computational Chemistry* 21, 999–1009.

"Expression system" means a host cell and compatible vector under suitable conditions, e.g. for the expression of a protein coded for by foreign DNA carried by the vector and introduced to the host cell. Common expression systems include *E. coli* host cells and plasmid vectors, insect host cells such as Sf9, Hi5 or S2 cells and Baculovirus vectors, *Drosophila* cells (Schneider cells) and expression systems, and mammalian host cells and vectors.

"Host cell" means any cell of any organism that is selected, modified, transformed, grown or used or manipulated in any way for the production of a substance by the cell. For example, a host cell may be one that is manipulated to express a particular gene, a DNA or RNA sequence, a protein or an enzyme. Host cells may be cultured in vitro or one or more cells in a non-human animal (e.g., a transgenic animal or a transiently transfected animal).

The methods of the invention may include steps of comparing sequences to each other, including wild-type sequence to one or more mutants. Such comparisons typically comprise alignments of polymer sequences, e.g., using sequence alignment programs and/or algorithms that are well known in the art (for example, BLAST, FASTA and MEGALIGN, to name a few). The skilled artisan can readily appreciate that, in such alignments, where a mutation contains a residue insertion or deletion, the sequence alignment will introduce a "gap" (typically represented by a dash, "-", or "Δ") in the polymer sequence not containing the inserted or deleted residue.

"Homologous", in all its grammatical forms and spelling variations, refers to the relationship between two proteins that possess a "common evolutionary origin", including proteins from superfamilies in the same species of organism, as well as homologous proteins from different species of organism. Such proteins (and their encoding nucleic acids) have sequence homology, as reflected by their sequence similarity, whether in terms of percent identity or by the presence of specific residues or motifs and conserved positions.

The term "sequence similarity", in all its grammatical forms, refers to the degree of identity or correspondence between nucleic acid or amino acid sequences that may or may not share a common evolutionary origin (see, Reeck et al., supra). However, in common usage and in the instant application, the term "homologous", when modified with an adverb such as "highly", may refer to sequence similarity and may or may not relate to a common evolutionary origin.

A nucleic acid molecule is "hybridizable" to another nucleic acid molecule, such as a cDNA, genomic DNA, or RNA, when a single stranded form of the nucleic acid molecule can anneal to the other nucleic acid molecule under the appropriate conditions of temperature and solution ionic strength (see Sambrook et al., *Molecular Cloning: A Laboratory Manual,* Second Edition (1989) Cold Spring Harbor Laboratory Press, Cold Spring Harbor, N.Y.). The conditions of temperature and ionic strength determine the "stringency" of the hybridization. For preliminary screening for homologous nucleic acids, low stringency hybridization conditions, corresponding to a $T_m$ (melting temperature) of 55° C., can be used, e.g., 5×SSC, 0.1% SDS, 0.25% milk, and no formamide; or 30% formamide, 5×SSC, 0.5% SDS). Moderate stringency hybridization conditions correspond to a higher $T_m$, e.g., 40% formamide, with 5× or 6×SSC. High stringency hybridization conditions correspond to the highest $T_m$, e.g., 50% formamide, 5×or 6×SSC. SSC is a 0.15M NaCl, 0.015M Na-citrate. Hybridization requires that the two nucleic acids contain complementary sequences, although depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the greater the value of $T_m$ for hybrids of nucleic acids having those sequences. The relative stability (corresponding to higher $T_m$) of nucleic acid hybridizations decreases in the following order: RNA:RNA, DNA:RNA, DNA:DNA. For hybrids of greater than 100 nucleotides in length, equations for calculating $T_m$ have been derived (see Sambrook et al., supra, 9.50–9.51). For hybridization with shorter nucleic acids, i.e., oligonucleotides, the position of mismatches becomes more important, and the length of the oligonucleotide determines its specificity (see Sambrook et al., supra, 11.7–11.8). A minimum length for a hybridizable nucleic acid is at least about 10 nucleotides; preferably at least about 15 nucleotides; and more preferably the length is at least about 20 nucleotides.

Unless specified, the term "standard hybridization conditions" refers to a $T_m$ of about 55° C., and utilizes conditions as set forth above. In a preferred embodiment, the $T_m$ is 60° C.; in a more preferred embodiment, the $T_m$ is 65° C. In a specific embodiment, "high stringency" refers to hybridization and/or washing conditions at 68° C. in 0.2×SSC, at 42° C. in 50% formamide, 4×SSC, or under conditions that afford levels of hybridization equivalent to those observed under either of these two conditions.

Suitable hybridization conditions for oligonucleotides (e.g., for oligonucleotide probes or primers) are typically somewhat different than for full-length nucleic acids (e.g., full-length cDNA), because of the oligonucleotides' lower melting temperature. Because the melting temperature of oligonucleotides will depend on the length of the oligonucleotide sequences involved, suitable hybridization temperatures will vary depending upon the oligoncucleotide molecules used. Exemplary temperatures may be 37° C. (for 14-base oligonucleotides), 48° C. (for 17-base oligoncucleotides), 55° C. (for 20-base oligonucleotides) and 60° C. (for 23-base oligonucleotides). Exemplary suitable hybridization conditions for oligonucleotides include washing in 6×SSC/0.05% sodium pyrophosphate, or other conditions that afford equivalent levels of hybridization.

"Polypeptide," "peptide" or "protein" are used interchangably to describe a chain of amino acids that are linked together by chemical bonds called "peptide bonds." A protein or polypeptide, including an enzyme, may be a "native" or "wild-type", meaning that it occurs in nature; or it may be a "mutant", "variant" or "modified", meaning that it has been made, altered, derived, or is in some way different or changed from a native protein or from another mutant.

"Rotamer" is defined as a set of possible conformers for each amino acid or analog side chain. See Ponder, et al., Acad. Press Inc. (London) Ltd. pp. 775–791 (1987); Dunbrack, et al., Struc. Biol. 1(5):334–340 (1994); Desmet, et al., Nature 356:539–542 (1992). A "rotamer library" is a collection of a set of possible/allowable rotametic conformations for a given set of amino acids or analogs. There are two general types of rotamer libraries: "backbone dependent" and "backbone independent." A backbone dependent rotamer library allows different rotamers depending on the position of the residue in the backbone; thus for example, certain leucine rotamers are allowed if the position is within an α helix, and different leucine rotamers are allowed if the position is not in an α-helix. A backbone independent rotamer library utilizes all rotamers of an amino acid at every position. In general, a backbone independent library is preferred in the consideration of core residues, since flexibility in the core is important. However, backbone independent libraries are computationally more expensive, and thus for surface and boundary positions, a backbone dependent library is preferred. However, either type of library can be used at any position.

"Variable residue position" herein is meant an amino acid position of the protein to be designed that is not fixed in the design method as a specific residue or rotamer, generally the wild-type residue or rotamer. It should be noted that even if a position is chosen as a variable position, it is possible that the methods of the invention will optimize the sequence in such a way as to select the wild type residue at the variable position. This generally occurs more frequently for core residues, and less regularly for surface residues. In addition, it is possible to fix residues as non-wild type amino acids as well.

"Fixed residue position" means that the residue identified in the three dimensional structure as being in a set conformation. In some embodiments, a fixed position is left in its original conformation (which may or may not correlate to a specific rotamer of the rotamer library being used). Alternatively, residues may be fixed as a non-wild type residue depending on design needs; for example, when known site-directed mutagenesis techniques have shown that a particular residue is desirable (for example, to eliminate a proteolytic site or alter the substrate specificity of an AARS), the residue may be fixed as a particular amino acid. Residues which can be fixed include, but are not limited to, structurally or biologically functional residues. For example, the anchor residues.

In certain embodiments, a fixed position may be "floated"; the amino acid or analog at that position is fixed, but different rotamers of that amino acid or analog are tested. In this embodiment, the variable residues may be at least one, or anywhere from 0.1% to 99.9% of the total number of residues. Thus, for example, it may be possible to change only a few (or one) residues, or most of the residues, with all possibilities in between.

III. Illustrative Embodiments

A. Available Sequence and Structural Information for tRNA Synthetases

An accurate description of the binding pocket is important for the computational design approach of the instant invention since it depends on the crystal structure for the protein backbone descriptions, although in many cases it is perfectly acceptable to use crystal structure of a homologous protein (for example, a homolog from a related species) or even a conserved domain to substitute the crystallographic binding pocket structure description. The crystal structure also defines the orientation of the natural substrate amino acid in the binding pocket of a synthetase, as well as the relative position of the amino acid substrate to the synthetase residues, especially those residues in and around the binding pocket. To design the binding pocket for the analogs, it is preferred that these analogs bind to the synthetase in the same orientation as the natural substrate amino acid, since this orientation may be important for the adenylation step.

The AARSs may be from any organism, including prokaryotes and eukaryotes, with enzymes from bacteria, fungi, extremeophiles such as the archebacteria, worm, insects, fish, amphibian, birds, animals (particularly mammals and particularly human) and plants all possible.

As described above, most cells make twenty different aminoacyl-tRNA synthetases, one for each type of amino acid. The crystal structures of nearly all of these different enzymes are currently available in the Brookhaven Protein Data Bank (PDB, see Bernstein et al., *J. Mol. Biol.* 112: 535–542, 1977). A list of all the AARSs with solved crystal structures as of April 2001 is available on the PDB website. For example, the crystal structure of *Thermus Aquaticus* Phenylalanyl tRNA Synthetase complexed with Phenylalanine has a resolution of 2.7 Å, and its PDB ID is 1B70.

The structure database or Molecular Modeling DataBase (MMDB) contains experimental data from crystallographic and NMR structure determinations. The data for MMDB are obtained from the Protein Data Bank (PDB). The NCBI (National Center for Biotechnology Information) has cross-linked structural data to bibliographic information, to the sequence databases, and to the NCBI taxonomy. Cn3D, the NCBI 3D structure viewer, can be used for easy interactive visualization of molecular structures from Entrez.

The Entrz 3D Domains database contains protein domains from the NCBI Conserved Domain Database (CDD). Computational biologists define conserved domains based on recurring sequence patterns or motifs. CDD currently contains domains derived from two popular collections, Smart and Pfam, plus contributions from colleagues at NCBI, such as COG. The source databases also provide descriptions and links to citations. Since conserved domains correspond to compact structural units, CDs contain links to 3D-structure via Cn3D whenever possible.

To identify conserved domains in a protein sequence, the CD-Search service employs the reverse position-specific BLAST algorithm. The query sequence is compared to a position-specific score matrix prepared from the underlying conserved domain alignment. Hits may be displayed as a pairwise alignment of the query sequence with a representative domain sequence, or as a multiple alignment. CD-Search now is run by default in parallel with protein BLAST searches. While the user waits for the BLAST queue to further process the request, the domain architecture of the query may already be studied. In addition, CDART, the Conserved Domain Architecture Retrieval Tool allows user to search for proteins with similar domain architectures. CDART uses precomputed CD-search results to quickly identify proteins with a set of domains similar to that of the query. For more details, see Marchler-Bauer et al., *Nucleic Acids Research* 31: 383–387, 2003; and Marchler-Bauer et al., *Nucleic Acids Research* 30: 281–283, 2002.

In addition, a database of known aminoacyl tRNA synthetases has been published by Maciej Szymanski, Marzanna A. Deniziak and Jan Barciszewski, in *Nucleic Acids Res.* 29:288–290, 2001 (titled "Aminoacyl-tRNA synthetases database"). A corresponding website (http://rose-.man.poznan.pl/aars/seq_main.html) provides details about all known AARSs from different species. For example, according to the database, the Isoleucyl-tRNA Synthetase for the radioresistant bacteria *Deinococcus radiodurans* (Accession No. AAF10907) has 1078 amino acids, and was published by White et al. in *Science* 286:1571–1577(1999); the Valyl-tRNA Synthetase for mouse (*Mus musculus*) has 1263 amino acids (Accession No. AAD26531), and was published by Snoek M. and van Vugt H. in *Immunogenetics* 49: 468–470(1999); and the Phenylalanyl-tRNA Synthetase sequences for human, Drosophila, *S. pombe, S. cerevisiae, Candida albicans, E. coli*, and mumerous other bacteria including *Thermus aquaticus* ssp. *thermophilus* are also available. The database was last updated in May 2000. Similar information for other newly identified AARSs can be obtained, for example, by conducting a BLAST search using any of the known sequences in the AARS database as query against the available public (such as the non-redundant database at NCBI, or "nr") or proprietory private databases.

Alternatively, in certain embodiments, if the exact crystal structure of a particular AARS is not known, but its protein sequence is similar or homologous to a known AARS sequence with a known crystal structure. In such instances, it is expected that the conformation of the AARS in question will be similar to the known crystal structure of the homologous AARS. The known structure may, therefore, be used as the structure for the AARS of interest, or more preferably, may be used to predict the structure of the AARS of interest (i.e., in "homology modeling" or "molecular modeling"). As a particular example, the Molecular Modeling Database (MMDB) described above (see, Wang et al., *Nucl. Acids Res.* 2000, 28:243–245; Marchler-Bauer et al., *Nucl. Acids Res.* 1999, 27:240–243) provides search engines that may be used to identify proteins and/or nucleic acids that are similar or homologous to a protein sequence (referred to as "neighboring" sequences in the B), including neighboring sequences whose three-dimensional structures are known. The database further provides links to the known structures along with alignment and visualization tools, such as Cn3D (developed by NCBI), RasMol, etc., whereby the homologous and parent sequences may be compared and a structure may be obtained for the parent sequence based on such sequence alignments and known structures.

The homologous AARS sequence with known 3D-structure is preferably at least about 60%, or at least about 70%, or at least about 80%, or at least about 90%, or at least about 95% identical to the AARS of interest in the active site region or the pocket region for amino acid substrate binding. Such active site or pocket site may not be continuous in the primary amino acid sequence of the AARS since distant amino acids may come together in the 3D-structure. In this case, sequence homology or identity can be calculated using, for example, the NCBI standard BLASTp programs for protein using default conditions, in regions aligned together (without insertions or deletions in either of the two sequences being compared) and including residues known to be involved in substrate amino acid binding. For example, the *Thermus Aquaticus* Phenylalanyl tRNA Synthetase alpha subunit appears to have an "insert" region from residues 156 to 165 when compared to its homologs from other species. This region can be disregarded in calculating sequence identity. Alternatively, the homologous AARS is preferably about 35%, or 40%, or 45%, or 50%, or 55% identical overall to the AARS of interest. The *E. coli* Phenylalanyl tRNA Synthetase alpha subunit is about 45% identical overall, and about 80% identical in the active site region to the *Thermus Aquaticus* Phenylalanyl tRNA Synthetase. The human Phenylalanyl tRNA Synthetase alpha subunits is about 62%, 60%, 54%, 50% identical overall to its Drosophila, worm (*C. elegans*), plant (*Arabidopsis thaliana*), yeast (*S. cerevisiae*) counterparts, respectively.

In the few cases where the structure for a particular AARS sequence may not be known or available, it is typically possible to determine the structure using routine experimental techniques (for example, X-ray crystallography and Nuclear Magnetic Resonance (NMR) spectroscopy) and without undue experimentation. See, e.g., *NMR of Macromolecules: A Practical Approach*, G. C. K. Roberts, Ed., Oxford University Press Inc., New York (1993); Ishima R, Torchia D A, "Protein Dynamics from NMR," Nat Struct Biol, 7: 740–743 (2000); Gardner K H, Kay L E, "The use of H-2, C-13, N-15 multidimensional NMR to study the structure and dynamics of proteins," Annu. Rev. Bioph. Biom., 27: 357–406 (1998); Kay L E, "NMR methods for the study of protein structure and dynamics," Biochem Cell Biol, 75: 1–15 (1997); Dayie K T, Wagner G, Lefevre J F, "Theory and practice of nuclear spin relaxation in proteins," Annu Rev Phys Chem, 47: 243–282 (1996); Wuthrich K, "NMR—This and other methods for protein and nucleic-acid structure determination," Acta Cyrstallogr. D, 51: 249–270 (1995); Kahn R, Carpentier P, Berthet-Colominas C, et al., "Feasibility and review of anomalous X-ray diffraction at long wavelengths in materials research and protein crystallography," J. Synchrotron Radiat., 7: 131–138 (2000); Oakley A J, Wilce M C J, "Macromolecular cyrstallography as a tool for investigating drug, enzyme and receptor interactions," Clin. Exp. Pharmacol. P.,27:145–151 (2000); Fourme R, Shepard W, Schiltz M, et al., "Better structures from better data through better methods: a review of developments in de novo macromolecular phasing techniques and associated instrumentation at LURE," J. Synchrotron Radiat., 6: 834–844 (1999).

Alternatively, and in less preferable embodiments, the three-dimensional structure of a AARS sequence may be calculated from the sequence itself and using ah initio molecular modeling techniques already known in the art. See e.g., Smith T F, LoConte L, Bienkowska J, et al., "Current limitations to protein threading approaches," J. Comput. Biol., 4: 217–225 (1997); Eisenhaber F, Frommel C, Argos P, "Prediction of secondary structural content of proteins from their amino acid composition alone 2. The paradox with secondary structural class," Proteins, 24: 169–179 (1996); Bohm G, "New approaches in molecular structure prediction," Biophys Chem., 59: 1–32 (1996); Fetrow J S, Bryant S H, "New programs for protein tertiary structure prediction," BioTechnol., 11: 479–484, (1993); Swindells M B, Thorton J M, "Structure prediction and modeling," Curr. Opin. Biotech., 2: 512–519 (1991); Levitt M, Gerstein M, Huang E, et al., "Protein folding: The endgame," Annu. Rev. Biochem., 66: 549–579 (1997). Eisenhaber F., Persson B., Argos P., "Protein-structure prediction—recognition of primary, secondary, and tertiary structural features from amino-acid-sequence," Crit Rev Biochem Mol, 30:1–94(1995); Xia Y, Huang E S, Levitt M, et al., "Ab initio construction of protein tertiary structures using a hierarchical approach," J. Mol. Biol., 300:171–185 (2000); Jones D T, "Protein structure prediction in the post genomicera," Curr Opin Struc Biol, 10: 371–379 (2000). Three-dimensional structures obtained from ab initio modeling are typically less reliable than structures obtained using empirical (e.g., NMR spectroscopy or X-ray crystallography) or semi-empirical (e.g., homology modeling) techniques. However, such structures will generally be of sufficient quality, although less preferred, for use in the methods of this invention.

For additional details, see section G below.

B. Binding Site Design

The protein design algorithm ORBIT, described in Dahiyat and Mayo (*Protein Sci* 5(5): 895–903, 1996; and *Science* 278: 82–87, 1997, entire contents incorporated herein by reference) and Dahiyat et al. (*J Mol Biol* 273(4): 789–96, 1997, entire content incorporated herein by reference) can be used to predict the optimal amino acid sequences of the binding pocket for binding to the different analogs. Although other similar or equivalent algorithms may also be used for the same purpose with minor modification. Selection of amino acids is performed using a very efficient DEE (Dead-End Elimination)-related search algorithm (see below) that relies on a discrete set of allowed conformations ("rotamers") for each side chain and empirical potential energy functions that are used to calculate pair-wise interactions between side chains and the between the side chains and backbone.

Surveys of protein structure database have shown that side chains exhibit marked conformational preferences, and that most side chains are limited to a small number of torsional angles. Thus, the torsional flexibility of most amino acids can be represented with a discrete set of allowed conformations called rotamers. Backbone-dependent rotameric preferences in side chains are observed in crystal structures, based on the dependency of the rotamers on the main-chain conformations. ORBIT accounts for the torsional flexibilities of side chains by providing rotamer libraries that are based on those developed by Dunbrack and Karplus (Dunbrack and Karplus, *J Mol Biol* 230(2): 543–74, 1993; Dunbrack and Karplus, *Nat Struct Biol* 1(5): 334–40 1994, entire contents of which are all incoporated herein by reference).

In our design, we would like to optimize the binding pocket of an AARS for binding to the intended analogs. In performing the optimization calculations, we would like to vary the torsional angles of the intended analogs and side chains lining the pocket simultaneously. This requires generating rotamer libraries for the analogs, since they are not included in the standard rotamer libraries. Backbone independent rotamer libraries for all the analogs are generated as described below.

Since the residues in the pocket are buried in the protein structure, we used force field parameters similar to those used in protein core design calculations. The design algorithm uses energy terms based on a force field that includes van der Waals interactions, electrostatic interactions, hydrogen bonding, and salvation effects (see Gordon et al., *Curr Opin Struct Biol* 9(4): 509–13, 1999, entire content incorporated herein by reference).

Based on the crystallographic data, residue positions in the AARS that are involved in critical interactions between the AARS and the natural amino acid backbone (the so-called "anchor residues") are identified. These residue positions are fixed in identity and rotameric conformation in the ensuing design calculation. Meanwhile, residue positions in the AARS, especially those in the binding pocket that interact with the side chain of the natural substrate amino acid (or its analog) are identified. These residue positions are potential target positions for redesign.

Design calculations (see below) are run by fixing the identity of a particular analog, and varying the target positions on the AARS described above. Certain target positions may be allowed to be any of the 20 natural amino acids, with the possible exception of proline, methionine or cysteine. These amino acids may nevertheless by be allowed at those positions if the wild-type identity of these positions are Met, Pro, or Cys. At certain other target positions, only amino acids with a certain characteristic (such as small, large, hydorphobic, hydrophilic, aromatic, etc.) are allowed based on the need of the design. It is expected that many of these target positions are buried in the core and a number of them may pack against the natural substrate in the crystal structure.

Information from othert independent studies, such as mutation analysis at a specific position which has been shown to have altered substrate specificity may also help in the design process.

As described above, the anchor residues are held fixed both in identity and conformation in all the calculations. These residues make very important electrostatic interactions with the substrate and this interaction is probably equally critical for the analogs. The aminoadenylation step is required for the incorporation of all the amino acids and hence, it may be important to make sure that the carbonyl and the amide groups of the analog zwitterions are also anchored the same way as the natural substrate at this site.

As an initial attempt, all the analog rotamers generated in the rotamer library are allowed in the calculation. As a consequence, certain rotamers selected in the structure (AARS-analog) generated may not be buried in the binding pocket, and some part or most of the analog may be solvent-exposed. A second (or more subsequent) calculation(s) can then be run allowing only those analog rotamers that would pack into the binding pocket. These are the rotamers with all possible combinations of $\chi 1$ and $\chi 2$ of the natural substrate amino acid with a maximal of $\pm 20$ of torsional angle variations, in increments of, say 1°, 2°, 3°, or 5°, etc. The structure generated in this calculation preferably will have the suitable part of the analog buried in the pocket, and is preferably completely, or almost completely superimposable with the natural substrate amino acid in the AARS crystal structure.

C. Design Calculations

The present invention utilizes an "inverse protein folding" approach directed to the quantitative design and optimization of amino acid sequences, especially the AARS with its intended analog bound in the binding pocket for its natural substrate amino acid. Similar to protein design, such approach seeks to find a sequence or set of sequences that will fold into a desired structure. These approaches can be contrasted with a "protein folding" approach which attempts to predict a structure taken by a given sequence. In a generallized approach, target AARS residue positions that is selected for redesign are determined based on the criteria described above. The side chains of any positions to be varied are then removed. The resulting structure consisting of the protein backbone (including the fixed backbone structure of the analog) and the remaining sidechains is called the template. Each variable residue position can then be optionally classified as a core residue, a surface residue, or a boundary residue. In that case, each classification defines a subset of possible amino acid residues for the position (for example, core residues generally will be selected from the set of hydrophobic residues, surface residues generally will be selected from the hydrophilic residues, and boundary residues may be either). Each amino acid residue or the analog can be represented by a discrete set of all allowed conformers of each side chain, called rotamers. Thus, to arrive at an optimal sequence for a backbone, all possible sequences of rotamers must be screened, where each backbone position can be occupied either by each amino acid in all its possible rotameric states, or a subset of amino acids, and thus a subset of rotamers. For this purpose, the analog backbone is treated as part of the AARS template.

Two sets of interactions are then calculated for each rotamer at every position: the interaction of the rotamer side chain with all or part of the backbone (the "singles" energy, also called the rotamer/template or rotamer/backbone energy), and the interaction of the rotamer side chain with all other possible rotamers at every other position or a subset of the other positions (the "doubles" energy, also called the rotamer/rotamer energy). The energy of each of these interactions is calculated through the use of a variety of scoring functions, which include the energy of van der Waal's forces, the energy of hydrogen bonding, the energy of secondary structure propensity, the energy of surface area salvation and the electrostatics (see Gordon et al., supra). Thus, the total energy of each rotamer interaction, both with the backbone and other rotamers, is calculated, and stored in a matrix form.

The discrete nature of rotamer sets allows a simple calculation of the number of rotamer sequences to be tested. A backbone of length n with m possible rotamers per position will have $m^n$ possible rotamer sequences, a number which grows exponentially with sequence length and renders the calculations either unwieldy or impossible in real time. Accordingly, to solve this combinatorial search problem, a "Dead End Elimination" (DEE) calculation is performed. The DEE calculation is based on the fact that if the worst total interaction of a first rotamer is still better than the best total interaction of a second rotamer, then the second rotamer cannot be part of the global optimum solution. Since the energies of all rotamers have already been calculated, the DEE approach only requires sums over the sequence length to test and eliminate rotamers, which speeds up the calculations considerably. DEE can be rerun comparing pairs of rotamers, or combinations of rotamers, which will eventually result in the determination of a single sequence which represents the global optimum energy.

Once the global solution has been found, a search (such as Monte Carlo search) may be done to generate a rank-ordered list of sequences in the neighborhood of the DEE solution. Starting at the DEE solution, random positions are changed to other rotamers, and the new sequence energy is calculated. If the new sequence meets the criteria for acceptance, it is used as a starting point for another jump. After a predetermined number of jumps, a rank-ordered list of sequences is generated. Typically, $10^6$ jumps (steps) are used in a Monte Carlo search.

The results may then be experimentally verified by physically generating one or more of the protein sequences followed by experimental testing. The information obtained from the testing can then be fed back into the analysis, to modify the procedure if necessary.

D. Rotamers for Target Posision Residues and Generation of Backbone-independent Rotamer Libraries for All the Analogs Once the protein backbone structure (including the analog backbone) has been selected and input, and the analog identity and variable residue positions chosen, a group of potential rotamers for each of the variable residue positions is established.

As is known in the art, each amino acid side chain has a set of possible conformers, called rotamers. See Ponder, et al., Acad. Press Inc. (London) Ltd. pp. 775–791 (1987); Dunbrack, et al., *Struc. Biol.* 1(5): 334–340 (1994); Desmet, et al., *Nature* 356: 539–542 (1992) all of which are hereby expressly incorporated by reference in their entireity. Thus, a set of discrete rotamers for every amino acid side chain is used. As described above, there are two general types of rotamer libraries: backbone dependent and backbone independent. Either type of library can be used at any position.

In addition, a preferred embodiment does a type of "fine tuning" of the rotamer library by expanding the possible χ angle values of the rotamers by plus and minus one standard deviation (±1 SD) (or more) about the mean value, in order to minimize possible errors that might arise from the discreteness of the library. This is particularly important for aromatic residues, and fairly important for hydrophobic residues, due to the increased requirements for flexibility in the core and the rigidity of aromatic rings; it is not as important for the other residues. Thus a preferred embodiment expands the χ1 and χ2 angles for all amino acids except Met, Arg and Lys. For the intended amino acid analogs, the χ1 and χ2 angles are expanded as such in their corresponding rotamers.

To roughly illustrate the numbers of rotamers, in one version of the Dunbrack & Karplus backbone-dependent rotamer library, Ala has 1 rotamer, Gly has 1 rotamer, Arg has 55 rotamers, The has 9 rotamers, Lys has 57 rotamers, Glu has 69 rotamers, Asn has 54 rotamers, Asp has 27 rotamers, Trp has 54 rotamers, Tyr has 36 rotamers, Cys has 9 rotamers, Gln has 69 rotamers, His has 54 rotamers, Val has 9 rotamers, Ile has 45 rotamers, Leu has 36 rotamers, Mat has 21 rotamers, Ser has 9 rotamers, and Phe has 36 rotamers.

In general, proline is not generally used in a target position, since it will rarely be chosen for any position, although it can be included if desired. Similarly, a preferred embodiment omits cysteine as a consideration, only to avoid potential disulfide problems, although it can be included if desired.

As will be appreciated by those in the art, other rotamer libraries with all dihedral angles staggered can be used or generated.

In a preferred embodiment, at a minimum, at least one variable position has rotamers from at least two different amino acid side chains; that is, a sequence is being optimized, rather than a structure.

In a preferred embodiment, rotamers from all of the amino acids (or all of them except cysteine, glycine and proline) are used for each variable residue position; that is, the group or set of potential rotamers at each variable position is every possible rotamer of each amino acid. This is especially preferred when the number of variable positions is not high as this type of analysis can be computationally expensive.

There is a special consideration for rotamers of amino acid analogs. For all the natural amino acids, the possible χ1 and χ2 angles are derived from database analysis. Since this is not feasible in the case of artificial amino acids or analogs, the closest approximation for χ1 and χ2 angles for the analogs are taken to be the same as those for the natural substrate amino acid. Moreover, we would like the analogs to have a conformation as close as possible, yet with certain flexibility, to the orientation of the natural substrate amino acid in the binding pocket. So allowing similar torsional angles for the analogs as of natural substrate seems logical. Preferably, as described above, both the χ1 and χ2 torsional angles for the analogs are varied to match those of the natural substrate rotamers in the standard backbone independent rotamer library. The torsional angles of the natural substrate in the crystal structure are also included in the new rotamer libraries for both the natural substrate and the analogs. Charges were assigned only to the heavy atoms of the analogs to be consistent with the way charges for the natural amino acids are represented in ORBIT.

E. Determining Conformational Energy

In certain embodiments, each variable position is classified as either a core, surface or boundary residue position, although in some cases, as explained below, the variable position may be set to glycine to minimize backbone strain.

The classification of residue positions as core, surface or boundary may be done in several ways, as will be appreciated by those in the art. In a preferred embodiment, the classification is done via a visual scan of the original protein backbone (including the bound analog) structure, including the side chains, and assigning a classification based on a subjective evaluation of one skilled in the art of protein modelling. Alternatively, a preferred embodiment utilizes an assessment of the orientation of the Cα–Cβ vectors relative to a solvent accessible surface computed using only the template Cα atoms. In a preferred embodiment, the solvent accessible surface for only the Cα atoms of the target fold is generated using the Connolly algorithm with a probe radius ranging from about 4 to about 12 Å, with from about 6 to about 10 Å being preferred, and 8 Å being particularly preferred. The Cα radius used ranges from about 1.6 Å to about 2.3 Å, with from about 1.8 to about 2.1 Å being preferred, and 1.95 Å being especially preferred. A residue is classified as a core position if a) the distance for its Cα, along its Cα–Cβ vector, to the solvent accessible surface is greater than about 4–6 Å, with greater than about 5.0 Å being especially preferred, and b) the distance for its Cβ to the nearest surface point is greater than about 1.5–3 Å, with greater than about 2.0 Å being especially preferred. The remaining residues are classified as surface positions if the sum of the distances from their Cα, along their Cα-Cβ vector, to the solvent accessible surface, plus the distance from their Cβ to the closest surface point was less than about 2.5–4 Å, with less than about 2.7 Å being especially preferred. All remaining residues are classified as boundary positions. For example, residues in the binding pocket are buried in the protein structure, force field parameters similar to those used in protein core design calculations can be used when calculating these residues.

Once each variable position is classified as either core, surface or boundary, a set of amino acid side chains, and thus a set of rotamers, is assigned to each position. That is, the set of possible amino acid side chains that the program will allow to be considered at any particular position is chosen. Subsequently, once the possible amino acid side chains are chosen, the set of rotamers that will be evaluated at a particular position can be determined. Thus, a core residue will generally be selected from the group of hydrophobic residues consisting of alanine, valine, isoleucine, leucine, phenylalanine, tyrosine, tryptophan, and methionine (in some embodiments, when the α scaling factor of the van der Waals scoring function, described below, is low, methionine is removed from the set), and the rotamer set for each core position potentially includes rotamers for these eight amino acid side chains (all the rotamers if a backbone independent library is used, and subsets if a rotamer dependent backbone is used). Similarly, surface positions are generally selected from the group of hydrophilic residues consisting of alanine, serine, threonine, aspartic acid, asparagine, glutamine, glutamic acid, arginine, lysine and histidine. The rotamer set for each surface position thus includes rotamers for these ten residues. Finally, boundary positions are generally chosen from alanine, serine, threonine, aspartic acid, asparagine, glutamine, glutamic acid, arginine, lysine histidine, valine, isoleucine, leucine, phenylalanine, tyrosine, tryptophan, and methionine. The rotamer set for each boundary position thus potentially includes every rotamer for these seventeen residues (assuming cysteine, glycine and proline are not used, although they can be).

Thus, as will be appreciated by those in the art, there is a computational benefit to classifying the residue positions, as it decreases the number of calculations. It should also be noted that there may be situations where the sets of core, boundary and surface residues are altered from those described above; for example, under some circumstances, one or more amino acids is either added or subtracted from the set of allowed amino acids. For example, some proteins which dimerize or multimerize, or have ligand binding sites, may contain hydrophobic surface residues, etc. In addition, residues that do not allow helix "capping" or the favorable interaction with an α-helix dipole may be subtracted from a set of allowed residues. This modification of amino acid groups is done on a residue by residue basis.

In a preferred embodiment, proline, cysteine and glycine are not included in the list of possible amino acid side chains, and thus the rotamers for these side chains are not used. However, in a preferred embodiment, when the variable residue position has a Φ angle (that is, the dihedral angle defined by 1) the carbonyl carbon of the preceding amino acid; 2) the nitrogen atom of the current residue; 3) the α-carbon of the current residue; and 4) the carbonyl carbon of the current residue) greater than 0°, the position is set to glycine to minimize backbone strain.

Once a three-dimensional structure has been obtained or otherwise provided for the AARS sequence as described above, a fitness value for the protein may be obtained by calculating or determining the "conformational energy" or "energy" E of the protein structure. In particular and without being limited to any particular theory or mechanism of action, sequences that have a lower (i.e., more negative) conformational energy are typically expected to be more stable and therefore more "fit" than are sequences having higher (i.e., less negative) conformation energy. Thus, the fitness of a sequence is preferably related to its negative conformational energy; i.e., F=−E.

Typically, the conformational energy is calculated ab initio from the conformation determination discussed above, and using an empirical or semi-empirical force field such as CHARM (Brooks et al., *J. Comp. Chem.* 1983, 4: 187–217; MacKerell et al., in *The Encyclopedia of Computational Chemistry*, Vol. 1:271–277, John Wiley & Sons, Chichester, 1998) AMBER (see, Cornell et al., *J. Amer Chem. Soc.* 1995, 117:5179; Woods et al., *J. Phys. Chem.* 1995, 99:3832–3846; Weiner et al., *J. Comp. Chem.* 1986, 7:230; and Weiner et al., *J. Amer. Chem. Soc.* 1984, 106:765) and DREIDING (Mayo et al., *J. Phys. Chem.* 1990, 94:8897) to name a few. These and other such force-fields comprise a number of potential scoring functions and parameters for at least approximate contributions of various interactions within a macromolecule.

The scoring functions include a van der Waals potential scoring function, a hydrogen bond potential scoring function, an atomic solvation scoring function, a secondary structure propensity scoring function and an electrostatic scoring function. As is further described below, at least one scoring function is used to score each position, although the scoring functions may differ depending on the position classification or other considerations, like favorable interaction with an α-helix dipole. As outlined below, the total energy which is used in the calculations is the sum of the energy of each scoring function used at a particular position, as is generally shown in Equation 1:

$$E_{total}=nE_{vdw}+nE_{as}+nE_{h\text{-}bonding}+nE_{ss}+nE_{elec} \quad \text{(Equation 1)}$$

In Equation 1, the total energy is the sum of the energy of the van der Waals potential ($E_{vdw}$), the energy of atomic solvation ($E_{as}$), the energy of hydrogen bonding ($E_{h\text{-}bonding}$), the energy of secondary structure ($E_{ss}$) and the energy of electrostatic interaction ($E_{elec}$). The term n is either 0 or 1, depending on whether the term is to be considered for the particular residue position, as is more fully outlined below.

In a preferred embodiment, a van der Waals' scoring function is used. As is known in the art, van der Waals' forces are the weak, non-covalent and non-ionic forces between atoms and molecules, that is, the induced dipole and electron repulsion (Pauli principle) forces. The van der Waals scoring function is based on a van der Waals potential energy. There are a number of van der Waals potential energy calculations, including a Lennard-Jones 12–6 potential with radii and well depth parameters from the Dreiding force field, Mayo et al., *J. Prot. Chem.*, 1990, expressly incorporated herein by reference, or the exponential 6 potential. Equation 2, shown below, is the preferred Lennard-Jones potential:

$$E_{vdw}=D_0\{(R_0/R)^{12}-2(R_0/R)^6\} \quad \text{(Equation 2)}$$

$R_0$ is the geometric mean of the van der Waals radii of the two atoms under consideration, and $D_0$ is the geometric mean of the well depth of the two atoms under consideration. $E_{vdw}$ and R are the energy and interatomic distance between the two atoms under consideration, as is more fully described below.

In a preferred embodiment, the van der Waals forces are scaled using a scaling factor, α. Equation 3 shows the use of α in the van der Waals Lennard-Jones potential equation:

$$E_{vdw}=D_0\{(\alpha R_0/R)^{12}-2(\alpha R_0/R)^6\} \quad \text{(Equation 3)}$$

The role of the α scaling factor is to change the importance of packing effects in the optimization and design of any particular protein. As discussed in the Examples, different values for α result in different sequences being generated by the present methods. Specifically, a reduced van der Waals steric constraint can compensate for the restrictive effect of a fixed backbone and discrete side-chain rotamers in the simulation and can allow a broader sampling of sequences compatible with a desired fold. In a preferred embodiment, α values ranging from about 0.70 to about 1.10 can be used, with α values from about 0.8 to about 1.05 being preferred, and from about 0.85 to about 1.0 being especially preferred. Specific α values which are preferred are 0.80, 0.85, 0.90, 0.95, 1.00, and 1.05.

Generally speaking, variation of the van der Waals scale factor α results in four regimes of packing specificity: regime 1 where $0.9<=\alpha<=1.05$ and packing constraints dominate the sequence selection; regime 2 where $0.8<=\alpha<0.9$ and the hydrophobic solvation potential begins to compete with packing forces; regime 3 where $\alpha<0.8$ and hydrophobic solvation dominates the design; and, regime 4 where $\alpha>1.05$ and van der Waals repulsions appear to be too severe to allow meaningful sequence selection. In particular, different α values may be used for core, surface and boundary positions, with regimes 1 and 2 being preferred for core residues, regime 1 being preferred for surface residues, and regime 1 and 2 being preferred for boundary residues.

In a preferred embodiment, the van der Waals scaling factor is used in the total energy calculations for each variable residue position, including core, surface and boundary positions.

In a preferred embodiment, an atomic salvation potential scoring function is used. As is appreciated by those in the art, solvent interactions of a protein are a significant factor in protein stability, and residue/protein hydrophobicity has been shown to be the major driving force in protein folding. Thus, there is an entropic cost to solvating hydrophobic surfaces, in addition to the potential for misfolding or aggregation. Accordingly, the burial of hydrophobic surfaces within a protein structure is beneficial to both folding and stability. Similarly, there can be a disadvantage for burying hydrophilic residues. The accessible surface area of a protein atom is generally defined as the area of the surface over which a water molecule can be placed while making van der Waals contact with this atom and not penetrating any other protein atom. Thus, in a preferred embodiment, the solvation potential is generally scored by taking the total possible exposed surface area of the moiety or two independent moieties (either a rotamer or the first rotamer and the second rotamer), which is the reference, and subtracting out the "buried" area, i.e. the area which is not solvent exposed due to interactions either with the backbone or with other rotamers. This thus gives the exposed surface area.

Alternatively, a preferred embodiment calculates the scoring function on the basis of the "buried" portion; i.e. the total possible exposed surface area is calculated, and then the calculated surface area after the interaction of the moieties is subtracted, leaving the buried surface area. A particularly preferred method does both of these calculations.

As is more fully described below, both of these methods can be done in a variety of ways. See Eisenberg et al., Nature 319:199–203 (1986); Connolly, Science 221:709–713 (1983); and Wodak, et al., Proc. Natl. Acad. Sci. USA 77(4):1736–1740 (1980), all of which are expressly incorporated herein by reference. As will be appreciated by those in the art, this solvation potential scoring function is conformation dependent, rather than conformation independent.

In a preferred embodiment, the pairwise salvation potential is implemented in two components, "singles" (rotamer/template) and "doubles" (rotamer/rotamer), as is more fully described below. For the rotamer/template buried area, the reference state is defined as the rotamer in question at residue position i with the backbone atoms only of residues i−1, i and i+1, although in some instances just i may be used. Thus, in a preferred embodiment, the salvation potential is not calculated for the interaction of each backbone atom with a particular rotamer, although more may be done as required. The area of the side chain is calculated with the backbone atoms excluding solvent but not counted in the area. The folded state is defined as the area of the rotamer in question at residue i, but now in the context of the entire template structure including non-optimized side chains, i.e. every other foxed position residue. The rotamer/template buried area is the difference between the reference and the folded states. The rotamer/rotamer reference area can be done in two ways; one by using simply the sum of the areas of the isolated rotamers; the second includes the full backbone. The folded state is the area of the two rotamers placed in their relative positions on the protein scaffold but with no template atoms present. In a preferred embodiment, the Richards definition of solvent accessible surface area (Lee and Richards, J. Mol. Biol. 55:379–400, 1971, hereby incorporated by reference) is used, with a probe radius ranging from 0.8 to 1.6 Å, with 1.4 Å being preferred, and Drieding van der Waals radii, scaled from 0.8 to 1.0. Carbon and sulfur, and all attached hydrogens, are considered nonpolar. Nitrogen and oxygen, and all attached hydrogens, are considered polar. Surface areas are calculated with the Connolly algorithm using a dot density of 10 Å-2 (Connolly, (1983) (supra), hereby incorporated by reference).

In a preferred embodiment, there is a correction for a possible overestimation of buried surface area which may exist in the calculation of the energy of interaction between two rotamers (but not the interaction of a rotamer with the backbone). Since, as is generally outlined below, rotamers are only considered in pairs, that is, a first rotamer is only compared to a second rotamer during the "doubles" calculations, this may overestimate the amount of buried surface area in locations where more than two rotamers interact, that is, where rotamers from three or more residue positions come together. Thus, a correction or scaling factor is used as outlined below. The general energy of solvation is shown in Equation 4:

$$E_{sa} = f(SA) \quad \text{(Equation 4)}$$

where $E_{sa}$ is the energy of solvation, f is a constant used to correlate surface area and energy, and SA is the surface area. This equation can be broken down, depending on which parameter is being evaluated. Thus, when the hydrophobic buried surface area is used, Equation 5 is appropriate:

$$E_{sa} = f_1(SA_{buried\ hydrophobic}) \quad \text{(Equation 5)}$$

where $f_1$ is a constant which ranges from about 10 to about 50 cal/mol/Å$^2$, with 23 or 26 cal/mol/Å$^2$ being preferred. When a penalty for hydrophilic burial is being considered, the equation is shown in Equation 6:

$$E_{sa} = f_1(SA_{buried\ hydrophobic}) + f_2(SA_{buried\ hydrophilic}) \quad \text{(Equation 6)}$$

where $f_2$ is a constant which ranges from −50 to −250 cal/mol/Å$^2$, with −86 or −100 cal/mo/Å$^2$ being preferred. Similarly, if a penalty for hydrophobic exposure is used, equation 7 or 8 may be used:

$$E_{sa} = f_1(SA_{buried\ hydrophobic}) + f_3(SA_{exposed\ hydrophobic}) \quad \text{(Equation 7)}$$

$$E_{sa} = f_1(SA_{buried\ hydrophobic}) + f_2(SA_{buried\ hydrophilic}) + f_3(SA_{exposed\ hydrophobic}) + f_4(SA_{exposed\ hydrophilic}) \quad \text{(Equation 8)}$$

In a preferred embodiment, $f_3 = -f_1$.

In one embodiment, backbone atoms are not included in the calculation of surface areas, and values of 23 cal/mol/Å$^2$ ($f_1$) and −86 cal/mol/Å$^2$ ($f_2$) are determined.

In a preferred embodiment, this overcounting problem is addressed using a scaling factor that compensates for only the portion of the expression for pairwise area that is subject to overcounting. In this embodiment, values of −26 cal/mol/Å$^2$ ($f_1$) and 100 cal/mol/Å$^2$ ($f_2$) are determined.

Atomic solvation energy is expensive, in terms of computational time and resources. Accordingly, in a preferred embodiment, the solvation energy is calculated for core and/or boundary residues, but not surface residues, with both a calculation for core and boundary residues being preferred, although any combination of the three is possible.

In a preferred embodiment, a hydrogen bond potential scoring function is used. A hydrogen bond potential is used as predicted hydrogen bonds do contribute to designed protein stability (see Stickle et al., J. Mol. Biol. 226:1143 (1992); Huyghues-Despointes et al., Biochem. 34:13267 (1995), both of which are expressly incorporated herein by reference). As outlined previously, explicit hydrogens are generated on the protein backbone structure.

In a preferred embodiment, the hydrogen bond potential consists of a distance-dependent term and an angle-dependent term, as shown in Equation 9:

$$E_{H\text{-}Bonding}=D_0\{5(R_0/R)^{12}-6(R_0/R)^{10}\}F(\theta,\phi,\psi) \quad \text{(Equation 9)}$$

where $R_0$ (2.8 Å) and $D_0$ (8 kcal/mol) are the hydrogen-bond equilibrium distance and well-depth, respectively, and R is the donor to acceptor distance. This hydrogen bond potential is based on the potential used in DREIDING with more restrictive angle-dependent terms to limit the occurrence of unfavorable hydrogen bond geometries. The angle term varies depending on the hybridization state of the donor and acceptor, as shown in Equations 10, 11, 12 and 13. Equation 10 is used for sp³ donor to sp³ acceptor; Equation 11 is used for sp³ donor to sp² acceptor, Equation 12 is used for sp² donor to sp³ acceptor, and Equation 13 is used for sp² donor to sp² acceptor:

$$F=\cos^2\theta\cos^2(\phi-109.5) \quad \text{(Equation 10)}$$

$$F=\cos^2\theta\cos^2\phi \quad \text{(Equation 11)}$$

$$F=\cos^4\theta \quad \text{(Equation 12)}$$

$$F=\cos^2\theta\cos^2(\max[\Phi,\phi]) \quad \text{(Equation 13)}$$

In Equations 10–13, θ is the donor-hydrogen-acceptor angle, Φ is the hydrogen-acceptor-base angle (the base is the atom attached to the acceptor, for example the carbonyl carbon is the base for a carbonyl oxygen acceptor), and φ is the angle between the normals of the planes defined by the six atoms attached to the sp² centers (the supplement of φ is used when φ is less than 90°). The hydrogen-bond function is only evaluated when 2.6 Å<=R<=3.2 Å, θ>90°, Φ−109.5°<90° for the sp³ donor—sp³ acceptor case, and, Φ>90° for the sp³ donor—sp² acceptor case, preferably, no switching functions are used. Template donors and acceptors that are involved in template-template hydrogen bonds are preferably not included in the donor and acceptor lists. For the purpose of exclusion, a template-template hydrogen bond is considered to exist when 2.5 Å<=R<=3.3 Å and θ>=135°.

The hydrogen-bond potential may also be combined or used with a weak coulombic term that includes a distance-dependent dielectric constant of 40R, where R is the interatomic distance. Partial atomic charges are preferably only applied to polar functional groups. A net formal charge of +1 is used for Arg and Lys and a net formal charge of −1 is used for Asp and Glu; see Gasteiger, et al., Tetrahedron 36:3219–3288 (1980); Rappe, et al., J. Phys. Chem. 95:3358–3363 (1991).

In a preferred embodiment, an explicit penalty is given for buried polar hydrogen atoms which are not hydrogen bonded to another atom. See Eisenberg, et al., (1986) (supra), hereby expressly incorporated by reference. In a preferred embodiment, this penalty for polar hydrogen burial, is from about 0 to about 3 kcal/mol, with from about 1 to about 3 being preferred and 2 kcal/mol being particularly preferred. This penalty is only applied to buried polar hydrogens not involved in hydrogen bonds. A hydrogen bond is considered to exist when $E_{HB}$ ranges from about 1 to about 4 kcal/mol, with $E_{HB}$ of less than −2 kcal/mol being preferred. In addition, in a preferred embodiment, the penalty is not applied to template hydrogens, i.e. unpaired buried hydrogens of the backbone.

In a preferred embodiment, only hydrogen bonds between a first rotamer and the backbone are scored, and rotamer-rotamer hydrogen bonds are not scored. In an alternative embodiment, hydrogen bonds between a first rotamer and the backbone are scored, and rotamer-rotamer hydrogen bonds are scaled by 0.5.

In a preferred embodiment, the hydrogen bonding scoring function is used for all positions, including core, surface and boundary positions. In alternate embodiments, the hydrogen bonding scoring function may be used on only one or two of these.

In a preferred embodiment, a secondary structure propensity scoring function is used. This is based on the specific amino acid side chain, and is conformation independent. That is, each amino acid has a certain propensity to take on a secondary structure, either α-helix or β-sheet, based on its Φ and ψ angles. See Munoz et al., Current Op. in Biotech. 6:382 (1995); Minor, et al., Nature 367:660–663 (1994); Padmanabhan, et al., Nature 344:268–270 (1990); Munoz, et al., Folding & Design 1(3):167–178 (1996); and Chakrabartty, et al., Protein Sci. 3:843 (1994), all of which are expressly incorporated herein by reference. Thus, for variable residue positions that are in recognizable secondary structure in the backbone, a secondary structure propensity scoring function is preferably used. That is, when a variable residue position is in an α-helical area of the backbone, the α-helical propensity scoring function described below is calculated. Whether or not a position is in an α-helical area of the backbone is determined as will be appreciated by those in the art, generally on the basis of Φ and ψ angles; for α-helix, Φ angles from −2 to −70 and ψ angles from −30 to −100 generally describe an α-helical area of the backbone.

Similarly, when a variable residue position is in a α-sheet backbone conformation, the β-sheet propensity scoring function is used. β-sheet backbone conformation is generally described by Φ angles from −30 to −100 and χ angles from +40 to +180. In alternate preferred embodiments, variable residue positions which are within areas of the backbone which are not assignable to either β-sheet or .alpha.-helix structure may also be subjected to secondary structure propensity calculations.

In a preferred embodiment, energies associated with secondary propensities are calculated using Equation 14:

$$E=10^{N_{ss}(\Delta G°_{aa}-\Delta G°_{ala})}-1 \quad \text{(Equation 14)}$$

In Equation 14, Eα (or Eβ) is the energy of α-helical propensity, $\Delta G°_{aa}$ is the standard free energy of helix propagation of the amino acid, and $\Delta G°_{ala}$ is the standard free energy of helix propagation of alanine used as a standard, or standard free energy of β-sheet formation of the amino acid, both of which are available in the literature (see Chakrabartty, et al., (1994) (supra), and Munoz, et al., Folding & Design 1(3):167–178 (1996)), both of which are expressly incorporated herein by reference), and $N_{ss}$ is the propensity scale factor which is set to range from 1 to 4, with 3.0 being preferred. This potential is preferably selected in order to scale the propensity energies to a similar range as the other terms in the scoring function.

In a preferred embodiment, β-sheet propensities are preferably calculated only where the i−1 and i+1 residues are also in β-sheet conformation.

In a preferred embodiment, the secondary structure propensity scoring function is used only in the energy calculations for surface variable residue positions. In alternate embodiments, the secondary structure propensity scoring function is used in the calculations for core and boundary regions as well.

In a preferred embodiment, an electrostatic scoring function is used, as shown below in Equation 15:

$$E_{elec} = qq'/\epsilon r^2 \quad \text{(Equation 15)}$$

In this Equation, q is the charge on atom 1, q' is charge on atom 2, and r is the interaction distance.

In a preferred embodiment, at least one scoring function is used for each variable residue position; in preferred embodiments, two, three or four scoring functions are used for each variable residue position.

Once the scoring functions to be used are identified for each variable position, the preferred first step in the computational analysis comprises the determination of the interaction of each possible rotamer with all or part of the remainder of the protein. That is, the energy of interaction, as measured by one or more of the scoring functions, of each possible rotamer at each variable residue position with either the backbone or other rotamers, is calculated. In a preferred embodiment, the interaction of each rotamer with the entire remainder of the protein, i.e. both the entire template and all other rotamers, is done. However, as outlined above, it is possible to only model a portion of a protein, for example a domain of a larger protein, and thus in some cases, not all of the protein need be considered.

In a preferred embodiment, the first step of the computational processing is done by calculating two sets of interactions for each rotamer at every position: the interaction of the rotamer side chain with the template or backbone (the "singles" energy), and the interaction of the rotamer side chain with all other possible rotamers at every other position (the "doubles" energy), whether that position is varied or floated. It should be understood that the backbone in this case includes both the atoms of the protein structure backbone, as well as the atoms of any fixed residues, wherein the fixed residues are defined as a particular conformation of an amino acid or analog backbone.

Thus, "singles" (rotamer/template) energies are calculated for the interaction of every possible rotamer at every variable residue position with the backbone, using some or all of the scoring functions. Thus, for the hydrogen bonding scoring function, every hydrogen bonding atom of the rotamer and every hydrogen bonding atom of the backbone is evaluated, and the $E_{HB}$ is calculated for each possible rotamer at every variable position. Similarly, for the van der Waals scoring function, every atom of the rotamer is compared to every atom of the template (generally excluding the backbone atoms of its own residue), and the $E_{vdW}$ is calculated for each possible rotamer at every variable residue position. In addition, generally no van der Waals energy is calculated if the atoms are connected by three bonds or less. For the atomic solvation scoring function, the surface of the rotamer is measured against the surface of the template, and the $E_{as}$ for each possible rotamer at every variable residue position is calculated. The secondary structure propensity scoring function is also considered as a singles energy, and thus the total singles energy may contain an $E_{ss}$ term. As will be appreciated by those in the art, many of these energy terms will be close to zero, depending on the physical distance between the rotamer and the template position; that is, the farther apart the two moieties, the lower the energy.

Accordingly, as outlined above, the total singles energy is the sum of the energy of each scoring function used at a particular position, as shown in Equation 1, wherein n is either 1 or zero, depending on whether that particular scoring function was used at the rotamer position:

$$E_{total} = nE_{vdw} + nE_{as} + nE_{h\text{-}bonding} + nE_{ss} + nE_{elec} \quad \text{(Equation 1)}$$

Once calculated, each singles $E_{total}$ for each possible rotamer is stored, such that it may be used in subsequent calculations, as outlined below.

For the calculation of "doubles" energy (rotamer/rotamer), the interaction energy of each possible rotamer is compared with every possible rotamer at all other variable residue positions. Thus, "doubles" energies are calculated for the interaction of every possible rotamer at every variable residue position with every possible rotamer at every other variable residue position, using some or all of the scoring functions. Thus, for the hydrogen bonding scoring function, every hydrogen bonding atom of the first rotamer and every hydrogen bonding atom of every possible second rotamer is evaluated, and the $E_{HB}$ is calculated for each possible rotamer pair for any two variable positions. Similarly, for the van der Waals scoring function, every atom of the first rotamer is compared to every atom of every possible second rotamer, and the $E_{vdW}$ is calculated for each possible rotamer pair at every two variable residue positions. For the atomic solvation scoring function, the surface of the first rotamer is measured against the surface of every possible second rotamer, and the $E_{as}$ for each possible rotamer pair at every two variable residue positions is calculated. The secondary structure propensity scoring function need not be run as a "doubles" energy, as it is considered as a component of the "singles" energy. As will be appreciated by those in the art, many of these double energy terms will be close to zero, depending on the physical distance between the first rotamer and the second rotamer; that is, the farther apart the two moieties, the lower the energy.

Accordingly, as outlined above, the total doubles energy is the sum of the energy of each scoring function used to evaluate every possible pair of rotamers, as shown in Equation 16, wherein n is either 1 or zero, depending on whether that particular scoring function was used at the rotamer position:

$$E_{total} = nE_{vdw} + nE_{as} + nE_{h\text{-}bonding} + E_{elec} \quad \text{(Equation 16)}$$

An example is illuminating. A first variable position, i, has three (an unrealistically low number) possible rotamers (which may be either from a single amino acid or different amino acids) which are labelled ia, ib, and ic. A second variable position, j, also has three possible rotamers, labelled jd, je, and jf. Thus, nine doubles energies ($E_{total}$) are calculated in all: $E_{total}$(ia, jd), $E_{total}$(ia, je), $Et_{total}$(ia, jf), $E_{total}$(ib, jd), $E_{total}$(ib, je), $E_{total}$(ib, Jf), $E_{total}$(ic, je) and $Et_{total}$(ic, if).

Once calculated, each doubles $E_{total}$ for each possible rotamer pair is stored, such that it may be used in subsequent calculations, as outlined below.

Once the singles and doubles energies are calculated and stored, the next step of the computational processing may occur. Generally speaking, the goal of the computational processing is to determine a set of optimized protein sequences. By "optimized protein sequence" herein is meant a sequence that best fits the mathematical equations herein. As will be appreciated by those in the art, a global optimized sequence is the one sequence that best fits Equation 1, i.e. the sequence that has the lowest energy of any possible sequence. However, there are any number of sequences that are not the global minimum but that have low energies.

In a preferred embodiment, the set comprises the globally optimal sequence in its optimal conformation, i.e. the optimum rotamer at each variable position. That is, computational processing is run until the simulation program converges on a single sequence which is the global optimum.

In a preferred embodiment, the set comprises at least two optimized protein sequences. Thus for example, the computational processing step may eliminate a number of disfavored combinations but be stopped prior to convergence, providing a set of sequences of which the global optimum is one. In addition, further computational analysis, for example using a different method, may be run on the set, to further eliminate sequences or rank them differently. Alternatively, as is more fully described below, the global optimum may be reached, and then further computational processing may occur, which generates additional optimized sequences in the neighborhood of the global optimum.

If a set comprising more than one optimized protein sequences is generated, they may be rank ordered in terms of theoretical quantitative stability, as is more fully described below.

In a preferred embodiment, the computational processing step first comprises an elimination step, sometimes referred to as "applying a cutoff", either a singles elimination or a doubles elimination. Singles elimination comprises the elimination of all rotamers with template interaction energies of greater than about 10 kcal/mol prior to any computation, with elimination energies of greater than about 15 kcal/mol being preferred and greater than about 25 kcal/mol being especially preferred. Similarly, doubles elimination is done when a rotamer has interaction energies greater than about 10 kcal/mol with all rotamers at a second residue position, with energies greater than about 15 being preferred and greater than about 25 kcal/mol being especially preferred.

In a preferred embodiment, the computational processing comprises direct determination of total sequence energies, followed by comparison of the total sequence energies to ascertain the global optimum and rank order the other possible sequences, if desired. The energy of a total sequence is shown below in Equation 17:

$$E_{total\ protein} = E(b-b) + \sum_{all\_i} E_{(ia)} + \sum_{all\_i,j\_pairs} \sum E_{(ia,ja)}$$ (Equation 17)

Thus every possible combination of rotamers may be directly evaluated by adding the backbone-backbone (sometimes referred to herein as template-template) energy ($E_{(b-b)}$ which is constant over all sequences herein since the backbone is kept constant), the singles energy for each rotamer (which has already been calculated and stored), and the doubles energy for each rotamer pair (which has already been calculated and stored). Each total sequence energy of each possible rotamer sequence can then be ranked, either from best to worst or worst to best. This is obviously computationally expensive and becomes unwieldy as the length of the protein increases.

In a preferred embodiment, the computational processing includes one or more Dead-End Elimination (DEE) computational steps. The DEE theorem is the basis for a very fast discrete search program that was designed to pack protein side chains on a fixed backbone with a known sequence. See Desmet, et al., Nature 356:539–542 (1992); Desmet, et al., The Proteins Folding Problem and Tertiary Structure Prediction, Ch. 10:1–49 (1994); Goldstein, Biophys. Jour. 66:1335–1340 (1994), all of which are incorporated herein by reference. DEE is based on the observation that if a rotamer can be eliminated from consideration at a particular position, i.e. make a determination that a particular rotamer is definitely not part of the global optimal conformation, the size of the search is reduced. This is done by comparing the worst interaction (i.e. energy or $E_{total}$) of a first rotamer at a single variable position with the best interaction of a second rotamer at the same variable position. If the worst interaction of the first rotamer is still better than the best interaction of the second rotamer, then the second rotamer cannot possibly be in the optimal conformation of the sequence. The original DEE theorem is shown in Equation 18:

$$E(ia)+\Sigma[\min(j) \text{ over } t\{E(ia,jt)\}]>E(ib)+[\max(j) \text{ over } t\{E(ib,jt)\}]$$ (Equation 18)

In Equation 18, rotamer ia is being compared to rotamer ib. The left side of the inequality is the best possible interaction energy ($E_{total}$) of ia with the rest of the protein; that is, "min over t" means find the rotamer t on position j that has the best interaction with rotamer ia. Similarly, the right side of the inequality is the worst possible (max) interaction energy of rotamer ib with the rest of the protein. If this inequality is true, then rotamer ia is Dead-Ending and can be Eliminated. The speed of DEE comes from the fact that the theorem only requires sums over the sequence length to test and eliminate rotamers.

In a preferred embodiment, a variation of DEE is performed. Goldstein DEE, based on Goldstein, (1994) (supra), hereby expressly incorporated by reference, is a variation of the DEE computation, as shown in Equation 19:

$$E(ia)-E(ib)+\Sigma[\min \text{ over } t\{E(ia,jt)-E(ib,jt)\}]>0$$ (Equation 19)

In essence, the Goldstein Equation 19 says that a first rotamer a of a particular position i (rotamer ia) will not contribute to a local energy minimum if the energy of conformation with ia can always be lowered by just changing the rotamer at that position to ib, keeping the other residues equal. If this inequality is true, then rotamer ia is Dead-Ending and can be Eliminated.

Thus, in a preferred embodiment, a first DEE computation is done where rotamers at a single variable position are compared, ("singles" DEE) to eliminate rotamers at a single position. This analysis is repeated for every variable position, to eliminate as many single rotamers as possible. In addition, every time a rotamer is eliminated from consideration through DEE, the minimum and maximum calculations of Equation 18 or 19 change, depending on which DEE variation is used, thus conceivably allowing the elimination of further rotamers. Accordingly, the singles DEE computation can be repeated until no more rotamers can be eliminated; that is, when the inequality is not longer true such that all of them could conceivably be found on the global optimum.

In a preferred embodiment, "doubles" DEE is additionally done. In doubles DEE, pairs of rotamers are evaluated; that is, a first rotamer at a first position and a second rotamer at a second position are compared to a third rotamer at the first position and a fourth rotamer at the second position, either using original or Goldstein DEE. Pairs are then flagged as nonallowable, although single rotamers cannot be eliminated, only the pair. Again, as for singles DEE, every time a rotamer pair is flagged as nonallowable, the minimum calculations of Equation 18 or 19 change (depending on which DEE variation is used) thus conceivably allowing the flagging of further rotamer pairs. Accordingly, the doubles DEE computation can be repeated until no more rotamer pairs can be flagged; that is, where the energy of rotamer pairs overlap such that all of them could conceivably be found on the global optimum.

In addition, in a preferred embodiment, rotamer pairs are initially prescreened to eliminate rotamer pairs prior to DEE.

This is done by doing relatively computationally inexpensive calculations to eliminate certain pairs up front. This may be done in several ways, as is outlined below.

In a preferred embodiment, the rotamer pair with the lowest interaction energy with the rest of the system is found. Inspection of the energy distributions in sample matrices has revealed that an $i_u j_v$ pair that dead-end eliminates a particular $i_r j_s$ pair can also eliminate other $i_r j_s$ pairs. In fact, there are often a few $i_u j_v$ pairs, which we call "magic bullets," that eliminate a significant number of $i_r j_s$ pairs. We have found that one of the most potent magic bullets is the pair for which maximum interaction energy, $t_{max}([i_u j_v])k_t$, is least. This pair is referred to as $[i_u j_v]$mb If this rotamer pair is used in the first round of doubles DEE, it tends to eliminate pairs faster.

tions of the extrema that predicted the likelihood that a matrix element would produce a dead-ending pair. Interval sizes for each pair were computed from differences of the extrema. The size of the overlap of the $i_r j_s$ and $i_u j_v$ intervals were also computed, as well as the difference between the minima and the difference between the maxima. Combinations of these quantities, as well as the lone extrema, were tested for their ability to predict the occurrence of dead-ending pairs. Because some of the maxima were very large, the quantities were also compared logarithmically.

Most of the combinations were able to predict dead-ending matrix elements to varying degrees. The best metrics were the fractional interval overlap with respect to each pair, referred to herein as $q_{rs}$ and $q_{uv}$.

$$q_{rs} = \text{interval overlap/interval}([i_r j_s]) \quad \text{(Equation 22)}$$
$$= \{\varepsilon_{max}([i_u j_v]) - \varepsilon_{min}([i_r j_s])\}/\{\varepsilon_{max}([i_r j_s]) - \varepsilon_{min}([i_r j_s])\}$$

$$q_{uv} = \text{interval overlap/interval}([i_u j_v]) \quad \text{(Equation 23)}$$
$$= \{\varepsilon_{max}([i_u j_v]) - \varepsilon_{min}([i_r j_s])\}/\{\varepsilon_{max}([i_u j_v]) - \varepsilon_{min}([i_u j_v])\}$$

Our first speed enhancement is to evaluate the first-order doubles calculation for only the matrix elements in the row corresponding to the $[i_u j_v]_{mb}$ pair. The discovery of $[i_u j_v]_{mb}$ is an $n^2$ calculation (n=the number of rotamers per position), and the application of Equation 19 to the single row of the matrix corresponding to this rotamer pair is another $n^2$ calculation, so the calculation time is small in comparison to a full first-order doubles calculation. In practice, this calculation produces a large number of dead-ending pairs, often enough to proceed to the next iteration of singles elimination without any further searching of the doubles matrix.

The magic bullet first-order calculation will also discover all dead-ending pairs that would be discovered by the Equation 18 or 19, thereby making it unnecessary. This stems from the fact that .epsilon.$_{max}$ ($[i_u ij_v]_{mb}$) must be less than or equal to any .epsilon.$_{max}$ ($[i_u j_v]$) that would successfully eliminate a pair by the Equation 18 or 19.

Since the minima and maxima of any given pair has been precalculated as outlined herein, a second speed-enhancement precalculation may be done. By comparing extrema, pairs that will not dead end can be identified and thus skipped, reducing the time of the DEE calculation. Thus, pairs that satisfy either one of the following criteria are skipped:

$$\epsilon_{min}([i_r j_s]) < \epsilon_{min}([i_u j_v]) \quad \text{(Equation 20)}$$

$$\epsilon_{min}([i_r j_s]) < \epsilon_{min}([i_u j_v]) \quad \text{(Equation 21)}$$

Because the matrix containing these calculations is symmetrical, half of its elements will satisfy the first inequality Equation 20, and half of those remaining will satisfy the other inequality Equation 21. These three quarters of the matrix need not be subjected to the evaluation of Equation 18 or 19, resulting in a theoretical speed enhancement of a factor of four.

The last DEE speed enhancement refines the search of the remaining quarter of the matrix. This is done by constructing a metric from the precomputed extrema to detect those matrix elements likely to result in a dead-ending pair.

A metric was found through analysis of matrices from different sample optimizations. We searched for combina- These values are calculated using the minima and maxima equations 24, 25, 26 and 27:

$$\varepsilon_{max}([i_r j_s]) = \varepsilon([i_r j_s]) + \sum_{k \neq i \neq j} \max(t)\varepsilon([i_r j_s], k) \quad \text{(Equation 24)}$$

$$\varepsilon_{min}([i_r j_s]) = \varepsilon([i_r j_s]) + \sum_{k \neq i \neq j} \min(t)\varepsilon([i_r j_s], k_1) \quad \text{(Equation 25)}$$

$$\varepsilon_{max}([i_u j_v]) = \varepsilon([i_u j_v]) + \sum_{k \neq i \neq j} \max(t)\varepsilon([i_u j_v], k_t) \quad \text{(Equation 26)}$$

$$\varepsilon_{min}([i_u j_v]) = \varepsilon([i_u j_v]) + \sum_{k \neq i \neq j} \min(t)\varepsilon([i_u j_v], k_1) \quad \text{(Equation 27)}$$

These metrics were selected because they yield ratios of the occurrence of dead-ending matrix elements to the total occurrence of elements that are higher than any of the other metrics tested. For example, there are very few matrix elements (~2%) for which $q_{rs}$>0.98, yet these elements produce 30–40% of all of the dead-ending pairs.

Accordingly, the first-order doubles criterion is applied only to those doubles for which $q_{rs}$>0.98 and $q_{uv}$>0.99. The sample data analyses predict that by using these two metrics, as many as half of the dead-ending elements may be found by evaluating only two to five percent of the reduced matrix.

Generally, as is more fully described below, single and double DEE, using either or both of original DEE and Goldstein DEE, is run until no further elimination is possible. Usually, convergence is not complete, and further elimination must occur to achieve convergence. This is generally done using "super residue" DEE.

In a preferred embodiment, additional DEE computation is done by the creation of "super residues" or "unification", as is generally described in Desmet, Nature 356:539–542 (1992); Desmet, et al., The Protein Folding Problem and Tertiary Structure Prediction, Ch. 10:1–49 (1994); Goldstein, et al., supra. A super residue is a combination of two or more variable residue positions which is then treated as a single residue position. The super residue is then evaluated in singles DEE, and doubles DEE, with either other residue positions or super residues. The disadvantage of super residues is that there are many more rotameric states which must be evaluated; that is, if a first variable residue position has 5 possible rotamers, and a second variable residue position has 4 possible rotamers, there are 20 possible super residue rotamers which must be evaluated. However, these super residues may be eliminated similar to singles, rather than being flagged like pairs.

The selection of which positions to combine into super residues may be done in a variety of ways. In general, random selection of positions for super residues results in inefficient elimination, but it can be done, although this is not preferred. In a preferred embodiment, the first evaluation is the selection of positions for a super residue is the number of rotamers at the position. If the position has too many rotamers, it is never unified into a super residue, as the computation becomes too unwieldy. Thus, only positions with fewer than about 100,000 rotamers are chosen, with less than about 50,000 being preferred and less than about 10,000 being especially preferred.

In a preferred embodiment, the evaluation of whether to form a super residue is done as follows. All possible rotamer pairs are ranked using Equation 28, and the rotamer pair with the highest number is chosen for unification:

$$\text{Fraction of flagged pairs}/\log^{(\text{number of super rotamers resulting from the potential unification})} \quad \text{(Equation 28)}$$

Equation 28 is looking for the pair of positions that has the highest fraction or percentage of flagged pairs but the fewest number of super rotamers. That is, the pair that gives the highest value for Equation 28 is preferably chosen. Thus, if the pair of positions that has the highest number of flagged pairs but also a very large number of super rotamers (that is, the number of rotamers at position i times the number of rotamers at position j), this pair may not be chosen (although it could) over a lower percentage of flagged pairs but fewer super rotamers.

In an alternate preferred embodiment, positions are chosen for super residues that have the highest average energy; that is, for positions i and j, the average energy of all rotamers for i and all rotamers for j is calculated, and the pair with the highest average energy is chosen as a super residue.

Super residues are made one at a time, preferably. After a super residue is chosen, the singles and doubles DEE computations are repeated where the super residue is treated as if it were a regular residue. As for singles and doubles DEE, the elimination of rotamers in the super residue DEE will alter the minimum energy calculations of DEE. Thus, repeating singles and/or doubles DEE can result in further elimination of rotamers.

In summary, the calculation and storage of the singles and doubles energies is the first step, although these may be recalculated every time. This is followed by the optional application of a cutoff, where singles or doubles energies that are too high are eliminated prior to further processing. Either or both of original singles DEE or Goldstein singles DEE may be done, with the elimination of original singles DEE being generally preferred. Once the singles DEE is run, original doubles and/or Goldstein doubles DEE is run. Super residue DEE is then generally run, either original or Goldstein super residue DEE. This preferably results in convergence at a global optimum sequence. After any step any or all of the previous steps can be rerun, in any order.

The addition of super residue DEE to the computational processing, with repetition of the previous DEE steps, generally results in convergence at the global optimum. Convergence to the global optimum is guaranteed if no cutoff applications are made, although generally a global optimum is achieved even with these steps. In a preferred embodiment, DEE is run until the global optimum sequence is found. That is, the set of optimized protein sequences contains a single member, the global optimum.

In a preferred embodiment, the various DEE steps are run until a managable number of sequences is found, i.e. no further processing is required. These sequences represent a set of optimized protein sequences, and they can be evaluated as is more fully described below. Generally, for computational purposes, a manageable number of sequences depends on the length of the sequence, but generally ranges from about 1 to about $10^{15}$ possible rotamer sequences.

Alternatively, DEE is run to a point, resulting in a set of optimized sequences (in this context, a set of remainder sequences) and then further compututational processing of a different type may be run. For example, in one embodiment, direct calculation of sequence energy as outlined above is done on the remainder possible sequences. Alternatively, a Monte Carlo search can be run.

In a preferred embodiment, the computation processing need not comprise a DEE computational step. In this embodiment, a Monte Carlo search is undertaken, as is known in the art. See Metropolis et al., J. Chem. Phys. 21:1087 (1953), hereby incorporated by reference. In this embodiment, a random sequence comprising random rotamers is chosen as a start point. In one embodiment, the variable residue positions are classified as core, boundary or surface residues and the set of available residues at each position is thus defined. Then a random sequence is generated, and a random rotamer for each amino acid is chosen. This serves as the starting sequence of the Monte Carlo search. A Monte Carlo search then makes a random jump at one position, either to a different rotamer of the same amino acid or a rotamer of a different amino acid, and then a new sequence energy ($E_{total}$ sequence) is calculated, and if the new sequence energy meets the Boltzmann criteria for acceptance, it is used as the starting point for another jump. If the Boltzmann test fails, another random jump is attempted from the previous sequence. In this way, sequences with lower and lower energies are found, to generate a set of low energy sequences.

If computational processing results in a single global optimum sequence, it is frequently preferred to generate additional sequences in the energy neighborhood of the global solution, which may be ranked. These additional sequences are also optimized protein sequences. The generation of additional optimized sequences is generally preferred so as to evaluate the differences between the theoretical and actual energies of a sequence. Generally, in a preferred embodiment, the set of sequences is at least about 75% homologous to each other, with at least about 80% homologous being preferred, at least about 85% homologous being particularly preferred, and at least about 90% being especially preferred. In some cases, homology as high as 95% to 98% is desirable. Homology in this context means sequence similarity or identity, with identity being preferred. Identical in this context means identical amino acids at corresponding positions in the two sequences which are being compared. Homology in this context includes amino acids which are identical and those which are similar (functionally equivalent). This homology will be determined using standard techniques known in the art, such as the Best Fit sequence program described by Devereux, et al., Nucl. Acid Res., 12:387–395 (1984), or the BLASTX program (Altschul, et al., J. Mol. Biol., 215:403–410 (1990)) preferably using the default settings for either. The alignment may include the introduction of gaps in the sequences to be aligned. In addition, for sequences which contain either more or fewer amino acids than an optimum sequence, it is understood that the percentage of homology will be determined based on the number of homologous amino acids in relation to the total number of amino acids. Thus, for example, homology of sequences shorter than an optimum will be determined using the number of amino acids in the shorter sequence.

Once optimized protein sequences are identified, the processing optionally proceeds to a step which entails searching the protein sequences. This processing may be implemented with a set of computer code that executes a search strategy. For example, the search may include a Monte Carlo search as described above. Starting with the global solution, random positions are changed to other rotamers allowed at the particular position, both rotamers from the same amino acid and rotamers from different amino acids. A new sequence energy ($E_{total}$ sequence) is calculated, and if the new sequence energy meets the Boltzmann criteria for acceptance, it is used as the starting point for another jump. See Metropolis et al., 1953, supra, hereby incorporated by reference. If the Boltzmann test fails, another random jump is attempted from the previous sequence. A list of the sequences and their energies is maintained during the search. After a predetermined number of jumps, the best scoring sequences may be output as a rank-ordered list. Preferably, at least about $10^6$ jumps are made, with at least about $10^7$ jumps being preferred and at least about $10^8$ jumps being particularly preferred. Preferably, at least about 100 to 1000 sequences are saved, with at least about 10,000 sequences being preferred and at least about 100,000 to 1,000,000 sequences being especially preferred. During the search, the temperature is preferably set to 1000 K.

Once the Monte Carlo search is over, all of the saved sequences are quenched by changing the temperature to 0 K, and fixing the amino acid identity at each position. Preferably, every possible rotamer jump for that particular amino acid at every position is then tried.

The computational processing results in a set of optimized protein sequences that are best suited to bind the intended amino acid analog. These optimized protein sequences may be significantly different from the wild-type sequence from which the backbone was taken. That is, each optimized protein sequence may comprises at least one residue change, or at least about 1–2%, 2–5%, 5–10% or more variant amino acids from the starting or wild-type sequence.

In a preferred embodiment, one, some or all of the optimized AARS sequences are constructed into designed proteins. Thereafter, the AARS sequences can be tested for their ability, specificity and/or efficiency to incorporate amino acid analogs into proteins in in vitro and/or in vivo assay. Generally, this can be done in one of two ways.

In a preferred embodiment, the designed AARS may be chemically synthesized as is known in the art. This is particularly useful when the designed AARSs or functional fragments are short, preferably less than 150 amino acids in length, with less than 100 amino acids being preferred, and less than 50 amino acids being particularly preferred, although as is known in the art, longer proteins can be made chemically or enzymatically.

In a preferred embodiment, particularly for longer AARS proteins or proteins for which large samples are desired, the optimized sequence is used to create a nucleic acid such as DNA which encodes the optimized sequence and which can then be cloned into a host cell and expressed. Thus, nucleic acids, and particularly DNA, can be made which encodes each optimized AARS sequence. This is done using well known procedures. The choice of codons, suitable expression vectors and suitable host cells will vary depending on a number of factors, and can be easily optimized as needed.

Once made, the designed AARS proteins are experimentally evaluated and tested for structure, altered function and stability, as necessary. This will be done as is known in the art, and will depend in part on the original protein from which the protein backbone structure was taken. Preferably, the designed AARS proteins are more stable than the known AARS protein that was used as the starting point, although in some cases, if some constraints are placed on the methods, the designed protein may be less stable. Thus, for example, it is possible to fix certain residues for altered biological activity and find the most stable sequence, but it may still be less stable than the wild type protein. Stable in this context means that the new protein retains either biological activity or conformation past the point at which the parent molecule did. Stability includes, but is not limited to, thermal stability, i.e. an increase in the temperature at which reversible or irreversible denaturing starts to occur; proteolytic stability, i.e. a decrease in the amount of protein which is irreversibly cleaved in the presence of a particular protease (including autolysis); stability to alterations in pH or oxidative conditions; chelator stability; stability to metal ions; stability to solvents such as organic solvents, surfactants, formulation chemicals; etc.

In a preferred embodiment, the modelled AARS proteins are at least about 5% more stable than the original protein, with at least about 10% being preferred and at least about 20–50% being especially preferred.

The results of the testing operations may be computationally assessed. That is, computer code may be prepared to analyze the test data with respect to any number of metrices.

At this processing juncture, if the AARS protein is selected then the protein is utilized. If a protein is not selected, the accumulated information may be used to alter the ranking scheme discussed above, and/or to repeat searching for more sequences.

In a preferred embodiment, the experimental results are used for design feedback and design optimization.

Once made, the AARS proteins of the invention find use in a wide variety of applications (see exemplary uses below), as will be appreciated by those in the art. Similarly, the methods of the present invention allow the generation of useful pharmaceutical proteins, such as analogs of known proteinaceous drugs which are more thermostable, less proteolytically sensitive, or contain other desirable changes.

In still other embodiments, an AARS sequence may be compared to one or more (preferably to a plurality of) AARS sequences to identify homologous sequences. For example, in one preferred embodiment, a particular AARS protein sequence may be aligned with a plurality of other AARS sequences (e.g., from a database of naturally occurring protein or other sequences, such as the GenBank, SWISPROT or EMBL database) to identify homologous sequences. Sequences that have a certain level of sequence similarity may also be compared. Generally, the level of sequence similarity is a threshold level or percentage of sequence homology (or sequence identity) that may be selected by a user. For example, preferred levels of sequence homology (or identity) are at least 55%, at least 60%, at least 65%, at least 70%, at least 75%, at least 80%, at least 85%, at least 90%, at least 95% or at least 99%. A variety of methods and algorithms are known in the art for aligning sequences and/or determining their levels of sequence similarity. Any of these methods and algorithms may be used in connection with this invention. Exemplary algorithms include, but are not limited to, the BLAST family of algorithms, FASTA, MEGALIGN and CLUSTAL.

Once homologous sequences have been identified and/or aligned with the parent AARS sequence, the site entropy of one or more particular residues in the parent AARS sequence may be determined or estimated from the number of homologous or aligned sequences in which the particular residue is mutated. As used to describe this invention, a homologous or aligned sequence is said to have a mutation at a particular residue if, in an alignment of the particular sequence (e.g., from the alignment algorithm used to identify a homologous sequence or sequences), the residue in the homologous sequence which that aligns with the particular residue in the parent sequence is different (i.e., has a different identity) from the particular residue. The probabilities required to determine the site entropy can be calculated by the relative number of times each amino acid appears at each residue in the alignment.

F. RBIAS—for Enhancing Protein-substrate Interactions

All the mutant sequences predicted in the above calculation gear towards making enough space in the binding pocket for accommodating the analog, but besides van der Waals interactions, there may be little or no specific interaction between the analog and the synthetase.

In order to design specificity into the AARS-analog interaction, the program RBIAS or its equivalent may be used to enhance the interactions between the analog and the protein positions. This is done by scaling up the pair-wise energies between the analog and the amino acids allowed at the design positions on the protein in the energy calculations. In an optimization calculation where the protein-analog interactions are scaled up compared to the intra-protein interactions, sequence selection will be biased toward selecting amino acids to be those that have favorable interaction with the analog.

Multiple calculations can be performed by scaling up the analog-protein interactions by factors of, for example, 2.0 to 20.0, in increments of, for example, 0.5, 1.5, or preferably 2.0. Certain scale factors are expected to generate certain interesting mutations, which, for example, would makes a hydrogen bond with a group of the analog. The interaction between the analog and the AARS in the sequence may be enhanced by a value less than the value lost due to destabilization of the overall structure, as indicated by the total energy. Moreover, polar groups in the core, especially those that are not involved in a salt-bridge or a hydrogen bond may significantly destabilize proteins. Therefore, only some amount of overall protein stability can be traded off in order to gain specificity between the protein and the analog. However, based on these considerations, certain candidate sequence mutations or combinations thereof will emerge, and these potential sequence changes are good candidates for further testing, such as constructing the mutant protein using standard recombinant DNA technology, and testing these mutants in vitro and/or in vivo in order to assess the ability, specificity, and/or efficiency of these mutants to incorporate the analogs into protein products. Preferably, the re-designed AARS is specific for the analog it is intended to charge onto tRNA, and cannot charge natural amino acids to tRNA.

G. Methods for Predicting 3D Structure Based on Sequence Homology

For AARS proteins that have not been crystallized or been the focus of other structural determinations, a computer-generated molecular model of the AARS and its binding site can nevertheless be generated using any of a number of techniques available in the art. For example, the Cα-carbon positions of the target AARS sequence can be mapped to a particular coordinate pattern of an AARS enzyme ("known AARS") having a similar sequence and deduced structure using homology modeling techniques, and the structure of the target protein and velocities of each atom calculated at a simulation temperature (To) at which a docking simulation with an amino acid analog is to be determined. Typically, such a protocol involves primarily the prediction of side-chain conformations in the modeled target AARS protein, while assuming a main-chain trace taken from a tertiary structure, such as provided by the known AARS protein. Computer programs for performing energy minimization routines are commonly used to generate molecular models. For example, both the CHARMM (Brooks et al. (1983) *J Comput Chem* 4:187–217) and AMBER (Weiner et al (1981) *J. Comput. Chem.* 106: 765) algorithms handle all of the molecular system setup, force field calculation, and analysis (see also, Eisenfield et al. (1991) *Am J Physiol* 261: C376–386; Lybrand (1991) *J Pharm Belg* 46:49–54; Froimowitz (1990) *Biotechniques* 8:640–644; Burbam et al. (1990) *Proteins* 7:99–111; Pedersen (1985) *Environ Health Perspect* 61:185–190; and Kini et al. (1991) *J Biomol Struct Dyn* 9:475–488). At the heart of these programs is a set of subroutines that, given the position of every atom in the model, calculate the total potential energy of the system and the force on each atom. These programs may utilize a starting set of atomic coordinates, the parameters for the various terms of the potential energy function, and a description of the molecular topology (the covalent structure). Common features of such molecular modeling methods include: provisions for handling hydrogen bonds and other constraint forces; the use of periodic boundary conditions; and provisions for occasionally adjusting positions, velocities, or other parameters in order to maintain or change temperature, pressure, volume, forces of constraint, or other externally controlled conditions.

Most conventional energy minimization methods use the input coordinate data and the fact that the potential energy function is an explicit, differentiable function of Cartesian coordinates, to calculate the potential energy and its gradient (which gives the force on each atom) for any set of atomic positions. This information can be used to generate a new set of coordinates in an effort to reduce the total potential energy and, by repeating this process over and over, to optimize the molecular structure under a given set of external conditions. These energy minimization methods are routinely applied to molecules similar to the subject AARS proteins.

In general, energy minimization methods can be carried out for a given temperature, Ti, which may be different than the docking simulation temperature, To. Upon energy minimization of the molecule at Ti, coordinates and velocities of all the atoms in the system are computed. Additionally, the normal modes of the system are calculated. It will be appreciated by those skilled in the art that each normal mode is a collective, periodic motion, with all parts of the system moving in phase with each other, and that the motion of the molecule is the superposition of all normal modes. For a given temperature, the mean square amplitude of motion in a particular mode is inversely proportional to the effective force constant for that mode, so that the motion of the molecule will often be dominated by the low frequency vibrations.

After the molecular model has been energy minimized at Ti, the system is "heated" or "cooled" to the simulation temperature, To, by carrying out an equilibration run where the velocities of the atoms are scaled in a step-wise manner until the desired temperature, To, is reached. The system is further equilibrated for a specified period of time until certain properties of the system, such as average kinetic energy, remain constant. The coordinates and velocities of each atom are then obtained from the equilibrated system.

Further energy minimization routines can also be carried out. For example, a second class of methods involves calculating approximate solutions to the constrained EOM for the protein. These methods use an iterative approach to solve for the Lagrange multipliers and, typically, only need a few iterations if the corrections required are small. The most popular method of this type, SHAKE (Ryckaert et al. (1977) *J Comput Phys* 23:327; and Van Gunsteren et al. (1977) *Mol Phys* 34:1311) is easy to implement and scales as O(N) as the number of constraints increases. Therefore, the method is applicable to macromolecules such as AARS proteins. An alternative method, RATTLE (Anderson (1983) *J Comput Phys* 52:24) is based on the velocity version of the Verlet algorithm. Like SHAKE, RATTLE is an iterative algorithm and can be used to energy minimize the model of a subject AARS protein.

H. Alternative Methods

In other embodiments, rather than holding the identity of the amino acid analog constant and varying the AARS structure (by modeling several different mutant structures), the subject method is carried out using the molecular model(s) for a single AARS mutant (e.g., in which one more non-anchor amino acid residues are changed) and sampling a variety of different amino acid analogs or potential fragments thereof, to identify analogs which are likely to interact with, and be substrates for the mutant AARS enzyme. This approach can make use of coordinate libraries for amino acid analogs (including rotamer variants) or libraries of functional groups and spacers that can be joined to form the sidechain of an amino acid analog.

Using such approaches as described above, e.g., homology modeling, a coordinate set for the binding site for the mutant AARS can be derived.

There are a variety of computational methods that can be readily adapted for identifying the structure of amino acid analogs that would have appropriate steric and electronic properties to interact with the substrate binding site of an AARS mutant. See, for example, Cohen et al. (1990) *J. Med. Cam.* 33: 883–894; Kuntz et al. (1982) *J. Mol. Biol* 161: 269–288; DesJarlais (1988) *J. Med. Cam.* 31: 722–729; Bartlett et al. (1989) (*Spec. Publ., Roy. Soc. Chem.*) 78: 182–196; Goodford et al. (1985) *J. Med. Cam.* 28: 849–857; DesJarlais et al. *J. Med. Cam.* 29: 2149–2153). Directed methods generally fall into two categories: (1) design by analogy in which 3-D structures of known molecules (such as from a crystallographic database) are docked to the AARS binding site structure and scored for goodness-of-fit; and (2) de novo design, in which the amino acid analog model is constructed piece-wise in the AARS binding site. The latter approach, in particular, can facilitate the development of novel molecules, uniquely designed to bind to the subject AARS mutant binding site.

In an illustrative embodiment, the design of potential amino acid analogs that may function with a particular AARS mutant begins from the general perspective of shape complimentary for the substrate binding site of the enzyme, and a search algorithm is employed which is capable of scanning a database of small molecules of known three-dimensional structure for candidates which fit geometrically into the substrate binding site. Such libraries can be general small molecule libraries, or can be libraries directed to amino acid analogs or small molecules which can be used to create amino acid analogs. It is not expected that the molecules found in the shape search will necessarily be leads themselves, since no evaluation of chemical interaction necessarily be made during the initial search. Rather, it is anticipated that such candidates might act as the framework for further design, providing molecular skeletons to which appropriate atomic replacements can be made. Of course, the chemical complimentary of these molecules can be evaluated, but it is expected that atom types will be changed to maximize the electrostatic, hydrogen bonding, and hydrophobic interactions with the substrate binding site. Most algorithms of this type provide a method for finding a wide assortment of chemical structures that may be complementary to the shape of the AARS substrate binding site.

For instance, each of a set of small molecules from a particular data-base, such as the Cambridge Crystallographic Data Bank (CCDB) (Allen et al. (1973) *J. Chem. Doc.* 13: 119), is individually docked to the binding site of the AARS mutant in a number of geometrically permissible orientations with use of a docking algorithm. In a preferred embodiment, a set of computer algorithms called DOCK, can be used to characterize the shape of invaginations and grooves that form the binding site. See, for example, Kuntz et al. (1982) *J. Mol. Biol* 161: 269–288. The program can also search a database of small molecules for templates whose shapes are complementary to particular binding site of the AARS mutant. Exemplary algorithms that can be adapted for this purpose are described in, for example, DesJarlais et al. (1988) *J Med Chem* 31:722–729.

The orientations are evaluated for goodness-of-fit and the best are kept for further examination using molecular mechanics programs, such as AMBER or CHARMM. Such algorithms have previously proven successful in finding a variety of molecules that are complementary in shape to a given binding site of a receptor or enzyme, and have been shown to have several attractive features. First, such algorithms can retrieve a remarkable diversity of molecular architectures. Second, the best structures have, in previous applications to other proteins, demonstrated impressive shape complementarity over an extended surface area. Third, the overall approach appears to be quite robust with respect to small uncertainties in positioning of the candidate atoms.

In certain embodiments, the subject method can utilize an algorithm described by Goodford (1985, *J Med Chem* 28:849–857) and Boobbyer et al. (1989, *J Med Chem* 32:1083–1094). Those papers describe a computer program (GRID) which seeks to determine regions of high affinity for different chemical groups (termed probes) on the molecular surface of the binding site. GRID hence provides a tool for suggesting modifications to known ligands that might enhance binding. It may be anticipated that some of the sites discerned by GRID as regions of high affinity correspond to "pharmacophoric patterns" determined inferentially from a series of known ligands. As used herein, a pharmacophoric pattern is a geometric arrangement of features of the anticipated amino acid analog that is believed to be important for binding. Goodsell and Olson (1990, *Proteins: Struct Funct Genet* 8:195–202) have used the Metropolis (simulated annealing) algorithm to dock a single known ligand into a target protein, and their approach can be adapted for identifying suitable amino acid analogs for docking with the AARS binding site. This algorithm can allow torsional flexibility in the amino acid sidechain and use GRID interaction energy maps as rapid lookup tables for computing approximate interaction energies.

Yet a further embodiment of the present invention utilizes a computer algorithm such as CLIX which searches such databases as CCDB for small molecules which can be oriented in the substrate binding site of the AARS in a way that is both sterically acceptable and has a high likelihood of achieving favorable chemical interactions between the candidate molecule and the surrounding amino acid residues. The method is based on characterizing the substrate binding site in terms of an ensemble of favorable binding positions for different chemical groups and then searching for orientations of the candidate molecules that cause maximum spatial coincidence of individual candidate chemical groups with members of the ensemble. The current availability of computer power dictates that a computer-based search for novel ligands follows a breadth-first strategy. A breadth-first strategy aims to reduce progressively the size of the potential candidate search space by the application of increasingly stringent criteria, as opposed to a depth-first strategy wherein a maximally detailed analysis of one candidate is performed before proceeding to the next. CLIX conforms to this strategy in that its analysis of binding is rudimentary—it seeks to satisfy the necessary conditions of steric fit and of having individual groups in "correct" places for bonding, without imposing the sufficient condition that favorable bonding interactions actually occur. A ranked "shortlist" of molecules, in their favored orientations, is produced which can then be examined on a molecule-by-molecule basis, using computer graphics and more sophisticated molecular modeling techniques. CLIX is also capable of suggesting changes to the substituent chemical groups of the candidate molecules that might enhance binding. Again, the starting library can be of amino acid analogs or of molecules which can be used to generate the sidechain of an amino acid analog.

The algorithmic details of CLIX is described in Lawerence et al. (1992) *Proteins* 12:31–41, and the CLIX algorithm can be summarized as follows. The GRID program is used to determine discrete favorable interaction positions (termed target sites) in the binding site of the AARS protein for a wide variety of representative chemical groups. For each candidate ligand in the CCDB an exhaustive attempt is made to make coincident, in a spatial sense in the binding site of the protein, a pair of the candidate's substituent chemical groups with a pair of corresponding favorable interaction sites proposed by GRID. All possible combinations of pairs of ligand groups with pairs of GRID sites are considered during this procedure. Upon locating such coincidence, the program rotates the candidate ligand about the two pairs of groups and checks for steric hindrance and coincidence of other candidate atomic groups with appropriate target sites. Particular candidate/orientation combinations that are good geometric fits in the binding site and show sufficient coincidence of atomic groups with GRID sites are retained.

Consistent with the breadth-first strategy, this approach involves simplifying assumptions. Rigid protein and small molecule geometry is maintained throughout. As a first approximation rigid geometry is acceptable as the energy minimized coordinates of the binding site of the AARS mutant, describe an energy minimum for the molecule, albeit a local one.

A further assumption implicit in CLIX is that the potential ligand, when introduced into the substrate binding site of the AARS mutant, does not induce change in the protein's stereochemistry or partial charge distribution and so alter the basis on which the GRID interaction energy maps were computed. It must also be stressed that the interaction sites predicted by GRID are used in a positional and type sense only, i.e., when a candidate atomic group is placed at a site predicted as favorable by GRID, no check is made to ensure that the bond geometry, the state of protonation, or the partial charge distribution favors a strong interaction between the protein and that group. Such detailed analysis should form part of more advanced modeling of candidates identified in the CLIX shortlist.

Yet another embodiment of a computer-assisted molecular design method for identifying amino acid analogs that may be utilized by a predetermined AARS mutant comprises the de novo synthesis of potential inhibitors by algorithmic connection of small molecular fragments that will exhibit the desired structural and electrostatic complementarity with the substrate binding site of the enzyme. The methodology employs a large template set of small molecules with are iteratively pieced together in a model of the AARS' substrate binding site. Each stage of ligand growth is evaluated according to a molecular mechanics-based energy function, which considers van der Waals and coulombic interactions, internal strain energy of the lengthening ligand, and desolvation of both ligand and enzyme. The search space can be managed by use of a data tree which is kept under control by pruning according to the binding criteria.

In yet another embodiment, potential amino acid analogs can be determined using a method based on an energy minimization-quenched molecular dynamics algorithm for determining energetically favorable positions of functional groups in the substrate binding site of a mutant AARS enzyme. The method can aid in the design of molecules that incorporate such functional groups by modification of known amino acid and amino acid analogs or through de novo synthesis.

For example, the multiple copy simultaneous search method (MCSS) described by Miranker et al. (1991) *Proteins* 11: 29–34 can be adapted for use in the subject method. To determine and characterize a local minima of a functional group in the force field of the protein, multiple copies of selected functional groups are first distributed in a binding site of interest on the AARS protein. Energy minimization of these copies by molecular mechanics or quenched dynamics yields the distinct local minima. The neighborhood of these minima can then be explored by a grid search or by constrained minimization. In one embodiment, the MCSS method uses the classical time dependent Hartee (TDH) approximation to simultaneously minimize or quench many identical groups in the force field of the protein.

Implementation of the MCSS algorithm requires a choice of functional groups and a molecular mechanics model for each of them. Groups must be simple enough to be easily characterized and manipulated (3–6 atoms, few or no dihedral degrees of freedom), yet complex enough to approximate the steric and electrostatic interactions that the functional group would have in substrate binding to the site of the AARS protein. A preferred set is, for example, one in which most organic molecules can be described as a collection of such groups (*Patai's Guide to the Chemistry of Functional Groups,* ed. S. Patai (New York: John Wiley, and Sons, (1989)). This includes fragments such as acetonitrile, methanol, acetate, methyl ammonium, dimethyl ether, methane, and acetaldehyde.

Determination of the local energy minima in the binding site requires that many starting positions be sampled. This can be achieved by distributing, for example, 1,000–5,000 groups at random inside a sphere centered on the binding site; only the space not occupied by the protein needs to be considered. If the interaction energy of a particular group at a certain location with the protein is more positive than a given cut-off (e.g. 5.0 kcal/mole) the group is discarded from that site. Given the set of starting positions, all the fragments are minimized simultaneously by use of the TDH approximation (Elber et al. (1990) *J Am Chem Soc* 112: 9161–9175). In this method, the forces on each fragment consist of its internal forces and those due to the protein. The essential element of this method is that the interactions between the fragments are omitted and the forces on the protein are normalized to those due to a single fragment. In this way simultaneous minimization or dynamics of any number of functional groups in the field of a single protein can be performed.

Minimization is performed successively on subsets of, e.g. 100, of the randomly placed groups. After a certain number of step intervals, such as 1,000 intervals, the results can be examined to eliminate groups converging to the same minimum. This process is repeated until minimization is complete (e.g. RMS gradient of 0.01 kcal/mole/Å). Thus the resulting energy minimized set of molecules comprises what amounts to a set of disconnected fragments in three dimensions representing potential sidechains for amino acid analogs.

The next step then is to connect the pieces with spacers assembled from small chemical entities (atoms, chains, or ring moieties) to form amino acid analogs, e.g., each of the disconnected can be linked in space to generate a single molecule using such computer programs as, for example, NEWLEAD (Tschinke et al. (1993) *J Med Chem* 36: 3863, 3870). The procedure adopted by NEWLEAD executes the following sequence of commands (1) connect two isolated moieties, (2) retain the intermediate solutions for further processing, (3) repeat the above steps for each of the intermediate solutions until no disconnected units are found, and (4) output the final solutions, each of which is single molecule. Such a program can use for example, three types of spacers: library spacers, single-atom spacers, and fuse-ring spacers. The library spacers are optimized structures of small molecules such as ethylene, benzene and methylamide. The output produced by programs such as NEWLEAD consist of a set of molecules containing the original fragments now connected by spacers. The atoms belonging to the input fragments maintain their original orientations in space. The molecules are chemically plausible because of the simple makeup of the spacers and functional groups, and energetically acceptable because of the rejection of solutions with van-der Waals radii violations.

In addition, the order in which the steps of the present method are performed is purely illustrative in nature. In fact, the steps can be performed in any order or in parallel, unless otherwise indicated by the present disclosure.

Furthermore, the method of the present invention may be performed in either hardware, software, or any combination thereof, as those terms are currently known in the art. In particular, the present method may be carried out by software, firmware, or microcode operating on a computer or computers of any type. Additionally, software embodying the present invention may comprise computer instructions in any form (e.g., source code, object code, interpreted code, etc.) stored in any computer-readable medium (e.g., ROM, RAM, magnetic media, punched tape or card, compact disc (CD) in any form, DVD, etc.). Furthermore, such software may also be in the form of a computer data signal embodied in a carrier wave, such as that found within the well-known Web pages transferred among devices connected to the Internet. Accordingly, the present invention is not limited to any particular platform, unless specifically stated otherwise in the present disclosure.

Examplery computer hardware means suitable for carrying out the invention can be a Silicon Graphics Power Challenge server with 10 R10000 processors running in parallel. Suitable software development environment includes CERIUS2 by Biosym/Molecular Simulations (San Diego, Calif.), or other equivalents.

While particular embodiments of the present invention have been shown and described, it will be apparent to those skilled in the art that changes and modifications may be made without departing from this invention in its broader aspect and, therefore, the appended claims are to encompass within their scope all such changes and modifications as fall within the true spirit of this invention.

I. Exemplary Uses

To date, over 100 noncoded amino acids (all ribosomally acceptable) have been reportedly introduced into proteins using other methods (see, for example, Schultz et al., *J. Am. Chem. Soc.*, 103: 1563–1567, 1981; Hinsberg et al., *J. Am. Chem. Soc.*, 104: 766–773, 1982; Pollack et al., *Science*, 242: 1038–1040, 1988; Nowak et al., *Science*, 268: 439–442, 1995) all these analogs may be used for designing suitable AARSs that can efficiently incorporate these analogs into protein products. In general, the re-designed AARSs (mutant AARSs) of the instant invention can be used to incorporate amino acid analogs into protein products either in vitro or in vivo.

The ration of natural/analog amino acids may be controlled so that the degree of incorporation may be adjusted. In a preferred embodiment, 100% of one or more of the natural amio acids (such as Phe) may be depleted so that only its analogs are incorporated.

In another preferred embodiment, two or more analogs may be used in the same in vitro or in vivo translation system. These analogs can be analogs of the same amino acid (for example, different Phe analogs), or different amino acids (for example, analogs of Phe and Tyr, respectively).

For in vitro use, one or more AARSs of the instant invention can be recombinantly produced and supplied to any the available in vitro translation systems (such as the commercially available Wheat Germ Lysate-based PROTEINscript-PRO™, Ambion's *E. coli* system for coupled in vitro transcription/translation; or the rabbit reticulocyte lysate-based Retic Lysate IVT™ Kit from Ambion). Optionally, the in vitro translation system can be selectively depeleted of one or more natural AARSs (by, for example, immunodepletion using immobilized antibodies against natural AARS) and/or natural amino acids so that enhanced incorporation of the analog can be achieved. Alternatively, nucleic acids encoding the re-designed AARSs may be supplied in place of recombinantly produced AARSs. The in vitro translation system is also supplied with the analogs to be incorporated into mature protein products.

Although in vitro protein synthesis usually cannot be carried out on the same scale as in vivo synthesis, in vitro methods can yield hundreds of micrograms of purified protein containing amino acid analogs. Such proteins have been produced in quantities sufficient for their characterization using circular dichroism (CD), nuclear magnetic resonance (NMR) spectrometry, and X-ray crystallography. This methodology can also be used to investigate the role of hydrophobicity, packing, side chain entropy and hydrogen bonding in determining protein stability and folding. It can also be used to probe catalytic mechanism, signal transduction and electron transfer in proteins. In addition, the properties of proteins can be modified using this methodology. For example, photocaged proteins can be generated that can be activated by photolysis, and novel chemical handles have been introduced into proteins for the site specific incorporation of optical and other spectroscopic probes.

The development of a general approach for the incorporation of amino acid analogs into proteins in vivo, directly from the growth media, would greatly enhance the power of unnatural amino acid mutagenesis. For example, the ability to synthesize large quantities of proteins containing heavy atoms would facilitate protein structure determination, and the ability to site-specifically substitute fluorophores or photocleavable groups into proteins in living cells would provide powerful tools for studying protein function in vivo. Alternatively, one might be able to enhance the properties of proteins by providing building blocks with new functional groups, such as a keto-containing amino acid.

For in vivo use, one or more AARS of the instant invention can be supplied to a host cell (prokaryotic or eukaryotic) as genetic materials, such as coding sequences on plasmids or viral vectors, which may optionally integrate into the host genome and constitutively or inducibly express the re-designed AARSs. A heterologous or endogenous protein of interest can be expressed in such a host cell, at the presence of supplied amino acid analogs. The protein products can then be purified using any art-recognized protein purification techniques, or techniques specially designed for the protein of interest.

The above described uses are merely a few possible means for generating a transcript which encodes a polypeptide. In general, any means known in the art for generating transcripts can be employed to synthesize proteins with amino acid analogs. For example, any in vitro transcription system or coupled transcription/translation systems can be used for generate a transcript of interest, which then serves as a template for protein synthesis. Alternatively, any cell, engineered cell/cell line, or functional components (lysates, membrane fractions, etc.) that is capable of expressing proteins from genetic materials can be used to generate a transcript. These means for generating a transcript will typically include such components as RNA polymerase (T7, SP6, etc.) and co-factors, nucleotides (ATP, CTP, GTP, UTP), necessary transcription factors, and appropriate buffer conditions, as well as at least one suitable DNA template, but other components may also added for optimized reaction condition. A skilled artisan would readily envision other embodiments similar to those described herein.

IV. EXAMPLES

We have developed computational methods to predict sequence changes in aminoacyl tRNA synthetases that enable them to bind to novel amino acid analogs. A rotamer library for the artificial amino acid is built by varying its torsional angles to create rotamers that would fit in the binding pocket for the natural substrate. The geometric orientation of the backbone of the amino acid analog is specified by the crystallographic orientation of the backbone of the natural substrate in the crystal structure. Amino acids in the binding pocket of the synthetase that interact with the side chain on the analog are allowed to vary in identity and rotameric conformation in the subsequent protein design calculations.

We have also developed a computational method to enhance the interactions between the substrate and the protein positions. This is done by scaling up the pair-wise energies between the substrate and the amino acids allowed at the design positions on the protein in the energy calculations. In an optimization calculation where the protein-substrate interactions are scaled up compared to the intra-protein interactions, sequence selection is biased toward selecting amino acids to be those that have favorable interaction with the substrate.

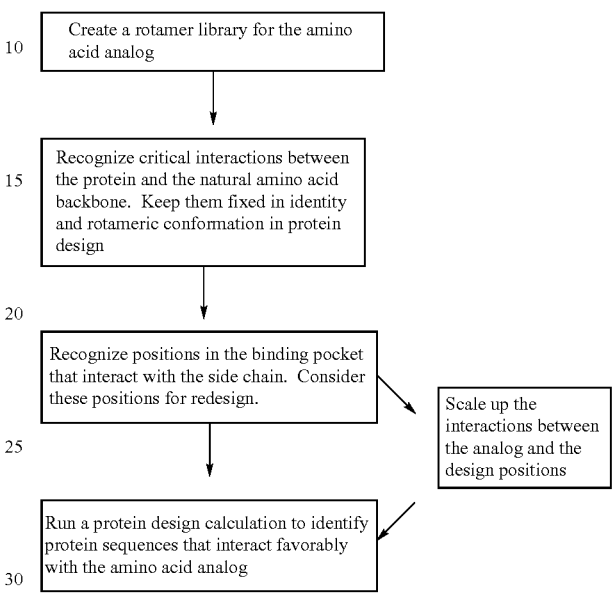

The details of the invention are described below by means of examples of increasing detail and specificity. These examples are provided only to illustrate preferred embodiments of the invention. However, the invention is not limited to the particular embodiments, and many modifications and variations of the invention will be apparent to those skilled in the art. Such modifications and variations are therefore also considered part of the invention.

In the following example, we have used Phenylalanyl tRNA synthetase (PheRS) as model to test the techniques. We have designed a new mutant form of E. Coli tRNA synthetase that allows efficient in vivo incorporation of aryl ketone functionality in recombinant proteins.

I. A Designed Phenylalanyl-tRNA Synthetase Variant Allows Efficient In Vivo Incorporation of Non-natural Amino Acids (e.g. with Aryl Ketone Functionality) into Proteins We have previously exploited the ability of auxotrophic Escherichia coli strains to effect efficient incorporation of amino acid analogues into proteins in a multi-site fashion. The method is simple and produces high protein yields, and incorporation of the analogue at multiple sites offers significant advantages with respect to control of protein properties such as thermal and chemical stability.[2]

Figure 2:
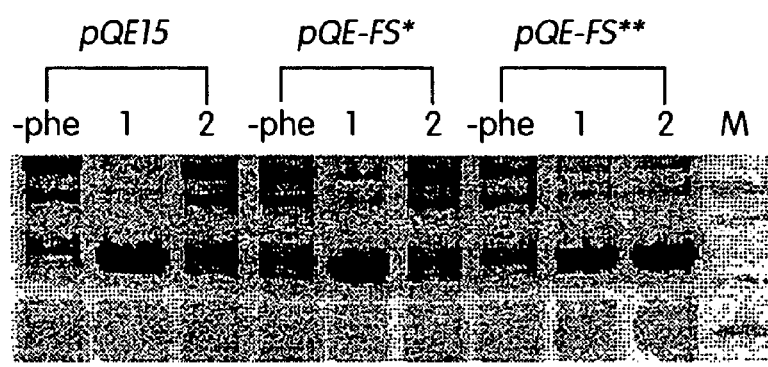
FIG. 2 SDS-PAGE of cell lysates of 4 hr post-induction with 1 mM IPTG. Expression plasmids and amino acid supplements are indicated. Concentration of 1 (Phe)=20 mg/L; 2 (p-AcetylPhe)=250 mg/L. Lane M: molecular weight marker (35.5, 31, 21.5, and 14.4 kDa).

In this study, we report a computationally-designed variant of the E. coli phenylalanyl-tRNA synthetase (ePheRS), which allows efficient in vivo incorporation of aryl ketone functionality into proteins. In 1991, Kast and coworkers[3] introduced a variant of ePheRS (termed ePheRS*), which bears an Ala294Gly (A294G) mutation in the α-subunit and which thereby acquires relaxed substrate specificity. We have recently shown that over-expression of ePheRS* can be exploited to effect efficient incorporation of p-bromo-, p-iodo-, p-ethynyl-, p-cyano- and p-azidophenylalanines into recombinant proteins in *E. coli* hosts.[4,5] But similar experiments with p-acetylphenylalanine (2 in FIG. 1) failed; even in a host in which ePheRS* was over-expressed, Phe-depleted cultures supplemented with 2 did not produce substantial yields of protein (FIG. 2).

Our interest in 2 arises from the chemical versatility of the side-chain ketone function, which can be chemoselectively ligated with hydrazide, hydroxylamino, and thiosemicarbazide reagents under physiological conditions.[6,7] Cornish and coworkers have accomplished site-specific incorporation of ketone functionality into recombinant proteins via in vitro translation; however, we are unaware of previous reports of in vivo methods of introducing ketone functionality into recombinant proteins.

It is desirable to identify/engineer additional ePheRS mutants that would allow efficient incorporation of 2 into recombinant proteins in vivo. The technique can also be used to introduce other unnatural substrates/substrate analogs that can not be efficiently incorporated into recombinant proteins in vivo using natural RNA synthetases or existing mutant RNA synthetases with relaxed substrate specificity.

The crystal structure of *Thermus thermophilus* PheRS (tPheRS) complexed with 1 is available[9] and there is 43% overall sequence identity between ePheRS and /PheRS; sequence identity in the identified active site region is 80%. We therefore employed a previously described protein design algorithm[10] to identify potentially useful mutants of tPheRS, with the intention to prepare and evaluate the corresponding mutant forms of ePheRS. We generated a backbone-independent rotamer library for 2, in which both the $\chi 1$ and $\chi 2$ torsional angles were varied by $\pm 20°$ (in increments of 5°) from the values of 1 in the tPheRS structure. Design calculations were performed by fixing the identity of the substrate (2) and by allowing each of 11 non-anchor sites in the amino acid binding pocket of tPheRS (determined from the crystal structure) to be occupied by any of the twenty natural amino acids except for proline, methionine and cysteine. The anchor residues (Glu128, Glu130, Trp149, His178, Ser180, Gln183, and Arg204) were held fixed in identity and conformation in all calculations. These residues contribute important electrostatic interactions with the substrate and it is reasonable to assume that such interactions are equally critical for the binding of 2.

The calculations identified two important cavity-forming mutations: Val261 (Thr251 in *E. coli*) to Gly, and Ala314 (Ala294 in *E. coli*) to Gly. These predictions are consistent with the results of Reshetnikova and coworkers,[9] who pointed out that Ala314 and Val261 hinder the binding of amino acids larger than phe (e.g., tyrosine) into active site of tPheRS. Further confidence in the prediction was engendered by the fact that the Ala294Gly mutant allows incorporation of an interesting set of para-substituted phenylalanines, as described earlier.[4,5] We were thus encouraged to test whether the additional Thr251Gly mutation would relax the specificity of ePheRS* sufficiently to allow incorporation of 2 into proteins in vivo.

Figure 3A:
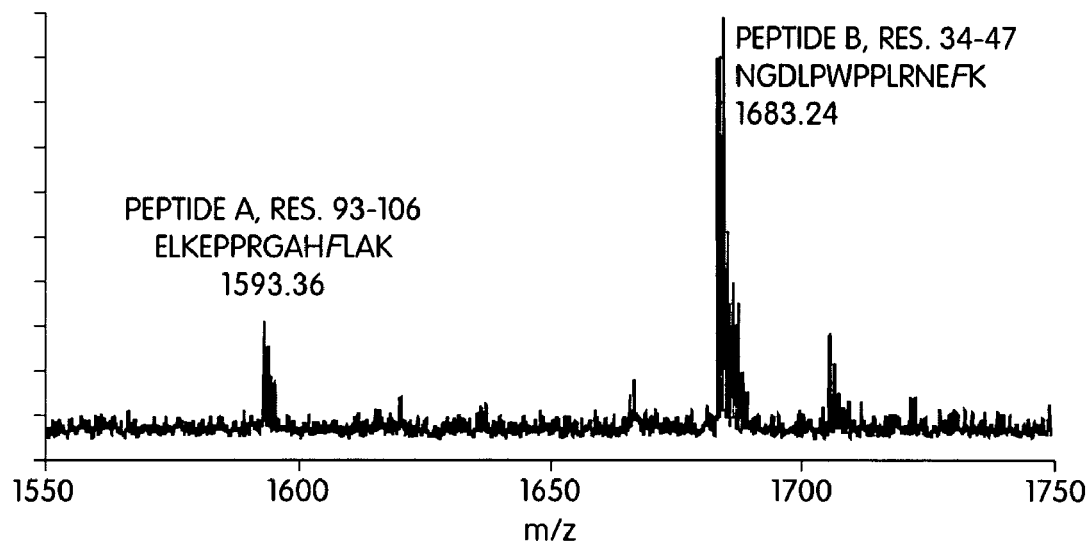
FIG. 3 MALDI-TOF mass spectra of tryptic peptides digested from mDHFR expressed in media supplemented with 1(a) or 2(b). Peptides A and B are represented by SEQ ID NOs: 1 and 2, respectively.
Figure 3B:
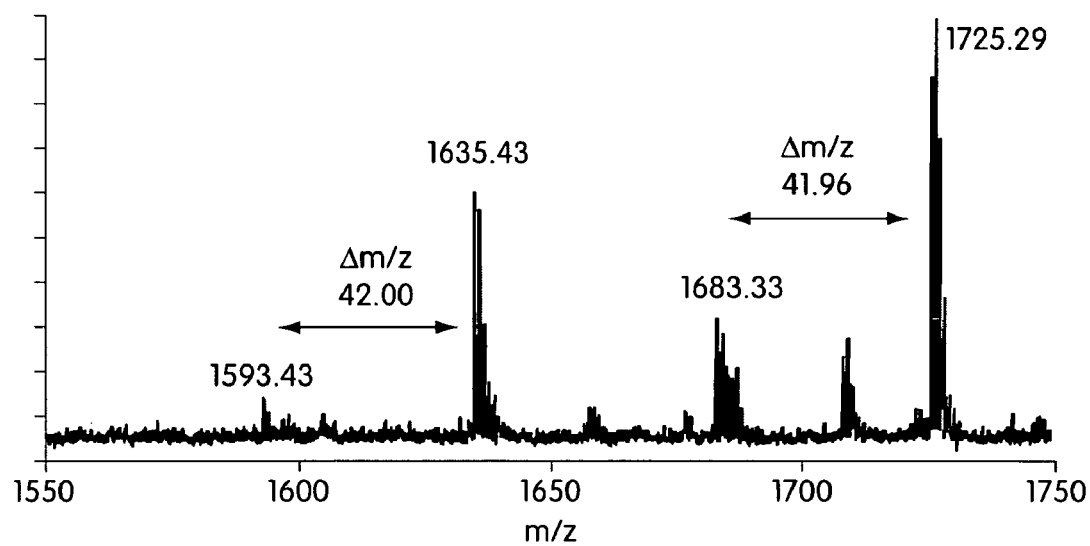

*E coli* pheS* (which encodes ePheRS*) was amplified by the polymerase chain reaction (PCR) from vector pQE-FS.[4] Amplified pheS* was subjected to PCR mutagenesis to create the coding sequence for the desired Thr251Gly mutant, which we designate pheS. To allow constitutive expression of the synthetase, a tac promotor with an abolished lac repressor binding site was inserted upstream of the start codon of pheS.[11] The expression cassette was then cloned into pQE15 (Qiagen), which encodes the marker protein mouse dihydrofolate reductase (mDHFR). The resulting plasmid was designated pQE-FS**. As a control, plasmid pQE-FS* (which contained pheS* under control of a constitutive tac promoter) was constructed similarly. AF-IQ, a phenylalanine auxotrophic *E. coli* strain carrying the repressor plasmid pLysS-IQ,[4] was transformed with pQE15, pQE-FS*, or pQE-FS** to generate expression systems AF-IQ[pQE15], AF-IQ[pQE-FS*], and AF-IQ[pQE-FS**], respectively. The capacity of 2 to support protein synthesis in each expression system was determined by induction of mDHFR expression in phenylalanine-free minimal media supplemented with 2. As shown in SDS-PAGE analysis of whole cell lysates (FIG. 2), neither AF-IQ[pQE15] nor AF-IQ[pQE-FS*] exhibits protein expression above background (-phe) in media supplemented with 2.12 We note that Phe starvation does not completely eliminate background expression, presumably because of incomplete depletion of the cellular pool of phe. In contrast, similarly supplemented cultures of AF-IQ[pQE-FS**] yield high levels of mDHFR expression. The histidine-tagged protein from the latter culture (mDHFR-2) was purified in a yield of about 20 mg/L, approximately 60% of that obtained from cultures supplemented with 1. MALDI-TOF mass spectrometry showed that the mass of mDHFR-2 was increased by 304 Da, which corresponds to approximately 80% replacement of 1 by 2 (mDHFR contains 9 Phe residues). Incorporation of 2 was confirmed by tryptic digestion of mDHFR-2 (FIG. 3). For mDHFR, two peptides (Peptides A and B) in the mass range 1550–1750 Da were assigned to residues 34–47 and 94–106, respectively (FIG. 3a). Each fragment contains a single Phe residue. The corresponding fragments of mDHFR-2 (FIG. 3b) were shifted up in mass by 42 Da, consistent with the increased mass of 2 relative to 1.[13]

Figure 4A:
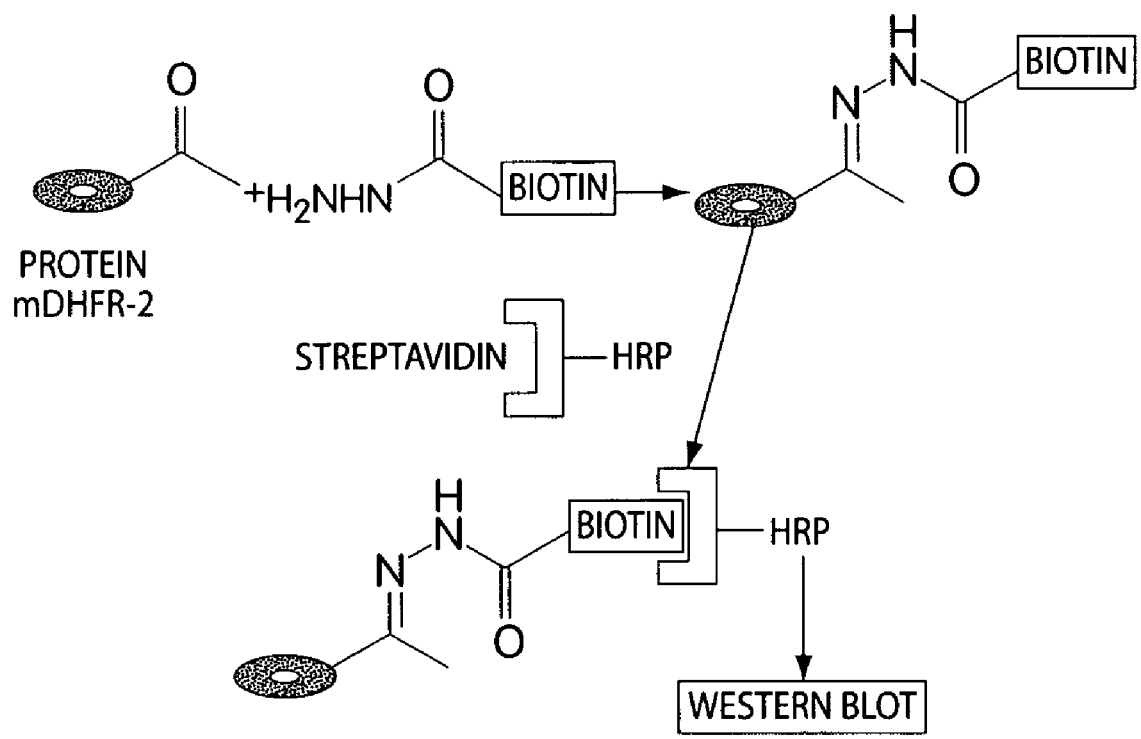
FIG. 4 Western blot showing chemoselective modification of ketone functionality in mDHFR. (a) Modified protein was treated with biotin hydrazide (BH), stained with HRP conjugated streptavidin and analyzed by western blot. (b) Western blot analysis of the products. Lane 1: mDHFR-wt+buffer; Lane 2: mDHFR-2+buffer, lane 3: mDHFR-wt+BH; Lane 4: mDHFR-2+BH.
Figure 4B:
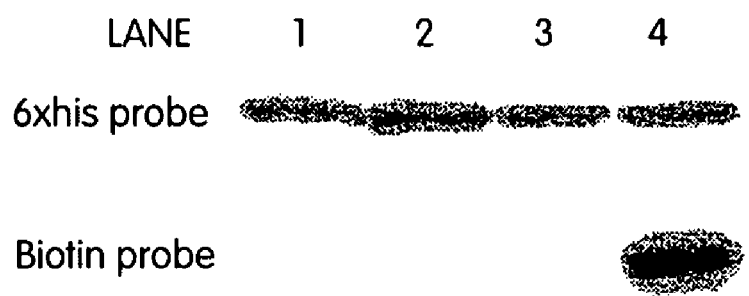
Figure 5:
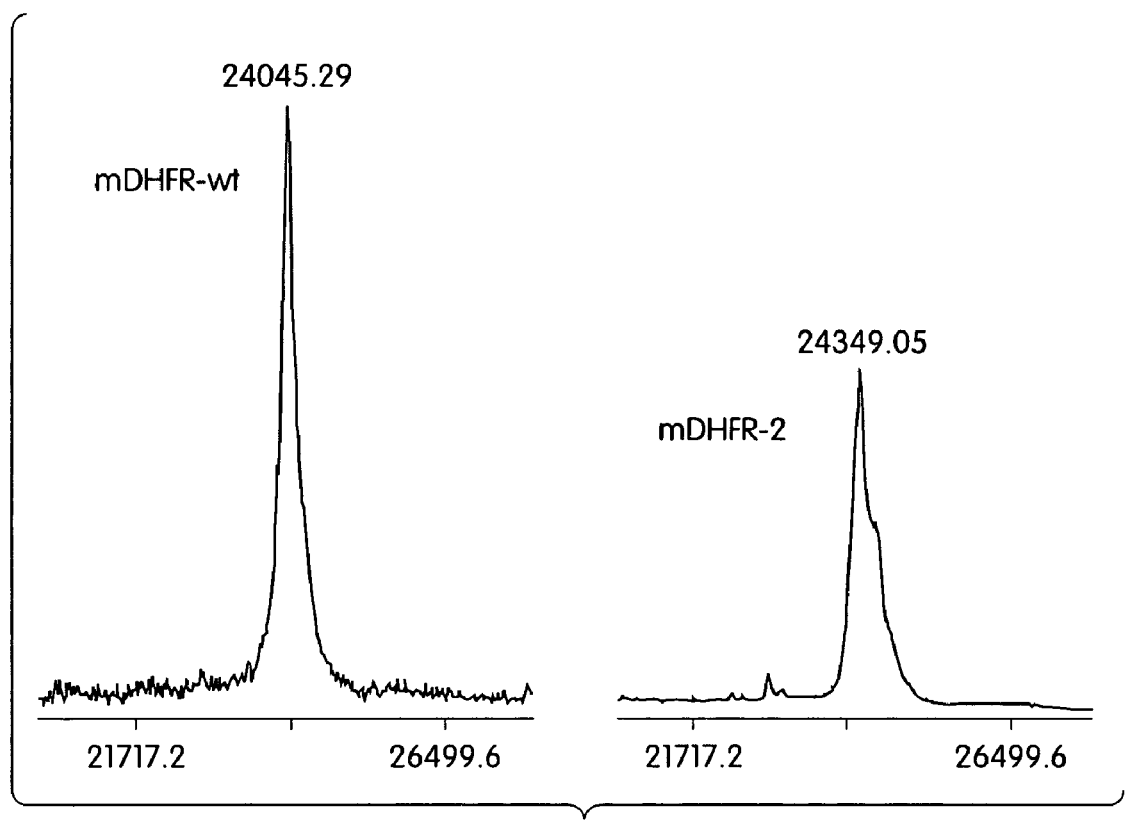
FIG. 5 MALDI-MS (Matrix-Assisted Laser Desorption Ionization Mass Spectrometry) of purified proteins.
Figure 6A:
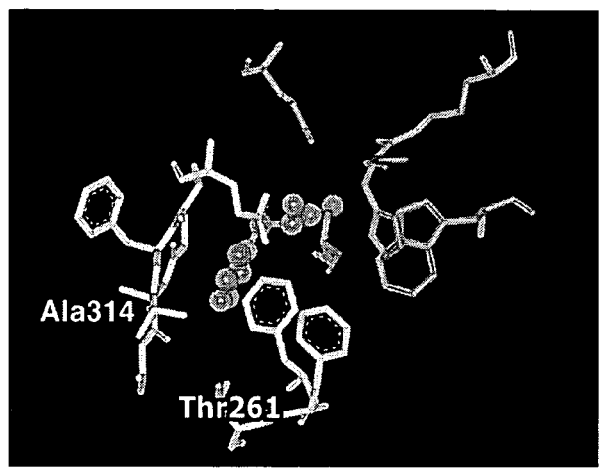
FIG. 6 Active sites in tPheRS. (a) wild type; (b) A314G mutant; (c) T261G/A314G double mutant.
Figure 6B:
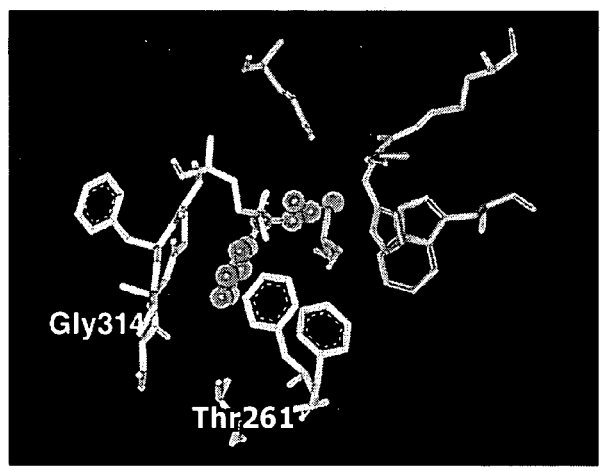
Figure 6C:
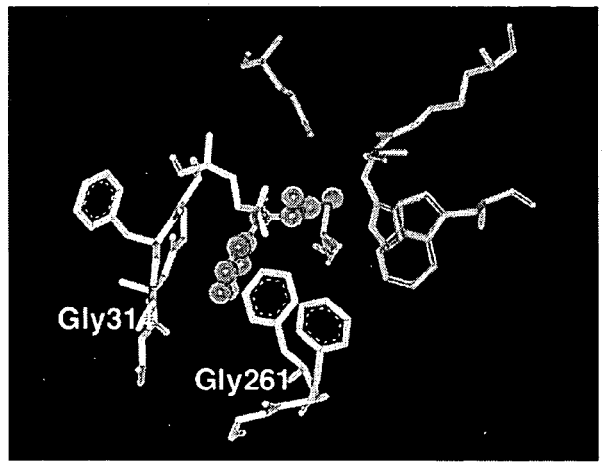

We have completed preliminary studies of the reactivity of mDHFR-2 toward hydrazide reagents. Purified mDHFR and mDHFR-2 were dissolved in PBS buffer (pH 6.0) and treated either with 5 mM biotin hydrazide (BH) or with PBS buffer as a negative control. The reaction products were analyzed by western blotting and visualized by treatment with a biotin-specific streptavidin-HRP conjugate (FIG. 4). The products were also examined for the presence of the 6×His tag of mDHFR to ensure the identity of the protein band and to probe the possibility of chain cleavage under the ligation conditions. The results are consistent with chemoselective ligation without chain cleavage (FIG. 4b).

In conclusion, we describe here a new mutant form of the *E. coli* phenylalanyl-tRNA synthetase, which was designed based on the known structure of the related *Thermus thermophilus* PheRS (tPheRS). The new mutant form of the *E. coli* phenylalanyl-tRNA synthetase (ePheRS**) allows efficient in vivo incorporation of reactive aryl ketone functionality into recombinant proteins. This study also demonstrates the power of computational protein design in the development of aminoacyl-tRNA synthetases for activation and charging of non-natural amino acids.

Supporting Information

Plasmid Construction

*E. coli* pheS* was amplified by the polymerase chain reaction (PCR) from vector pQE-FS.[4] Amplified pheS* was subjected to PCR mutagenesis to create the coding sequence for the desired Thr251Gly mutant, which we designatepheS**. To allow constitutive expression of the synthetase, a linker encoding a tac promoter with an abolished lac repressor binding site was prepared with terminal NheI restriction sites and internal NcoI and HirdIII sites. The linker sequence is:

```
5'CTAGCAGTTGACAATTAATCATCGGCTCGTATAATGGATCGAATTGTGAGCGGAATCGAT

TTTCACACAGGAAACAGACCATGGATCTTCGTCGCCATCCTCGGGTCGACGTCTGTTGCAAGCTTG-3'
```

(SEQ ID NO: 3, the -35 and -10 sequences are underlined and the start codon is in bold).

This linker was cloned into the NheI site of vector pET5a (Novagen) to form pET5a-tac. PCR amplified fragments containing pheS* and pheS** were cloned into pET5a-tac at the NcoI and HindIII sites. pheS* and pheS** outfitted with the tac promoter were cut out as NheI fragments and inserted into expression plasmid pQE15 (Qiagen) to yield pQE-FS* and pQE-FS**, respectively. Expression plasmids pQE15, pQE-FS* and pQE-FS** encode the marker protein murine dihydrofolate reductase (mDHFR) under control of a bacteriophage T5 promoter.

Determination of Translational Activity

Buffer and media were prepared according to standard protocols. A phenylalanine auxotrophic derivative of *E. coli* strain BL21(DE3), designed AF (HsdS gal (χcIts857 ind I Dam5 lacUV5-T7 gene 1) pheA) and constructed in our laboratory, was used as the expression host. The AF strain was transformed with repressor plasmid pLysS-IQ and with pQE15, pQE-FS* or pQE-FS** to generate expression strains AF-IQ[pQE15], AF-IQ[pQE-FS*] or AF-IQ[pQE-FS**], respectively.

Small scale (10 ml) cultures were used to investigate the in vivo translational activity of 2 (p-AcetylPhe). M9 minimal medium (50 ml) supplemented with 0.2% glucose, 1 mg/L thiamine, 1 mM $MgSO_4$, 1 mM $CaCl_2$, 19 amino acids (at 20 mg/L), antibiotics (ampicillin 200 mg/L, chloramphenicol 35 mg/L) and phenylalanine (at 20 mg/L) was inoculated with 1 ml of an overnight culture of the expression strain. When the optical density at 600 nm reached 0.8–1.0, a medium shift was performed. Cells were sedimented by centrifugation for 15 min at 3,100 g at 4° C., the supernatant was removed and the cell pellets were washed twice with 0.9% NaCl. Cells were resuspended in supplemented M9 medium containing either: (a) 250 mg/L of p-AcetylPhe 2, (b) 20 mg/L phe (1) (positive control), or (c) no phe or analog (negative control). Protein expression was induced 10 min after the medium shift by addition of isopropyl-β-D-thiogalactoside (IPTG) to a final concentration of 1 mM. Cells were cultured for 4 hours post-induction and protein expression was monitored by SDS polyacrylamide gel electrophoresis (PAGE, 12%), using a normalized $OD_{600}$ of 0.2 per sample.

Protein Purification mDHFR as expressed in this work contains an N-terminal hexahistidine (6×His) sequence, which was utilized to purify the protein by nickel affinity chromatography with stepwise pH gradient elution under denaturing conditions according to the recommendations of the supplier (Qiagen). The eluted protein was buffer-exchanged (Millipore, MWCO=5 kDa) against distilled water three times and the purified protein was subjected to matrix-assisted laser desorption ionization mass spectrometry (MALDI-MS) analysis.

Tryptic Peptide Analysis

10 µl of purified protein in elution buffer (8M urea, 100 mM $NaH_2PO_4$, 10 mM Tris, pH 4.5) was mixed with 90 µl 75 mM $NH_4OAc$, to which 2 µL of modified trypsin (Promega, 0.2 µg/µL) was added. The solution was allowed to digest overnight at room temperature. The reaction was quenched by addition of trifluoroacetic acid to pH<4.0. The digest was subjected to sample clean-up by using ZipTip$_{c18}$, which provided 2 µl of purified sample solution. 10 µl of the MALDI matric (α-cyano-β-hydroxycinnamic acid, 10 mg/ml in 50% $CH_3CN$) was added, and 0.5 µl of the resulting solution was spotted directly onto the sample plate. Samples were analyzed in the linear mode on an Applied Biosystems Voyager DE Pro MALDI-TOF mass spectrometer.

Chemical Modification of Protein

Purified proteins (mDHFR-wt and mDHFR-2) were dissolved in 200 µl of PBS buffer (pH 6.0) and added to 20 µl of 5 mM biotin hydrazide (BH, dissolved in PBS). Protein/BH mixtures were incubated at room temperature for 1 to 1.5 hr. Reaction solutions were then washed twice with distilled water using a buffer-exchange column (Millipore, MWCO=5 kDa). Standard Western blotting procedures were used to identify proteins modified with BH as well as those bearing an N-terminal hexahistidine tag.

II. Design Calculations for Redesigning Phe Binding Pocket in Phe tRNA Synthetase for Binding to DPA, A Phenylalanine Analog To create mutant AARSs that are able to bind to unnatural amino acids, and eventually amino acylate 3' ends of tRNAs, a three-step approach can be adopted:

1) Design the binding site of natural AARSs by using a protein design algorithm to generate mutants that will bind to non-canonical amino acids;
2) Calculate simulated binding energies and check for specificity of the designed mutants using a heir-DOCK protocol;
3) Experimentally test for the incorporation of the artificial amino acid using an in vivo/in vitro system.

Methodology and Rationale

Model System

Figure 7:
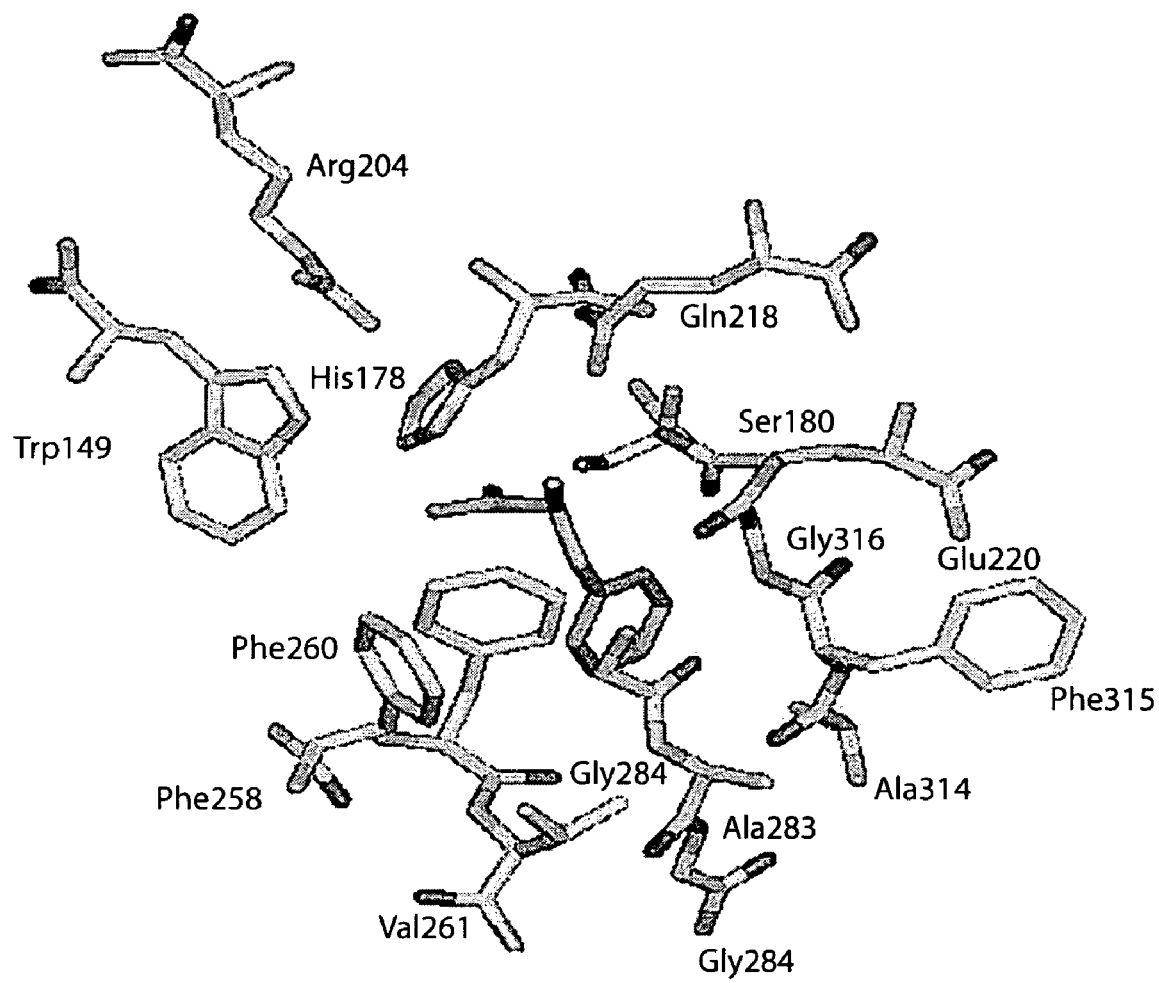
FIG. 7 The binding pocket for Phe in PheRS. Phenylalanine zwitterion is represented in purple. The anchor residues are labeled in bold.

Phenylaanine-tRNA synthetase (PheRS): We have selected the PheRS as our model for this study. PheRS is an $(\alpha\beta)_2$ enzyme with 350 amino acids in the a subunit and 785 in the β subunit (Stepanov et al., 1992; Reshetnikova et al., 1999). The binding site for phenylalanine (Phe) is in the α subunit (FIG. 7). There are a number of reasons for selecting this system. The crystal structure of PheRS bound to its natural substrate, Phe, is readily available. An accurate description of the binding pocket is critical for the computational design approach since it depends on the crystal structure for the protein backbone descriptions, although in many cases it is perfectly acceptable to use crystal structure of a homologous protein (for example, a homolog from a related species) or even a conserved domain to substitute the binding pocket. The crystal structure also defines the orientation of Phe in the binding pocket of the synthetase. The aromatic ring of Phe is buried in the hydrophobic pocket while the carbonyl and the amide groups of the backbone make extensive electrostatic contacts with the charged and polar residues at the mouth of the pocket. We would like to design the binding pocket for the analogs so that these analogs bind to PheRS in the same orientation as Phe, since this orientation may be important for the adenylation step.

Another reason for using this system is that the structure of PheRS does not undergo any significant structural rearrangement on substrate binding as indicated by the crystal structures of the free PheRS and the PheRS-Phe complex. This makes the system well suited for our protein design algorithm which uses a fixed-backbone structure for side-chain selection. PheRS is an extensively studied system for the assimilation of artificial amino acids and has been used successfully in incorporation of a few Phe analogs. In fact, limited mutation analysis has also been done on this system to alter substrate specificity (Kast and Hennecke, 1991). Moreover, molecular dynamics (MD) simulations have been performed in an effort to understand the binding behavior of PheRS towards various analogs.

Figure 8:
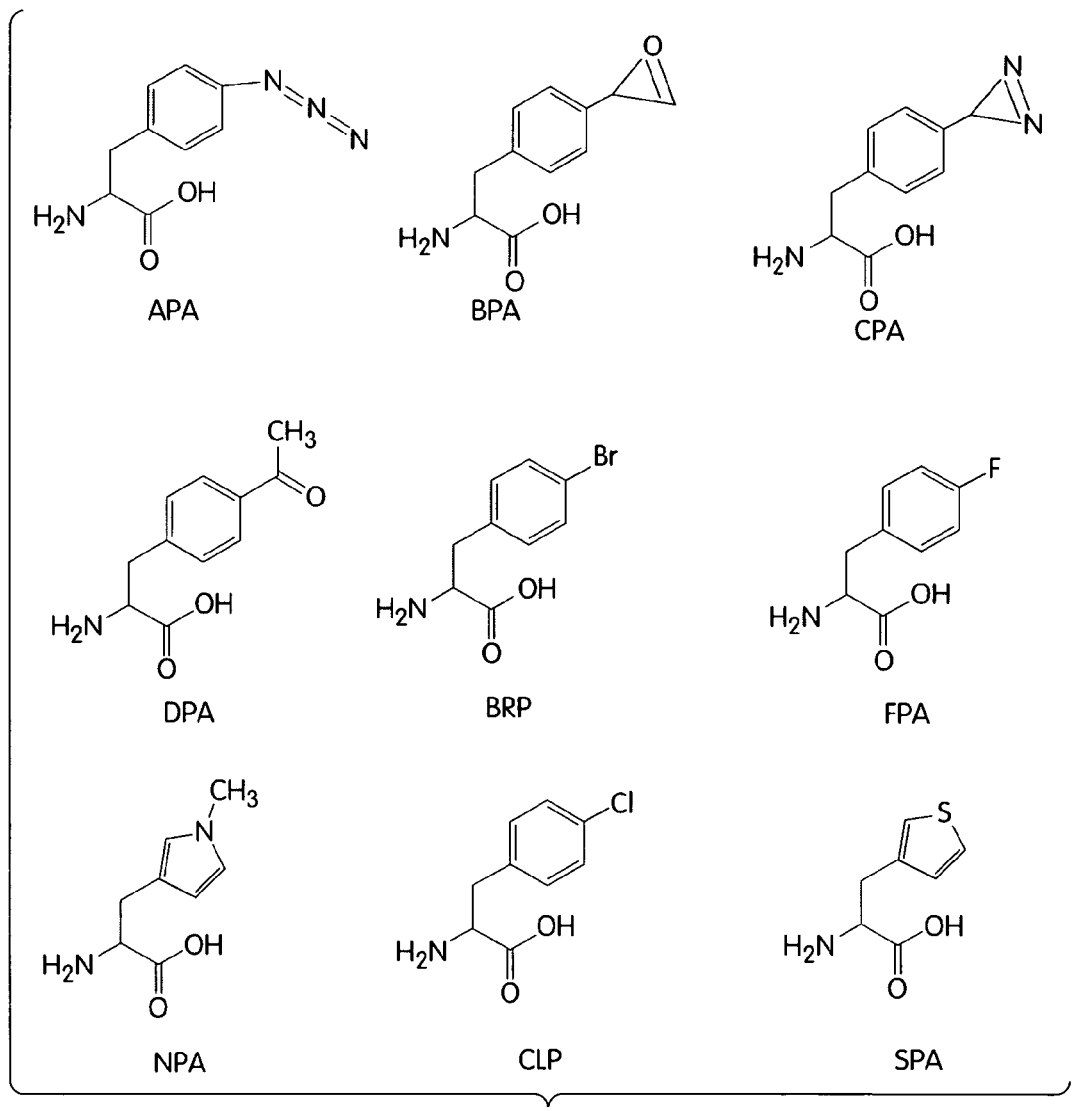
FIG. 8 Analogs tested for incorporation in in vivo assays. FPA and SPA are the only two analogs that get incorporated by the natural PheRS.

Analogs: The Phe analogs selected for the study are shown in FIG. 8. These analogs have been experimentally tested to check if they are readily incorporated in proteins by the natural PheRS. MD simulations were performed using these analogs and significant correlation was achieved between the predicted binding energies and the in vivo incorporation rates exhibited by these analogs (Wang et al., 2001).

Binding Site Design

We used a protein design algorithm (Dahiyat and Mayo 1996; Dahiyat et al., 1997), ORBIT, to predict the optimal amino acid sequences of the binding pocket for binding to the different analogs. Selection of amino acids is performed using a very efficient search algorithm that relies on a discrete set of allowed conformations for each side chain and empirical potential energy functions that are used to calculate pair-wise interactions between side chains and the between the side chains and backbone.

Surveys of protein structure database have shown that side chains exhibit marked conformational preferences, and that most side chains are limited to a small number of torsional angles. Thus, the torsional flexibility of most amino acids can be represented with a discrete set of allowed conformations called rotamers. Rotameric preferences in side chains are observed that depend on the main-chain conformations. ORBIT accounts for the torsional flexibilities of side chains by providing rotamer libraries that are based on those developed by Dunbrack and Karplus (Dunbrack and Karplus 1993; Dunbrack and Karplus 1994).

In our design, we would like to optimize the binding pocket for binding to Phe analogs. In performing the optimization calculations, we would like to vary the torsional angles of analogs and side chains lining the pocket simultaneously. This requires generating rotamer libraries for the analogs, since they are not included in our standard rotamer libraries. For all the natural amino acids, the possible $\chi 1$ and $\chi 2$ angles are derived from database analysis. Since this is not feasible in the case of artificial amino acids, the closest approximation for $\chi 1$ and $\chi 2$ angles for Phe analogs are taken to be the same as those for Phe. Moreover, we would like the analogs to have a conformation as close as possible to the orientation of Phe in the binding pocket. So allowing similar torsional angles for the analogs as of Phe seems logical.

Since the residues in the pocket are buried in the protein structure, we have force field parameters similar to those used in previous protein core design calculations. The design algorithm uses energy terms based on a force field that includes van der Waals interactions, electrostatic interactions, hydrogen bonding, and solvation effects (Gordon et al., 1999).

Backbone independent rotamer libraries for all the analogs shown in FIG. 8 are generated. Both the $\chi 1$ and $\chi 2$ torsional angles were varied to match those of Phe rotamers in our standard backbone independent rotamer library. The torsional angles of Phe in the crystal structure ($\chi 1$:−101°, $\chi 2$:−104°) were also included in the new rotamer libraries for both Phe and the analogs. Charges were assigned only to the heavy atoms of the analogs to be consistent with the way charges for the natural amino acids are represented in ORBIT. The first analog selected for design was DPA.

Design calculations were run by fixing the identity of the substrate to be DPA and varying 11 other positions on PheRS (137, 184, 187, 222, 258, 260, 261, 286, 290, 294, and 314). Positions 137, 184, 258, 260, 261, 286, 290, 294, 314 were allowed to be any of the 20 natural amino acids except proline (Pro or P), methionine (Met or M) and cysteine (Cys or C). Methionine was allowed at position 187 because its wild-type identity is Met, and only hydorphobic amino acids were allowed at position 222. Most of these positions are buried in the core and a number of them pack against Phe in the crystal structure. Mutation analysis at position 294 has been shown to alter substrate specificity. The anchor residues (Glu 128, Glue 130, Trp 149, His 178, Ser 180, Gln 183, Arg 204) were held fixed both in identity and conformation in all the calculations. These make very important electrostatic interactions with the substrate and this interaction is probably equally critical for the analogs. From the crystal structure it appears that the anchor residues hold the Phe zwitterion in a way that the carbonyl group of the zwitterion is close to the ATP binding site. This proximity may be important for the aminoadenylation reaction. The aminoadenylation step is required for the incorporation of all the amino acids and hence, it seems important to make sure that the carbonyl and the amide groups of the analog zwitterions are also anchored the same way as the natural substrate at this site.

In the first design attempt we allowed all the DPA rotamers that were generated in the rotamer library. The DPA rotamer selected in the structure generated was not buried in the binding pocket and most of it is solvent-exposed. A second calculation was run allowing only those DPA rotamers that would pack into the binding pocket. These are the rotamers with all possible combinations of $\chi 1$ of −101 (±20°) and $\chi 2$ of −104 (±20°) in increments of 5°. The structure generated in this calculation has the aromatic ring of DPA buried in the pocket and is almost completely superimposable with the Phe in the PheRS crystal structure.

RBIAS—for Enhancing Protein-substrate Interactions

The sequence generated in the first calculation has two important cavity forming mutations which are Val261 to Glycine and Ala314 to Glycine. Mutation to Glycine at position 314 has been previously reported to have enhanced the incorporation of larger Phe analogs that are not incorporated by the wild type synthetase. All the mutations predicted in this calculation gear towards making enough space in the binding pocket for accommodating DPA, but besides van der Waals interactions, we do not see any specific interaction between DPA and the synthetase.

In an attempt to design specificity into the protein-substrate interaction, we developed a program, RBIAS, which enhances the interactions between the substrate and the protein positions. This is done by scaling up the pair-wise energies between the substrate and the amino acids allowed at the design positions on the protein in the energy calculations. In an optimization calculation where the protein-substrate interactions are scaled up compared to the intra-protein interactions, sequence selection will be biased toward selecting amino acids to be those that have favorable interaction with the substrate.

We performed multiple calculations by scaling up the substrate-protein by factors of 2.0 to 20.0, in increments of 2.0. A scale factor of 4.0 generated an interesting mutation, Val 286 to Gln, which makes a hydrogen bond with acetyl group at the distal end of DPA. The interaction between DPA and the PheRS in this sequence was enhanced by 2.12 kcal/mol although the complex is destabilized by 12.96 kcal/mol as indicated by the total energy. A bias scale factor of 18.0 generated a new mutation, Val 290 to Lysine. We believe this mutation is not important for specificity since lysine at this position is not making significant interactions with DPA. Moreover, polar groups in the core, especially those that are not involved in a salt-bridge or a hydrogen bond may significantly destabilize proteins. Therefore, we can trade off only some amount of overall protein stability in order to gain specificity between the protein and the substrate. Based on these considerations, the following sequence mutations or combinations thereof are good candidates for further testing:

Sequences Suggested for Further Testing

|  | Mutations |
| --- | --- |
| Double Glycine | V261G, A314G |
| Double Gly + Gln | V261G, A314G, V286Q |
| Double Gly + Gln 286 + Leu 290 | V261G, A314G, V286Q, V290L |

In all calculations, position 258 is mutated from Phe to Tyr. This position is slightly exposed and is not in direct contact with DPA. Position 258 is very close to the anchor residues so mutating it may affect the transfer of the amino acid to its RNA. We recommend not including this mutation, We also recommend ignoring mutations V184I (this position is far enough from the substrate binding site and therefore, may not affect binding) and L222A (this mutation is predicted because of a potential clash between Methionine rotamer at 187 and Leucine at 184 in the calculation).

REFERENCES 1. (a) Dougherty, D. A. Curr. Opin. Chem Biol. 2000, 4, 645–652 (b) Minks, C. Alefelder, S. Moroder, L., Huber, R., Budisa, N. Tetrahedron 2000, 56, 9431–9442. (c) Behrens, C., Nielsen, J. N., Fan, X. J., Doisy, X., Kim, K. H., Praetorius-Ibba, M., Nielsen, P. E., Ibba, M. Tetrahedron 2000, 56 9443–9449.
2. Tang, Y; Giovanna, G.,; Petka, W. A.; Nakajima, T.; Degrado, W. F.; Tirrell, D. A. *Agnew. Chem. Int. Ed Engl.* 2001, 40, 1494–1496.
3. (a) Ibba, M.; Hennecke, H. *FEBS Lett.* 1995, 364, 272–275. (b) Ibba, M.; Kast, P.; Hennecke, H. *Biochemistry* 1994, 33, 7107–7112. (c) Kast, P.; Hennecke, H. *J. Mol. Biol* 1991, 222, 99–124.
4. Sharma, N.; Furter, R.; Tirrell, D. A. *FEBS Lett* 2000, 467, 37–40.
5. Kirshenbaum, K; Carrico, I. S.; Tirrell, D. A. *Chem. BioChem.* 2001, I in press.
6. (a) Rose, K. *J Am. Chem. Soc.* 1994, 116, 30–33. (b) Canne, L. E.; FerreDAmare, S. K.; Burley, S. B. H. *J. Am. Chem Soc.* 1995, 117, 2998–3007. (c) Rideout, D.; Calogeropoulou, T. *Biopolymers* 1990, 29, 247–262. (d) Rideout, D. *Cancer Invest.* 1994, 12, 189–202. (e) Shao, J.; Tam, J. P. *J Am Chem Soc* 1995, 117, 3893–3899.
7. (a) Mahal, L. K.; Yarema, K. J.; Bertozzi, C. R. *Science* 1997, 276, 1125–1128. (b) Yarema, K. J.; Mahal, L. K.; Bruehl, R. E.; Rodriguez, E. C.; Bertozzi, C. R. *J. Biol. Chem* 1998 273, 31168–31179.
8. Cornish, V. W.; Hahn, K. M.; Schultz, P. G. *J. Am. Chem. Soc* 1996, 118, 8150–8151.

Table for RBIAS calculations: A big energy clash between DPA and the binding pocket in the wild type sequence (WT-indicates why DPA is not incorporated by the wild type synthetase

| Sequence | 128 | 130 | 137 | 149 | 178 | 180 | 183 | 184 | 187 | 204 | 222 | 258 |
|---|---|---|---|---|---|---|---|---|---|---|---|---|
| WT_Phe | E | E | L | W | H | S | Q | V | M | R | L | F |
| No bias_phe | E | E | L | W | H | S | Q | I | M | R | A | Y |
| WT_DPA | E | E | L | W | H | S | Q | V | M | R | L | F |
| No bias_dpa | E | E | L | W | H | S | Q | I | M | R | L | Y |
| Bias 2.0 | E | E | L | W | H | S | Q | I | M | R | L | Y |
| Bias 4.0 | E | E | L | W | H | S | Q | I | M | R | A | Y |
| Bias 6.0 | E | E | L | W | H | S | Q | I | M | R | A | Y |
| Bias 8.0 | E | E | L | W | H | S | Q | I | M | R | A | Y |
| Bias 10.0 | E | E | L | W | H | S | Q | I | M | R | A | Y |
| Bias 12.0 | E | E | L | W | H | S | Q | I | M | R | A | Y |
| Bias 14.0 | E | E | L | W | H | S | Q | I | M | R | L | Y |
| Bias 16.0 | E | E | L | W | H | S | Q | I | M | R | L | Y |
| Bias 18.0 | E | E | L | W | H | S | Q | I | M | R | A | Y |
| Bias 20.0 | E | E | L | W | H | S | Q | I | M | R | A | Y |

| Sequence | 260 | 261 | 286 | 290 | 294 | 314 | Ligand Energy | Total Energy |
|---|---|---|---|---|---|---|---|---|
| WT_Phe | F | V | V | V | V | A | −16.91 | −240.71 |
| No bias_phe | F | V | L | I | I | A | −16.87 | −242.1469 |
| WT_DPA | F | V | V | V | V | A | 1033145 | 51669.81 |
| No bias_dpa | F | G | L | I | V | | −21.40 | −225.13 |
| Bias 2.0 | F | G | L | I | V | G | −21.40 | −225.13 |
| Bias 4.0 | F | G | Q | L | V | G | −23.52 | −212.17 |
| Bias 6.0 | F | G | Q | L | V | G | −23.52 | −212.17 |
| Bias 8.0 | F | G | Q | L | V | G | −23.52 | −212.17 |
| Bias 10.0 | F | G | Q | L | V | G | −23.52 | −212.17 |
| Bias 12.0 | F | G | Q | L | V | G | −23.52 | −212.17 |
| Bias 14.0 | F | G | Q | L | V | G | −23.63 | −209.34 |
| Bias 16.0 | F | G | Q | L | V | G | −23.63 | −209.34 |
| Bias 18.0 | F | G | Q | K | V | G | −23.96 | −198.83 |
| Bias 20.0 | F | G | Q | K | V | G | −23.96 | −198.83 |

9. (a) Reshetnikova, L.; Moor, N.; Lavrik, O.; Vassylyev, D. G. *J. Mol. Bio.* 1999, 287, 555–568. (b) Fishman R.; Ankilova, V.; Moor, N.; Safro, M. *Acta Cryst.* 2001, D57, 1534–1544.
10. Dayiyat, B. I.; Mayo, S. G. *Science* 1997, 278, 82–87.
11. Furter, R. *Protein Sci* 1998, 7, 419–426.
12. Phe starvation does not completely eliminate background expression, presumably because of incomplete depletion of the cellular pool of phe.
13. The enhanced promiscuity of ePheRS** allows misincorporation of tryptophan under phe starvation conditions in the absence of 2. In media supplemented with 2 there is no detectable misincorporation of any of the canonical amino acids. We have not observed misincorporation of tyrosine under any conditions.
14. Budisa, N., Steipe, B., Demange, P. Eckerskorn, C., Kellermann, J., and Huber, R. (1995). High-Level Biosynthetic Substitution of Methionine in Proteins by its Analogs 2-Aminohexanoic Acid, Selenomethionine, Telluromethionine, and Ethionine in *E. coli. Eur. J. Biochem* 230: 788–796.
15. Dahiyat, B. I. and Mayo, S. L. (1996). *Protein Sci* 5(5): 895–903.
16. Dahiyat, B. I., Sarisky, C. A., Mayo, S. L. (1997). De novo protein design: towards fully automated sequence selection. *J Mol Biol* 273(4): 789–96.
17. Deming, T. J., Fournier, M. J., Mason T. L., and Tirrell, D. A. (1997). Biosynthetic Incorporation and Chemical Modification of Alkene Functionality in Genetically Engineered Polymers. *J. Macromol. Sci. Pure Appl. Chem* A34; 2143–2150.
18. Duewel, H., Daub, E., Robinson, V., and Honek, J. F. (1997). Incorporation of Trifluoromethionine into a Phage Lysozyme: Implications and a New Marker for Use in Protein 19F NMR. *Biochemistry* 36(3404–3416).
19. Dunbrack, R. L. and Karplus, M. (1993). Backbone-dependent rotamer library for proteins. Application to side-chain prediction. *J Mol Biol* 230(2): 543–74.
20. Dunbrack, R. L. and Karplus, M. (1994). Conformational analysis of the backbone-dependent rotamer preferences of protein side chains. *Nat Struct Biol* 1(5): 334–40.
21. Ewing J. A., Kuntz, I. D. (1997). Critical evaluation of search algorithms for automated molecular docking and database screening. *J Comp Chem* 18: 1175–1189.
22. Floriano, W. B., Vaidehi, N., Goddard, W. A., Singer, M. S., Shepherd, G. M. (2000). Molecular mechanisms underlying differential odor responses of a mouse olfactory receptor. *Proc Natl Acad Sci USA* 97(20): 10712–6.
23. Ghosh, G., Pelka, H., Schulman, L. H. (1990). Identification of the tRNA anticodon recognition site of *E. coli* methionyl-tRNA synthetase. *Biochemistry* 29(9): 2220–5.
24. Gordon, D. B., S. A. Marshall, Mayo, S. L. (1999). Energy functions for protein design. *Curr Opin Struct Biol* 9(4): 509–13.
25. Kast, P., Hennecke, H. (1991). Amino acid substrate specificity of *Escherichia coli* phenylalanyl-tRNA synthetase altered by distinct mutations. *J Mol Biol.* 222(1): 99–124.
26. Reshetnikova, L., Moor, N., Lavrik, O., Vassylyev, D. G. (1999). Crystal structures of phenylalanyl-tRNA synthetase complexed with phenylalanine and a phenylalanyl-adenylate analogue. *J Mol Biol* 287(3): 555–68.
27. Sharma, N., Furter, R., Kast, P., Tirrell, D. A. (2000). Efficient introduction of arylbromide functionality into proteins in vivo. *FEBS Lett* 467(1): 37–40.
28. Stepanov, V. G., Moor, N. A., Ankilova, V. N. Lavrik, O. I. (1992). Phenylalanyl-tRNA synthetase from *Thermus thermophilus* can attach two molecules of phenylalanine to tRNA(Phe). *FEBS Lett* 311(3): 192–4.
29. van Hest, J. C. and Tirrell, D. A. (1998). Efficient introduction of alkene functionality into proteins in vivo. *FEBS Lett* 428(1–2): 68–70.
30. Wang, P., Vaidehi, N. Tirrell, D. A., and Goddard III, W. A. (2001). In preparation.

The practice of the present invention will employ, unless otherwise indicated, conventional techniques of molecular biology, cell biology, cell culture, microbiology and recombinant DNA, which are within the skill of the art. Such techniques are explained fully in the literature. See, for example, *Molecular Cloning: A Laboratory Manual*, $2^{nd}$ Ed., ed. By Sambrook, Fritsch and Maniatis (Cold Spring Harbor Laboratory Press: 1989); *DNA Cloning*, Volumes I and II (D. N. Glover ed., 1985); *Oligonucleotide Synthesis* (M. J. Gait ed., 1984); Mullis et al.; U.S. Pat. No. 4,683,195; *Nucleic Acid Hybridization* (B. D. Hames & S. J. Higgins eds. 1984); *Transcription And Translation* (B. D. Hames & S. J. Higgins eds. 1984); B. Perbal, *A Practical Guide To Molecular Cloning* (1984); the treatise, *Methods In Enzymology* (Academic Press, Inc., N.Y.); *Methods In Enzymology*, Vols. 154 and 155 (Wu et al. eds.), *Immunochemical Methods In Cell And Molecular Biology* (Mayer and Walker, eds., Academic Press, London, 1987).

The contents of all cited references (including literature references, issued patents, published patent applications as cited throughout this application) are hereby expressly incorporated by reference.

EQUIVALENTS

Those skilled in the art will recognize, or be able to ascertain using no more than routine experimentation, numerous equivalents to the specific method and reagents described herein, including alternatives, variants, additions, deletions, modifications and substitutions. Such equivalents are considered to be within the scope of this invention and are covered by the following claims.

The invention claimed is:

1. A method for designing amino acid sequence change(s) in an aminoacyl tRNA synthetase (AARS), wherein said change could enable said AARS to incorporate an amino acid analog of a natural amino acid substrate of said AARS into a protein in vivo, comprising:

(a) providing a three-dimensional structure model of said AARS with said natural amino acid substrate;

(b) providing a rotamer library for said amino acid analog;

(c) identifying, based on said three-dimensional structure model, anchor residues of said AARS interacting with the backbone of said natural amino acid substrate;

(d) identifying, in the binding pocket of said AARS, amino acid position(s) involved in interaction with the side chain of said natural amino acid substrate as candidate variable residue position(s);

(e) providing an AARS-analog backbone structure by substituting said natural amino acid substrate with said amino acid analog in said three-dimensional structure model, wherein the geometric orientation of the backbone of said amino acid analog is specified by the orientation of the backbone of said natural amino acid substrate, and wherein the backbone of said amino acid analog and all anchor residues identified in (c) are fixed in identity and rotameric conformation in relation to said AARS-analog backbone structure;

(f) providing a group of potential rotamers for each of the candidate variable residue position(s) identified in (d), wherein the group of potential rotamers for at least one of said variable residue position(s) has a rotamer selected from each of at least two different amino acid side chains; and (g) analyzing the interaction of each of the rotamers for said amino acid analog and rotamers for said variable residue position(s) with all or part of the remainder of said AARS-analog backbone structure to generate a set of optimized protein sequences;

wherein steps (b)–(d) are carried out in any order, and wherein said set of optimized protein sequences contain said amino acid sequence change(s) in the AARS, which change could enable the AARS to incorporate the amino acid analog into the protein in vivo.

2. The method of claim 1, further comprising:

(h) identifying additional protein sequence changes that favor interaction between said AARS and said amino acid analog, by repeating step (g) while scaling up interactions between said amino acid analog and said variable residue position(s).

3. The method of claim 1, further comprising testing said AARS in vivo for its ability, specificity, and/or efficiency for incorporating said amino acid analog into a protein.

4. The method of claim 2, further comprising testing said AARS in vivo for its ability, specificity, and/or efficiency for incorporating said amino acid analog into a protein.

5. The method of claim 1, wherein said three-dimensional structure model is a known crystallographic or NMR structure.

6. The method of claim 1, wherein said three-dimensional structure model is provided by homology modeling based on a known crystallographic or NMR structure of a homolog of said AARS.

7. The method of claim 6, wherein said homolog is at least about 70% identical to said AARS in the active site region.

8. The method of claim 1, wherein the rotamer library for said amino acid analog is a backbone-independent rotamer library.

9. The method of claim 1, wherein the rotamer library for said amino acid analog is a rotamer library provided by varying both the $\chi 1$ and $\chi 2$ torsional angles by ±20 degrees, in increment of 5 degrees, from the values of said natural amino acid substrate in said AARS structure.

10. The method of claim 1, wherein said AARS is Phe tRNA Synthetase (PheRS).

11. The method of claim 10, wherein said PheRS is from *E. coli*.

12. The method of claim 1, wherein said AARS is from a eukaryote.

13. The method of claim 12, wherein said eukaryote is human.

14. The method of claim 1, wherein said amino acid analog is a derivative of at least one of the 20 natural amino acids, with one or more functional groups not present in natural amino acids.

15. The method of claim 14, wherein said functional group is selected from the group consisting of: bromo-, iodo-, ethynyl-, cyano-, azido-, aceytyl, aryl ketone, a photolabile group, a fluorescent group, and a heavy metal.

16. The method of claim 14, wherein said amino acid analog is a derivative of Phe.

17. The method of claim 1, wherein said set of optimized protein sequences comprises the globally optimal protein sequence.

18. The method of claim 1, wherein said DEE computation is selected from the group consisting of original DEE and Goldstein DEE.

19. The method of claim 1, wherein said analyzing step includes the use of at least one scoring function.

20. The method of claim 19, wherein said scoring function is selected from the group consisting of a van der Waals potential scoring function, a hydrogen bond potential scoring function, an atomic solvation scoring function, an electrostatic scoring function and a secondary structure propensity scoring function.

21. The method of claim 19, wherein said analyzing step includes the use of at least two scoring functions.

22. The method of claim 19, wherein said analyzing step includes the use of at least three scoring functions.

23. The method of claim 19, wherein said analyzing step includes the use of at least four scoring functions.

24. The method of claim 19, wherein said atomic solvation scoring function includes a scaling factor that compensates for over-counting.

25. The method of claim 1, further comprising generating a rank ordered list of additional optimal sequences from said globally optimal protein sequence.

26. The method of claim 25, wherein said generating includes the use of a Monte Carlo search.

27. The method of claim 25, further comprising testing some or all of said protein sequences from said ordered list to produce potential energy test results.

28. The method of claim 27, further comprising analyzing the correspondence between said potential energy test results and theoretical potential energy data.

29. The method of claim 1, wherein said amino acid analog can be buried in the binding pocket of at least one of said set of optimized protein sequences, or wherein said amino acid analog is completely or almost completely superimposable with the natural amino acid substrate in said three-dimensional structure.

30. The method of claim 2, wherein in step (h), interactions between said amino acid analog and said variable residue position(s) are scaled up by a factor of between 2.0 to 20.0, with an increment of 0.5, 1.5, or 2.0.

* * * * *